United States Patent
Lee et al.

(10) Patent No.: US 7,250,174 B2
(45) Date of Patent: Jul. 31, 2007

(54) COSMETIC, PERSONAL CARE, CLEANING AGENT, AND NUTRITIONAL SUPPLEMENT COMPOSITIONS AND METHODS OF MAKING AND USING SAME

(75) Inventors: Sean Lee, Karlsruhe (DE); Susanna Kessler, Ergolding (DE); Oliver Forberich, Oberursel (DE); Claire Buchwar, Wiesbaden (DE); David C. Greenspan, Gainesville, FL (US)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 09/818,466

(22) Filed: Mar. 27, 2001

(65) Prior Publication Data
US 2002/0086039 A1   Jul. 4, 2002

Related U.S. Application Data

(60) Provisional application No. 60/197,162, filed on Apr. 14, 2000, provisional application No. 60/192,216, filed on Mar. 27, 2000.

(51) Int. Cl.
*A61K 6/00* (2006.01)
*A61K 9/00* (2006.01)
*A61K 25/34* (2006.01)
*A61K 8/00* (2006.01)
*A61K 8/18* (2006.01)

(52) U.S. Cl. .............. 424/401; 424/400; 424/404; 424/64; 424/69; 424/70.1

(58) Field of Classification Search ............ 424/400, 424/401, 63, 64, 69, 59, 404
See application file for complete search history.

(56) References Cited

U.S. PATENT DOCUMENTS

| | | | |
|---|---|---|---|
| 3,922,155 A | 11/1975 | Broemer et al. | |
| 3,981,736 A | 9/1976 | Broemer et al. | |
| 4,120,730 A | 10/1978 | Trojer et al. | |
| 4,171,544 A | 10/1979 | Hench et al. | |
| 4,189,325 A | 2/1980 | Barrett et al. | |
| 4,234,972 A | 11/1980 | Hench et al. | |
| 4,366,253 A | 12/1982 | Yagi | |
| 4,478,904 A | 10/1984 | Ducheyne et al. | |
| 4,560,666 A | 12/1985 | Yoshida et al. | |
| 4,604,097 A | 8/1986 | Graves et al. | |
| 4,652,534 A | 3/1987 | Kasuga | |
| 4,698,318 A | 10/1987 | Vogel et al. | |
| 4,737,411 A | 4/1988 | Graves et al. | |
| 4,775,646 A | 10/1988 | Hench et al. | |
| 4,777,041 A | 10/1988 | Mercado | |
| 4,783,429 A | 11/1988 | Shibuya et al. | |
| 4,786,555 A | 11/1988 | Howard | |
| 4,814,165 A * | 3/1989 | Berg et al. | |
| 4,851,046 A | 7/1989 | Low et al. | |
| 4,871,384 A | 10/1989 | Kasuga | |
| 4,965,071 A | 10/1990 | Kawan | |
| 4,994,414 A | 2/1991 | Yamamoto et al. | |
| 5,034,216 A | 7/1991 | Barone et al. | |
| 5,074,916 A | 12/1991 | Hench et al. | |
| 5,290,544 A * | 3/1994 | Shimono et al. | |
| 5,380,360 A | 1/1995 | Noguchi et al. | |
| 5,614,489 A | 3/1997 | Mohammadi et al. | |
| 5,658,332 A | 8/1997 | Ducheyne et al. | |
| 5,735,942 A | 4/1998 | Litkowski et al. | |
| 5,766,611 A * | 6/1998 | Shimono et al. | |
| 5,827,882 A | 10/1998 | Yu et al. | |
| 5,834,008 A | 11/1998 | Greenspan et al. | |
| 5,874,101 A | 2/1999 | Zhong et al. | |
| 5,891,233 A | 4/1999 | Salonen et al. | |
| 5,891,470 A | 4/1999 | Rinaldi et al. | |
| 5,972,384 A | 10/1999 | Thut et al. | |
| 5,977,204 A | 11/1999 | Boyan et al. | |
| 5,990,380 A | 11/1999 | Marotta et al. | |
| 5,997,887 A | 12/1999 | Ha et al. | |
| 6,010,713 A | 1/2000 | Zhong et al. | |
| 6,086,374 A | 7/2000 | Litkowski et al. | |
| 6,224,888 B1 * | 5/2001 | Vatter et al. | |
| 6,517,863 B1 * | 2/2003 | LaTorre et al. | |

FOREIGN PATENT DOCUMENTS

| | | |
|---|---|---|
| EP | 0 261 593 | 3/1988 |
| WO | WO 97/27148 | 7/1997 |
| WO | WO 98/11853 | 3/1998 |
| WO | WO 98/46164 | 10/1998 |

(Continued)

OTHER PUBLICATIONS

Ogina, M et al., "Compositional dependence of the formation of calcium phosphate films on bioglass", *Journal of Biomedical materials Research*, vol. 14, pp. 55-64, 1980.

(Continued)

*Primary Examiner*—Humera N Sheikh
(74) *Attorney, Agent, or Firm*—Kramer, Levin, Naftalis & Frankel LLP

(57) ABSTRACT

The present invention involves new cosmetic, personal care, cleaning agent, biocidal agent, functional food, and nutritional supplement compositions. These new compositions incorporate bioactive glass into cosmetics, personal care items, cleaning agents, biocidal agents, functional foods, and nutritional supplements. The present invention also involves methods of making and methods of using such compositions.

14 Claims, No Drawings

FOREIGN PATENT DOCUMENTS

| | | |
|---|---|---|
| WO | WO 98/46170 | 10/1998 |
| WO | WO 99/13852 | 3/1999 |
| WO | WO 99/16423 | 4/1999 |
| WO | 9937287 * | 7/1999 |
| WO | WO 99/37287 | 7/1999 |
| WO | WO 00/15167 | 3/2000 |
| WO | WO 00/42977 | 7/2000 |
| WO | WO 00/76486 | 12/2000 |
| WO | WO 01/03650 | 1/2001 |
| WO | WO 01/72145 | 10/2001 |

OTHER PUBLICATIONS

Williams, D, *Biocompatibility of Orthopedic Implants*, chapter 6, pp. 130-170, Sep. 1, 1982.

Hulbert, S., "History of Bioceramics", *Ceramics International*, vol. 8, pp. 131-140, 1982.

Hench, L., et al., *Biomaterials: An Interfacial Approach*, pp. 145-148, Academic Press, 1982.

Hench, L. et al., "Surface-Active Biomaterials", *Science*, vol. 226, pp. 630-636, Nov. 9, 1984.

Gross, U. et al., "The Response of Bone to Surface-Active Glasses/Glass-Ceramics", *CRC Critical Reviews in Biocompatibility*, vol. 4, No. 2, pp. 155-179, 1988.

Gross, U. et al., "Surface Activities of Bioactive Glass, Aluminum Oxide, and Titanium in a Living Environment", *Annals New York Academy of Sciences*, pp. 211-226.

Niemi, L. et al., "In vivo behaviour of glasses in the $SiO_2$-$Na_2O$-$CaO$-$P_2O_5$-$Al_2O_3$-$B_2O_3$-system", pp. 1-16.

Hench, L., "Bioactive Glasses and Glass-Ceramics: A Perspective", *CRC Handbook of Bioactive Ceramics*, vol. 1, pp. 7-23.

Birchall, J., The interrelationship between silicon and aluminum in the biological effects of aluminum:, *Silicon and Aluminum in Biology*, pp. 50-67.

Hench, L. et al., "Biological Applications of Bioactive Glasses", *Life Chemistry Reports*, vol. 13, pp. 187-241, 1996.

Schepers, E. et al., "Bioactive Glass Particles of Narrow Size Range: A new material for the repair of bone defects", *Implant Dentistry*, vol. 2, No. 3, pp. 151-156, 1993.

European Search Report for EP 01922745.3 dated Mar. 10, 2006.

* cited by examiner

COSMETIC, PERSONAL CARE, CLEANING AGENT, AND NUTRITIONAL SUPPLEMENT COMPOSITIONS AND METHODS OF MAKING AND USING SAME

RELATED APPLICATIONS

This application claims priority from co-pending U.S. Provisional Application No. 60/192,216, filed Mar. 27, 2000, co-pending U.S. Provisional Application No. 60/197,162, filed Apr. 14, 2000, co-pending U.S. application Ser. No. 09/456,196, filed Dec. 7, 1999, and co-pending U.S. application Ser. No. 09/456,195, filed Dec. 7, 1999. The full disclosure of each of these applications is incorporated herein by reference.

FIELD OF THE INVENTION

The present invention involves new cosmetic, personal care, cleaning agent, biocidal agent, functional food, and nutritional supplement compositions. These new compositions incorporate bioactive glass into cosmetics, cleaning agents, personal care products, biocidal agents, functional foods and nutritional supplements. The present invention also involves methods of making and methods of using such compositions.

BACKGROUND OF THE INVENTION

Preservatives are necessary and important ingredients that ensure the stability and safety of different products. Many problems exist with respect to known preservatives. Many have unwanted effects on the products they are in or on the person or thing for which the products are used. Many are relatively expensive and have no beneficial effects besides preservation. Many, in fact, are not efficacious as preservatives. Many have effects on the products' texture or taste that make them undesirable. Better preservatives are needed.

There has also been a great need for ingredients that can be used safely and beneficially in products that have antibacterial, antifungal, antiviral, ion releasing, anti-inflammatory and/or pH properties in the products themselves and/or on the person or thing for which the product issued. Ingredients that can express one or more of these properties are needed.

SUMMARY OF THE INVENTION

Applicants have found that bioactive glass when used in a wide variety of cosmetics provides exceptional qualities to the cosmetic including a beneficial preservative effect. Applicants also have found that bioactive glass preserves a variety of standard household and industrial cleaning agents. Further, certain bioactive glass compositions provide excellent cleaning properties and greatly enhance the cleaning properties of standard household and industrial cleaning agents. In addition, applicants have found that certain bioactive glass compositions are useful as a functional food and nutritional supplement or used in such. Moreover, certain bioactive glass compositions act as an excellent preservative for food.

In addition, the compositions of this invention can be formulated as disclosed herein to have enhanced and beneficial properties that include antibacterial, antiviral, antifungal, ion-releasing, anti-inflammatory and pH effects. As used herein "bioactive glass" is an inorganic glass material having an oxide of silicon as its major component. The use of bioactive glass for unrelated purposes such as orthopedic repair is described by Larry L. Hench and Jon K. West in "Biological Applications of Bioactive Glasses" Life Chemistry Reports, 1996, Vol. 13, pp. 187-241, the contents of which are incorporated herein by reference.

DETAILED DESCRIPTION OF THE INVENTION

Bioactive glass is a sodium-calcium-phospho-silicate glass. As used herein, the term "bioactive glass" may refer to particulate melt-derived and/or sol-gel derived bioactive glass. In addition, the term "bioactive glass" may be used to refer to an aqueous extract of particulate melt-derived an/or sol-gel derived bioactive glass.

The present invention utilizes bioactive glass preferably between 40 and 96% by weight of silicon dioxide oxide ($SiO_2$), between about 0 and 35% by weight of sodium oxide ($Na_2O$), between about 4 and 46% by weight calcium oxide (CaO), and between about 1 and 15% by weight phosphorus oxide ($P_2O_5$). As referred herein, bioactive glasses are typically silicon dioxide based compositions capable of forming hydroxycarbonate apatite (HCA). More preferably, the glass includes between 40 and 60% by weight of silicon dioxide oxide ($SiO_2$), between about 5-30% by weight of sodium oxide ($Na_2O$), between about 10 and 35% by weight calcium oxide (CaO), and between about 1 and 12% by weight phosphorus oxide ($P_2O_5$). The oxides can be present as solid solutions or mixed oxides, or as mixtures of oxides.

$CaF_2$, $B_2O_3$, $Al_2O_3$, MgO and $K_2O$ may be included in the composition in addition to silicon, sodium, phosphorus and calcium oxides. The preferred range for $B_2O_3$ is between 0 and 10% by weight. The preferred range for $K_2O$ is between 0 and 8% by weight. The preferred range for MgO is between 0 and 5% by weight.

Typically, bioactive glasses have the following composition by weight percentage:

| Component | Wt. Percent |
| --- | --- |
| $SiO_2$ | 40–90 |
| CaO | 4–45 |
| $Na_2O$ | 0–35 |
| $P_2O_5$ | 2–16 |
| $CaF_2$ | 0–25 |
| $B_2O_3$ | 0–4 |
| $K_2O$ | 0–8 |
| MgO | 0–5 |

A more prefered composition by weight percentage for bioactive glass is as follows:

| Component | Wt. Percent |
| --- | --- |
| $SiO_2$ | 40–68 |
| CaO | 5–30 |
| $Na_2O$ | 10–35 |
| $P_2O_5$ | 1–12 |

The present invention includes formulations which may comprise metal ions such as $AgNO_3$, CuO, and ZnO, or other antimicrobial salts, including but not limited to, silver, copper and zinc ions. These metals may be in nitrate or acetate form. The preferred range for these salts is between 0 and 15% by weight. The present invention also includes formulations which do not comprise metal ions.

The most preferred glass is Bioglass®™ (a trademark of University of Florida), which has a composition including about 45% by weight silicon dioxide, about 24.5% by weight sodium oxide, about 6% by weight phosphorus oxide, and about 24.5% by weight calcium oxide. Another preferred material is hydroxyapatite. Another preferred material for several applications are the porous sol-gel glasses.

Particulate, non-interlinked bioactive glass is preferred for many embodiments of the present invention. That is, the glass is in the form of small, discrete particles, rather than a fused matrix of particles or a mesh or fabric (woven or non-woven) of glass fibers. Note that under some conditions the discrete particles of the present invention may tend to cling together because of electrostatic or other forces but are still considered to be non-interlinked. Preferably the particle size is less than about 90 microns; more preferably, less than about 20 microns; even more preferably, less than about 5 microns, and most preferably, less than about 2 microns, as measured by SEM or laser light scattering techniques, although different uses may advantageously use different particle sizes.

The preferred particle size range for the bioactive glass is site and use dependent. Particle sizes less than about 1000 microns and greater than about 2 microns can also be used. Particles of such a small size range generally provide for the advantages of the present invention without eliciting undesirable immune responses.

Without being bound to a particular theory, it is believed that there is a complex relationship between the type of ion being released from the glass, the amount of that ion, the rate at which release occurs, the pH of the surrounding environment, and the resulting anti-microbial or anti-inflammatory response. This effect is observed with respect to the particles of bioactive glass themselves and also in the aqueous solutions derived from the glass particles. Accordingly, in the compositions and uses described below, particulate and/or bioactive glass solutions derived from the particles may be used.

Large particles of bioactive glass do not have appreciable antimicrobial properties. However, small particles of bioactive glass and highly porous bioactive glass do have appreciable antimicrobial properties. Bioactive glass has bactericidal properties and is effective against, for example, *Staph. aureus, Staph. epidermidis*, and various *streptococci*. These bacteria may be found in and on the skin. These antimicrobial properties are enhanced in an aqueous environment. While not being bound by a specific mechanism of action, it is believed that this action is a result, inter alia, of the greatly increased bioactivity of the small particulates, which leads to an increased pH of the surrounding environment. The combined properties of being both broadly bactericidal while at the same time maintaining tissue biocompatibility make a variety of formulations comprising small particles of bioactive glass resistant to microbial contamination and especially suitable for formulations which will contact the skin.

The antimicrobial action increases with decreasing particle size. The preferred particle size depends, in part, on the expected microbial challenge and the desired purity of the formulation comprising bioactive glass For example, formulations having bioactive glass particles averaging 20 microns ordinarily is sufficient. However, for a longer lasting preservative effect or to maintain a higher degree of purity, particles averaging less than five microns as measured by SEM or laser light scattering techniques may be used.

When highly porous bioactive glass is used in place of or in addition to small particles of bioactive glass, the pore size is between about 0 and 500 µm, preferably between about 10 and 150 µm, and more preferably, between about 50 and 100 µm. The degree of porosity of the glass is between about 0 and 85%, preferably between about 30 and 80%, and more preferably between about 40 and 60%. Porous bioactive glass can be prepared, for example, by incorporating a leachable substance into the bioactive glass composition, and leaching the substance out of the glass. Suitable leachable substances are well known to those of skill in the art, and include, for example, sodium chloride and other water-soluble salts. The particle size of the leachable substance is roughly the size of the resulting pore. The relative amount and size of the leachable substance gives rise to the degree of porosity. Also, as described herein, porosity can be achieved using sintering and/or by controlling the treatment cycle of glass gels to control the pores and interpores of the material.

In addition, anti-microbial and anti-inflammatory compositions derived from aqueous extracts of bioactive glass can be formed by placing bioactive glass in an aqueous solution, allowing the glass to dissolve over a suitable period of time, for example, a week or more, and filtering out the dissolved glass particles. The solvent can also be evaporated to provide a solid material with anti-microbial properties. These compositions can be used in situations where elimination, reduction, or prevention of microbes, including but not limited to bacteria, viruses, and fungi would be advantageous, for example, in cosmetic formulations, cleaning agent formulations, functional foods and as a preservative for foods.

The glass composition can be prepared in several ways to provide melt-derived glass, sol-gel derived glass and sintered glass particles. The sintered particles may be in sol-gel derived, unreacted, or pre-reacted melt-derived form.

The glass composition is preferably melt-derived. Melt derived glass is generally prepared by mixing grains of oxides or carbonates, melting and homogenizing the mixtures at high temperatures, typically between about 1250 and 1400° C. The molten glass can be flitted and milled to produce a small particulate material.

In each preparation, it is preferred to use reagent grade glass, especially when the glass is used to prepare materials which ultimately may be administered topically. Bioactive glass particles may be prepared using the melt-derived and grinding process described previously in U.S. Pat. No. 5,204,106, the disclosure of which is incorporated herein by reference. Where particular particle size ranges are desired, sifting may be used to obtain such particles. For optimum sterility, glass particles may be ultrasonically cleaned, packaged in syringes and sterilized with gamma radiation.

The particulate biologically active material used in the present invention may be prepared according to the methods of the art such as taught in U.S. Pat. Nos. 4,159,358; 4,234,972; 4,103,002; 4,189,325; 134,171,544; 4,775,646; 4,857,046 and 5,074,916. For example, the raw materials (e.g., $SiO_2$, $CaO$, $Na_2O$ and $P_2O_5$) are mixed in a Nalgene®™ plastic container on a ball mill for four hours. The mix is then melted in a platinum crucible at 1350° C. and homogenized for 24 hours. The molten glass is poured into distilled, deionized water to produce a glass frit. Alternatively, ribbons may be prepared by pouring the glass over moving rollers. The frit or ribbons may be ground, for example, by one of several means. In one method the frit or ribbons are ground in a mortar and pestle and passed through ASTM sieves to produce the required particle size range.

Alternatively, the frit or ribbons may be ground using a ball-milling or jet milling process.

Bioactive glass may be derived using a drying step, which may include near-equilibrium drying. Near-equilibrium drying in place of or in addition to drying under dry conditions provides for much larger average pore size in the final composition at a given level of $SiO_2$ In addition near-equilibrium drying results in a higher rate of resorption as compared to traditionally prepared sol-gel bioactive glass materials. For example, in-vivo testing of one has shown that more than 50% of sol-gel material made in this manner resorbed at eight weeks. Comparable prior 4555 melt derived bioactive glasses, do not resorb at all by eight weeks. Indeed, it has been suggested that glasses including more than 55% silicon dioxide are not bioactive.

As used herein, near-equilibrium drying is drying under the conditions near the two phase boundaries in the phase diagram at a temperature and pressure sufficient to yield a bioactive glass with large pore structure, i.e., a pore structure sufficient to yield a bioactive glass. For example, near-equilibrium drying may be drying under the conditions near the line for water as illustrated in conventional phase diagrams (or other liquids such as methanol, ethanol, acetone, liquid ($CO_2$, benzene and so on). By manipulating the sealing of the designed drying chamber to adjust the extent of the drying condition away from the equilibrium line and relative humidity (from environmental humidity to 98%), the duration of near-equilibrium drying, and the temperature at which the drying is conducted, one can drastically alter pore size of resultant bioactive glass. For example, increasing the sealing of the drying chamber during drying typically results in an increase in relative humidity and pore diameter. Near-equilibrium drying temperature can also be varied, for example, with water drying. When using liquids other than water, such as those referred to above, one may obtain a faster drying or increase the pore size range of the gel to a large extent.

A sol-gel process is any process that includes the use of a sol-gel in the preparation of bioactive glass. Sol-gel derived glass is generally prepared by synthesizing an inorganic network by mixing metal alkoxides in solution, followed by hydrolysis, gelation, and low temperature (around 200-900° C.) firing to produce a glass. Sol-gel derived glasses produced this way are known to have an initial high specific surface area (SSA) compared with either melt-derived glass or porous melt derived glass. The resulting material contains nanometer-sized purosity and has a SSA ranging from 50-400 $m^2/g$. The sol-gel derived glass does not contain sodium. Thus, when this material comes into contact with an aqueous solution, the dissolution mechanisms are different from those associated with non-sol-gel-derived bioactive glass.

Typically, sol-gel-derived bioactive glasses have the following composition by weight percentage:

| Component | Wt. Percent |
|---|---|
| $SiO_2$ | 49–90 |
| CaO | 5–42 |
| $P_2O_5$ | 1–12 |

A more prefered composition for sol-gel-derived bioactive glasses comprises the following composition by weight percentage:

| Component | Wt. Percent |
|---|---|
| $SiO_2$ | 49–72 |
| CaO | 5–35 |
| $P_2O_5$ | 5–9 |

The sol-gel-derived bioactive glass readily reacts with aqueous solutions because of the high SSA (i.e., there is a tremendous amount of surface area where glass/solution reactions can take place). When immersed in an aqueous solution, the sol-gel-derived bioactive glass begins to react, releasing soluble silica, calcium and phosphate anions. Once the concentration of calcium and phosphate anions is increased to the saturation limit for HAp, a mineralogical, HAp-rich layer will form on the surfaces that comprise the sol-gel-derived bioactive glass, and surrounding surfaces (i.e., hard and soft human tissues).

For example, a reaction mixture including tetraethoxysilane (TEOS), triethylphosphate (TEP), and calcium nitrate can be used to make sol-gel bioactive glasses. Alkoxides of calcium, titanium, zirconium, magnesium, aluminum, iron and potassium also can be used. Other appropriate ingredients will also be apparent to those of ordinary skill in the art. In addition, aerogels may be used. When an aerogel is used, increased pressure is used instead of near-equilibrium drying to achieve larger pore size and greater resorbability.

Sol-gel processing which uses a near-equilibrium drying step yields larger pore size in the final product and permits development of HCA very rapidly for both high and low silicon dioxide content gels. Indeed, these compositions form HCA more rapidly than other gels when exposed to SBF (Simulated Body Fluid, Kokubo, T. et al., J. Biomed. Mater. Res., 24, 721-34, 1990) or physiological fluids. The near equilibrium drying technique also provides for more homogeneous gels which can be heated to higher temperatures while retaining large pore diameter. This permits much better control of the final product e.g. resorbability, homogeneity and physical structure. For example, sol-gel compositions derived without using near-equilibrium drying techniques are not able to provide adequate resorbability at higher levels of silicon dioxide. In contrast, the near-equilibrium drying technique provides gels having excellent resorbability even when high amounts of silicon dioxide are included. Such sol-gel glasses are also more homogeneous than other sol-gel glasses and calcium is distributed uniformly.

This drying technique can be used to prepare all types of sol-gel bioactive glasses. For example, the technique can be used to prepare frit, ribbons, monoliths, powders, coatings, fibers, mats, weaves and composites.

Frit can be ground to very broad ranges of particle size such as from about 2 μm up to 1 mm for any purpose. The monolith can be formed to complex shapes such as various implants. Powders can be made to spherical form and from submicron to a few hundred microns. Such compositions are useful, for example, in bone repair and other orthopedic applications, drug delivery, treating tooth hypersensitivity as well as the remineralization of tooth structure, burn healing and wound healing.

While not being bound to any particular theory, it is believed that the near-equilibrium drying step reduces capillary force inside the pore structure of the gel which results in large pore size. Gels are networks of small colloid particles. The networks includes voids which become pores and pore channels in the final glass composition. It is believed that the moisture of the near-equilibrium drying step enhances the reaction at the neck between two particles in the network and the strength of the neck and "back bone" of the gel structure which reduces shrinkage of the drying structure and ultimately results in gels with large pores.

On the other hand, due to the liquid tension, the pressure difference between the different size of pores and channels is:

$$\Delta P = 2\gamma \cos \theta / r$$

where, $\gamma$ is liquid tension, $\theta$ is contact angle and r is the radius of pores and pore channels. During drying, the pressure difference, $\Delta P$, will pull the network tight enabling pore collapse and gel shrinkage as liquid evaporates. It is believed that near-equilibrium drying allows the liquid inside the pore structure to evaporate under the condition of near equilibrium at a range of temperatures. This keeps liquid vapor pressure inside the channels and pores at high heating conditions which resists the shrinkage and collapse of the gel structure and results in large pore sizes.

Bioactive glass, sol-gel derived bioactive glass and/or aqueous extracts of bioactive glass may be incorporated into various cosmetic, cleaning agent, functional foods, nutritional supplements and other products as described below.

Cosmetics

General

The present invention provides novel cosmetics compositions comprising bioactive glass. While current manufacturing processes generally control microbial contamination when the products are in sealed containers, after unsealing the package, bacteria, fungi and/or mold may contaminate the cosmetics. Often, various antibacterial agents are added to the cosmetics to minimize this process. These antibacterial agents, however, often create negative effects such as skin irritation for the cosmetic user.

A goal of the present invention is to produce cosmetic formulations which, in contrast to presently available cosmetics, exhibit an ability to withstand microbial contamination without creating negative effects such as skin irritation.

In one embodiment of the present invention, bioactive glass may be included in cosmetic formulations to minimize microbial contamination, including contamination by bacteria, fungi and/or mold. The cosmetic compositions can include the aqueous extracts of bioactive glass and/or particles of bioactive glass.

In one embodiment the cosmetic formulation comprises particulate bioactive glass having an average particle size less than 10 microns. In another embodiment particulate bioactive glass having an average particle size less than 5 microns, and preferably less than 2 microns is used. Preferred cosmetic preparations are especially creams, make-up compounds, lipsticks, lotions and salves since the microbiocidal effect of bioactive glass is further enhanced by the moisture contained in these preparations. However, bioactive glass can be added to virtually any cosmetic presently available to improve its resistance to contamination. Accordingly, the cosmetic may be liquid based, or alternatively, other than liquid based. Cosmetic formulations may include, for example, creams, lotions, lipsticks, make-up compounds and tinctures.

In one embodiment the invention provides bioactive glass for use as a preservative of perishable goods. The perishable goods may be, for example, cosmetic and/or pharmaceutical preparations. In another embodiment the present invention provides a preservative which itself contains bioactive glass. The preservative which contains bioactive glass may be added to or included in cosmetic formulations.

A cosmetic formulation in accordance with the present invention may contain an amount of bioactive glass up to 95% of the total weight of the cosmetic formulation, especially up to 70%, more especially up to 50%, or 40%, and even more preferably up to 30% of the weight of the cosmetic formulation. Upper limits of 7% of the weight or 5% of the weight are preferred for some formulations, whereby 3% of the weight is especially preferred in some formulations. Lower limits are 0.01% of the weight, especially 0.1% of the weight, whereby 0.5% of the weight and 1% of the weight are especially preferred as the lowest effective amounts.

In one embodiment the cosmetic formulation comprises a protic solvent. In another embodiment the cosmetic formulation contains bioactive glass which has components within the following ranges on a % weight basis: 40-60% $SiO_2$; 10-30% CaO; 10-35% $Na_2O$; 2-8% $P_2O_5$; 0-25% $CaF_2$; 0-10% $B_2O_3$; 0-8% $K_2O$; and 0-5% MgO.

Cosmetic formulations in accordance with the present invention can be well preserved using bioactive glass, without having to add skin-irritating cytotoxic and possibly allergen producing chemical preservatives to the preparation. Furthermore, an additional nurturing effect may be achieved through the antimicrobial and inflammation-inhibiting effect of bioactive glass. The anti-inflammatory effects of bioactive glass make it particularly useful in skin care formulations by promoting reductions in irritation, itching, redness and rashes.

In special cases it might be desirable to add the preservative in accordance with the present invention to preparations which have been preserved using standard preservatives in order to achieve synergetic effects.

Bioactive glass has the ability to react with aqueous solutions (i.e., human perspiration, humidity, body fluids) to elicit biological effects such as anti-microbial/antibacterial behavior, UV screening, anti-inflammatory behavior, mineralogical film forming, and therapeutic release of inorganic ions. These effects are considered advantageous for many cosmetic applications, and several examples of cosmetic formulations that can be used to include bioactive glass and/or sol-gel-derived bioactive glass within a cosmetic product are described herein.

Bioactive glass forms a hydroxy carbonate layer (HCA) on protein-containing surfaces such as hair, skin, nails and teeth. This HCA layer can desensitize teeth, harden/thicken nails, protect skin and modify hair texture.

Bioactive glass and/or sol-gel-derived bioactive glass may be effective at absorbing and scattering visible and UV light, making these materials attractive for soft focus and sun-screening applications.

In one embodiment cosmetic products comprise sol-gel derived bioactive glass. The sol-gel-derived bioactive glass is extremely porous, and thus effective at scattering visible and UV light. The scatter of visible light is important for soft focus cosmetic products, which are intended to scatter light from the skin in such a way that skin wrinkles become less visible to the human eye. Further, the scatter of UV light is important for sunscreen products. Thus, the sol-gel-derived bioactive glass is effective at scattering UV light in the UVA and UVB regions of the solar spectrum and provides a soft focusing effect.

Further, the sol-gel-derived bioactive glass reacts with aqueous solutions to form a solution that becomes concentrated in calcium, phosphate anions and soluble silica. When this solution becomes saturated, it can form a mineralogical, HAp-rich layer on the to surrounding human tissue. Thus, the sol-gel-derived bioactive glass is expected to be effective in soft focus products because it is effective at scattering visible light, and the precipitation of the mineralogical layer could act as a skin-tightening agent that would further aid in hiding skin wrinkles.

It should also be noted that in addition to bioactive glass, antibiotics may also be added to cosmetic formulations. The addition of antibiotics to cosmetic products which include bioactive glass is particularly useful in formulations which require topical application.

Methods of Making

The present invention also provides a method of making cosmetic compositions comprising bioactive glass. An effective antimicrobial amount of the bioactive glass is added to or included in a cosmetic formulation. An "effective, antimicrobial amount of bioactive glass" refers to a sufficient amount of bioactive glass having an appropriate particle size to effectively prevent or control microbial contamination. The amount and particle size of bioactive glass to include in a cosmetic formulation will vary depending on the desired length and degree of purity as well as the anticipated microbial challenge. An "effective antimicrobial amount of bioactive glass" also may refer to a sufficient amount of an aqueous extract of bioactive glass to effectively prevent or control microbial contamination. An "effective antimicrobial amount" of bioactive glass may also refer to a combination of particulate bioactive glass and aqueous extract of bioactive glass to effectively prevent or control microbial contamination.

Bioactive glass may be added to or included in cosmetic formulations using, for example, techniques or combinations of techniques such as general mixing with slow medium, moderate, or even vigorous agitation. Sufficient agitation should be provided to achieve relative homogeneity. Preferably, mixing and agitation will avoid excessive aeration and will have a low sheer rate. In addition, antifloculants may be used to keep the particles from clumping together.

Other methods or combinations of methods of blending, dispersing, mixing, combining and/or emulsifying may be utilized. Agitation may be achieved, for example, with standard mixing devices. General mixing and blending may be achieved, for example, with an impeller.

It has been unexpectedly discovered that for many cosmetic base formulations, bioactive glass is easier to homogeneously mix than other common inorganic powders, such as titanium dioxide and zinc oxide powder, for example.

Bioactive glass may be added to or included in virtually any known cosmetic formulation. Applicants anticipate as well that bioactive glass will be suitable for inclusion in any as yet to be developed cosmetic formulation. In one embodiment the bioactive glass may be particulate. In another embodiment the bioactive glass may be an aqueous solution derived from particulate bioactive glass. In still another embodiment the bioactive glass may be a combination of particulate bioactive glass and an aqueous solution derived from bioactive glass.

Applicants have unexpectedly discovered that bioactive glass mixed with oil forms a cream. Likewise, bioactive glass mixed with water unexpectedly forms a cream. The cream resulting from mixing bioactive glass with either oil or water possesses a consistent homogenized texture particularly suitable for cosmetic formulations.

Applicants have unexpectedly discovered that a combination of bioactive glass with standard skin creams give the skin a pleasant-non-oily feeling and look when compared with the same cream applied without the added bioactive glass. Without being bound to any mechanism, it is believed that the bioactive glass has an affinity for oils as well as water and protenaceous matter, which is consistent with the unexpected effect observed by which bioactive glass and oil form a smooth, homogeneous cream consistency. Thus bioactive glass is suitable as an effective treatment for oily/fatty skin.

Bioactive glass and sol-gel derived bioactive glass exhibit many desirable characteristics that would improve cosmetic products. However, the difficulty lies in formulating the cosmetic products in such a way that the bioactive glass and/or sol-gel-derived bioactive glass remain unreacted (passive) while packaged, and then become reactive (active) when applied onto the human body.

Bioactive glass and sol-gel-derived bioactive glass react with aqueous solutions, but are inert when immersed in anhydrous liquids. Thus, bioactive glass and/or sol-gel-derived bioactive glass may be formulated in liquids, pastes, gels or creams that are anhydrous, but water-soluble (or water permeable). In this instance, the bioactive glass remains un-reacted while immersed in the anhydrous liquid, paste, gel or cream, but would be activated when applied to the human body and allowed to react with perspiration, humidity, and/or other aqueous-containing bodily liquids.

In one embodiment, bioactive glass and/or sol-gel-derived bioactive glass for cosmetic products are used in a dispensing system containing two separate vessels (i.e., similar to the dispensing system used for an epoxy). The bioactive glass and/or sol-gel-derived bioactive glass may be could be formulated in an anhydrous liquid, paste, cream or gel within one vessel, while an aqueous liquid, past, cream or gel may be contained within the second vessel.

In another embodiment bioactive glass and/or sol-gel-derived bioactive glass are mixed with an anhydrous liquid, paste cream or gel that evaporated or is metabolized into the skin after being applied to the body. The anhydrous liquid, paste, cream or gel protects the bioactive glass while in the cosmetic package, yet disappears once applied to the body, thus allowing the bioactive glass to react with perspiration, humidity, and/or other aqueous-containing body liquids.

In yet another embodiment, the desirable characteristics associated with bioactive glass and/or sol-gel-derived bioactive glass are achieved by utilizing an aqueous extract of derived from bioactive glass. The bioactive glass and/or sol-gel-derived bioactive glass may be reacted with an aqueous solution until the solution became saturated with calcium, phosphate anions and soluble silica. This solution could then be filtered, buffered to an appropriate pH, and then added to cosmetic formulations to develop cosmetic products in accordance with the present invention. In this embodiment, the formulation may contain aqueous cosmetic ingredients, since there would be no solid bioactive glass or sol-gel-derived bioactive glass available for reaction.

In many cosmetic applications it is desired that the product have pH value of between 5 and 8. Maintaining this pH level with bioactive glass in an aqueous suspension, however, is difficult as the glass will continuously react in solution, increasing the pH value. Applicants have discovered that as little as 1% citric acid can effectively buffer bioactive glass toward more neutral pH values over a long period in an aqueous suspension. This is to be contrasted with the effect of adding a standard buffer, such as HCL-based buffers to the same suspension, which do not maintain pH levels for suitable periods of time. Thus, citric acid is one preferred method of buffering aqueous based solutions with bioactive glass. Bioactive glass is especially useful in an aqueous containing formulation when the formulation is appropriately buffered to ensure that the pH remains near-neutral and when the bioactive glass is coated with a hydrophobic material that prevents the glass from reacting while in formulation.

In another embodiment the bioactive glass and/or sol-gel-derived bioactive glass can be formulated into a dry form incorporating other ingredients, for example colorants and fragrances, and packaged in small packets or caches for single use cosmetic products for skin, hair or nail applications, for example. The dry form may be a powder.

The following raw materials listed in Table 1 were mixed with bioactive glass and produced stable compositions.

TABLE I

Raw Materials Combined with Bioactive Glass

Raw Material

Incromectant AQ
Promyristyl PM-3
Dermol DPG - 2B
Transcutol CG
Octyl Methoxycinnamate
Crodafos N3N
Triethanolamine
Menthyl Anthranilate
Mineral Oil
Incrodet TD7C
Polyderm PPI SiWI
PEG2 Oleamine
Crodafos CAP
Plantaren APB
Polyderm PPI SiWS
Finsolv TN
Crodasinic O
Dermol B-246
GE 1202
Crovol A-40
Crovol A-70
GE SF 96 350 cps
Probutyl 14
Foamtaine CABG
Dermol MS
PPG 10 Cetyl ether
PEG 7 Glyceryl Cocoate
d-Limonene
Oleth-3
Stepanquat ML
Ammonium Lauryl Sulfate
Incromectant LQ
Tergitol NP-9
Coco Hydroxy Sultaine
Crodesta SL-40***
POE20 Sorbitan monooleate
Propylene Glycol
Ethanol
Na Laureth-2 Sulfate
Sorbitan Isostearate
Glycerin
Procetyl AWS
Crodafos SG
Glycerox 767
Cocamide DEA
Jojoba Oil
Abil EM-90

The following raw materials listed in Table 2 were mixed with sol-gel-derived bioactive glass and produced stable compositions.

TABLE II

Raw Materials Combined with Sol-Gel-Derived Bioactive Glass

Raw Material

Dermol M5
PPG 10 Cetyl ether
PEG7 Glyceryl Cocoate
d-Limonene
Oleth-3
Stepanquat ML
Ammonium Lauryl Sulfate
Incromectant LQ
Tergitol NP-9
Coco Hydroxy Sultaine
Crodesta SL-40
POE20 Sorbitan monooleate
Propylene Glycol
Ethanol
Na Laureth-2 Sulfate
Sorbitan Isostearate
Glycerin
Procetyl AWS
Crodafos SG
Glycerox 767
Cocamide DEA
Jojoba Oil
Incromectant AQ
Foamtaine CABG (45%)
Promyristyl PM-3
Abil EM-90
Dermol DPG-2B
Transutol CG
Octyl Methoxycinnamate
Crodafos N3N
Triethanolamine
Menthyl Anthranilate
Mineral Oil
Incrodet TD7C
Polyderm PPI SiWI
PEG2 Oleamine
Crodafos CAP
Plantaren APB
Polyderm PPI SiWS
Finsolv TN
Crodasinic O
Dermol B-246
GE 1202
Crovol A-40
Crovol A-70
GE SF 96 (350 cps)
Probutyl 14

Bioactive glass, including sol-gel derived bioactive glass may be combined with anyhydrous cosmetic ingredients to created stable, non-irritating cosmetic formulations. A list of exemplary anhydrous ingredients is provided in Table III.

TABLE III

Anhydrous Cosmetic Ingredients Combined with Bioactive Glass

Cosmetically acceptable Glycols - including, but not limited to the following:

Glycerin
Propylene Glycol
Butylene Glycol
Hexylene Glycol
2-methyl propane diol
Cosmetically acceptable Alcohols - including, but not limited to the following:

Ethanol
Isopropanol
n-propanol
lauryl alcohol

TABLE III-continued

Anhydrous Cosmetic Ingredients Combined with Bioactive Glass oleyl alcohol
Cosmetically acceptable Esters - including, but not limited to the following:

Isopropyl Myristate
Isopropyl Palmitate
Jojoba Oil
Glyceryl tri caprate/caprylate
Propylene glycol di caprate/caprylate
Sorbitan Esters
Diesters of diacids
Cosmetically acceptable Ethoxylated Materials - including, but not limited to the following:

Ethoxylated Fatty Alcohols
Ethoxylated Fatty Acids
Ethoxylated Sorbitan Esters
Ethoxylated Glycerides
Cosmetically acceptable Propoxylated Materials - including, but not limited to the following:

Propoxylated Fatty Alcohols
Propoxylated Fatty Acids
Esters of Propoxylated Fatty Alcohols
Ethoxylated Propoxylates
Cosmetically acceptable anhydrous ionic surfactants - including, but not limited to the following:

Phosphate esters
Sulfaters
Carboxylates
Fatty amine salts
Quaternary nitrogen salts
Cosmetically acceptable mineral, vegetable and animal derived oils and fats. Cosmetically acceptable silicones including, but not limited to the following:

Dimethicone
Simethicone
Cyclomethicone
Dimethicone ethoxylates and propoxylates
Cosmetically acceptable fluorocarbons and derivatives - including, but not limited to the following:

Zonyls
Fluorcarbon alcohols
Cosmetically acceptable aerosol propellants - including, but not limited to the following:

Propane
Butane
Pentane
Isobutane
HFC, CFC, HCFC

Bioactive glass, including sol-gel derived bioactive glass may be combined with anyhydrous and hydrous cosmetic ingredients to created stable, non-irritating cosmetic formulations. Anhydrous and hydrous cosmetic ingredients may be used in a two-compartment dispensing system. A list of exemplary anhydrous and hydrous cosmetic ingredients is provided in Table IV.

TABLE IV

Anhydrous and Hydrous Ingredients Which May Be Used in a Two-Compartment Dispensing System Cosmetically acceptable Glycols - including, but not limited to the following:

Glycerin
Propylene Glycol
Butylene Glycol

TABLE IV-continued

Anhydrous and Hydrous Ingredients Which May Be Used in a Two-Compartment Dispensing System Hexylene Glycol
2-methyl propane diol
Cosmetically acceptable Alcohols - including, but not limited to the following:

Ethanol
Isopropanol
n-propanol
lauryl alcohol
oleyl alcohol
Cosmetically acceptable Esters - including, but not limited to the following:

Isopropyl Myristate
Isopropyl Palmitate
Jojoba Oil
Glyceryl tri caprate/caprylate
Propylene glycol di caprate/caprylate
Sorbitan Esters
Diesters of diacids
Cosmetically acceptable Ethoxylated Materials - including, but not limited to the following:

Ethoxylated Fatty Alcohols
Ethoxylated Fatty Acids
Ethoxylated Sorbitan Esters
Ethoxylated Glycerides
Cosmetically acceptable Propoxylated Materials - including, but not limited to the following:

Propoxylated Fatty Alcohols
Propoxylated Fatty Acids
Esters of Propoxylated Fatty Alcohols
Ethoxylated Propoxylates
Cosmetically acceptable anhydrous ionic surfactants - including, but not limited to the following:

Phosphate esters
Sulfaters
Carboxylates
Fatty amine salts
Quaternary nitrogen salts
Cosmetically acceptable mineral, vegetable and animal derived oils and fats. Cosmetically acceptable silicones including, but not limited to the following:

Dimethicone
Simethicone
Cyclomethicone
Dimethicone ethoxylates and propoxylates
Cosmetically acceptable fluorocarbons and derivatives - including, but not limited to the following:

Zonyls
Fluorcarbon alcohols
Cosmetically acceptable amides - including, but not limited to the following:

Fatty acid diethanolamides
Fatty acid monoethanolamides
Fatty acid dimethylamnopropylamides
Cosmetically acceptable Polymers - including, but not limited to the following:

Polyalkenes
Polyoxethylenes
Polyoxypropylenes
Polyamides
Polyesters
Polyurethanes
Cellulosics and derivatives
Polyacrylics
Polymethacrylics
Polysiloxanes
Cosmetically acceptable copolymers
Cosmetically acceptable cosmetic formulation bases - including, but

TABLE IV-continued

Anhydrous and Hydrous Ingredients Which May Be Used in a Two-Compartment Dispensing System not limited to the following:

Emulsifying Waxes
Lubrajels
Zilgels
Jojoba Glaze
Absorption Bases

Bioactive glass, including sol-gel derived bioactive glass also may be combined with cosmetic ingredients which evaporate shortly after being applied to the skin. Such combinations may used to create stable, non-irritating cosmetic formulations. A list of exemplary cosmetic ingredients which may evaporate after being applied to the skin is provided in Table V.

TABLE V

Evaporating Ingredients

Cosmetically acceptable Alcohols - including, but not limited to the following:

Ethanol
Isopropanol
n-propanol
Cosmetically acceptable Esters - including, but not limited to the following:

Ethyl acetate
Butyl acetate
Cosmetically acceptable Ethoxylated Materials - including, but not limited to the following:

Ethoxydiglycol
Cosmetically acceptable silicones - including, but not limited to the following:

Cyclomethicone
Dimethicone
Cosmetically acceptable ketones - including, but not limited to the following:

Acetone
Methyl Ethyl Ketone
Cosmetically acceptable Aliphatic compounds - including, but not limited to the following:

n-alkanes
branched alkanes
Permethyls
Aerosol propellant gases
Cosmetically acceptable fluorocarbons, chloro fluoro carbons, hydro fluoro carbons and hydro chloro fluoro carbons - including, but not limited to the following:

Aerosol propellant gases

One aspect of the present invention will be more clearly understood with reference to the following non-limiting examples of cosmetic and personal care products and formulations which are suitable for use with bioactive glass.

Categories of Cosmetics and Personal Care Health Products

The present invention will produce novel formulations of a variety of cosmetic and personal care products including but not limited to: pigmentation and sun care products; diaper, baby wipe and hand wipe, baby powder and body powder and diaper rash products; nursing pads (for bras); makeup products; tampon, maxipad and pantiliner products; acne prevention and treatment products; facial cleansing, toning and exfoliating products and makeup removal products; facial moisturizing, anti-wrinkle, eye treatment, hand lotion and body lotion products; foot care products; anti-itch products; anti-bacterial, antiseptic, antibiotic and first aid products; bath and shower soap in bar, liquid and gel form and bath salt products; shampoo and hair detangling products; hair mousse, hair gel and hair spray products; antiperspirant and deodorant products in powder, creme, roll-on, aerosol and stick form; aftershave and shaving lotion products; shaving products in creme, gel, powder and soap forms; depilatory, epilatory and hair bleaching products in creme, wax and powder forms; toothpaste products; mouthwash and mouth rinse products; wig and toupee powder products; shoulder pads; freckle coating products, eye drop products; and contact lens treatment products.

Pigmentation Products

The present invention includes novel formulations which incorporate bioactive glass into various brands of pigmentation products, such as the products marketed under the brand names Bain de Soleil, Banana Boat, Coppertone, Fruit of the Earth, Good Sense, Hawaiian Tropic, Kiss My Face, Neutrogena, and products produced by high-end and generic manufacturers.

Generally, pigmentation products comprise the active ingredient dehydroxyacetone (DHA).

Common formulations of pigmentation products comprise water, glycerin, dihydroxyacetone, octyl palmitate, butylene glycol, cetyl alcohol, PPG-20 methyl glucose ether distearate, stearyl alcohol, acrylates/C10-30 alkyl acrylate crosspolymer, aloe gel, cocoa butter, DEA-cetyl phosphate, dimethicone, disodium EDTA, DMDM hydantoin, eucalyptus oil, fragrance, glyceryl stearate, iodopropyl butylcarbamate, lanolin, magnesium aluminum silicate, PEG-100 stearate, polysorbate 60, sodium metabisulfite, sorbic acid, steareth-20, xanthan gum and various vitamin, mineral, fruit and plant extracts.

Pigmentation products may also include one or more of the following: isoceteth-3 acetate, sorbitan isostearate, polyquaternium-37, glycereth-7 triacetate, dicaprylate/dicaprate, PPG-1 trideceth-6, bisabolol, PEG-20 methyl glucose sesquistearate, caprylic/capric triglyceride, unasaponifables, benzyl alcohol, butylparaben, C12-15 alcohol benzoate, caprylic/capric, triglyceride, caramel, carbamate/acrylate copolymer, carbomer, ceteareth-20, ceteth-10, ceteth-2, cetyl hydroxyethylcellulose, citric acid, diazolidinyl urea, dimethyl isosorbide, dipropylene glycol, disodium EDTA, emulsifying wax, ethoxydiglycol, ethylparaben, imidazolidinyl urea, isoceteth-20, isopropyl palmitate, melanin, methyl gluceth-20, methylparaben, octyl methoxycinamate, panthenol, PEG-7 glyceryl cocoate, petrolatum, phenoxyethanol, polydimethylsiloxane-PPG ether/IPDI copolymer, polysorbate 20, polysorbate 80, propylene glycol, propylparaben, silicone, sodium PCA, sorbitol, steareth-2, stearic acid, tocopheryl acetate, triethanolaminel and witch hazel.

The present invention provides for novel formulations of pigmentation products by incorporating bioactive glass into a combination of any of the above-listed ingredients. In addition, bioactive glass itself can act as a pigment. Also, bioactive glass can be doped with various metals, including but not limited to iron, cobalt, and/or manganese, to produce a desired pigmentation.

Sun Care Products

The present invention includes novel formulations which incorporate bioactive glass into various brands of sun care products, such as the products marketed under the brand names A-FIL, Alba Botanica, Aloe Vera 80, Ambrelle, Bain de Soleil, Banana Boat, Biosun, Blue Lizard, Brite-Life, Bull Frog, Coppertone, DuraScreen, Elta Block, Esoterica, Flents, Fruit of the Earth, Good Sense, Hawaiian Tropic, Jason, Kiss My Face, L.A. Tan, Lily of the Desert, Native Tan, Nature's Gate, Neutrogena, No Ad, Off, Panama Jack, PreSun, Sea & Ski, Shade Sunblock, Sol Bar, Sunbrellas, Sun Splash, Ti-Screen, Water Babies, and products produced by high-end and generic manufacturers.

Pigmentation and sun care formulations comprising bioactive glass provide enhanced UV protection as compared to formulations not comprising bioactive glass. While not being bound by any specific theory, the high and irregular surface area of particulate bioactive glass is thought to contribute to this enhanced UV protection. In addition, the reactive glass surface provides a protective HCA layer to offer additional UV protection, Moreover, these formulations help to mitigate the effects of sun allergies by releasing soluble calcium.

Bioactive glass begins to absorb UV light at wavelengths below 380 nm, and 0% transmittance was observed through a polished, 5 mm glass blank for UV light with a wavelength below 280 nm. Thus, bioactive glass should be an excellent sunblock for the UVB (270-320 nm) region, and a moderately good sunblock for the UVA (320-400 nm) region of solar radiation.

The sun-blocking, effectiveness of bioactive glass should improve as a function of time, after it is applied to human skin. Bioactive glass is expected to react with human perspiration to form a porous, mineralogical, HAp-rich precipitate at the glass surface. This porous, surface precipitate is expected to scatter solar radiation, thus improving the sun-blocking characteristics of the bioactive glass with reaction time. Thus, bioactive glass is considered an active sunscreen ingredient that would improve over time as perspiration from the skin would activate the scattering characteristics that are associated with the HAp-rich surface precipitate.

The transmittance through a 5 mm thick, polished sample of bioactive glass that was reacted with tris-buffered saline solution to form a surface precipitate of HAp was tested. The transmittance through the pre-reacted bioactive glass was found to be less than that through the un-reacted bioactive glass at any wavelength from 280 to 600 nm. Thus, the HAp layer formed by pre-reaction appears to scatter UV and visible light, and the bioactive glass should be more effective at blocking UV radiation once it begins to react with human perspiration on the skin.

Generally, sun care products comprise the active ingredient avobenzone, titanium oxide, zinc oxide, oxybenzone, or sulisobenzone.

Common formulations of sun care products comprise octyl methoxycinnamate, octyl salicylate, homosalate, benzalkonium chloride, water, PVP/eicosene copolymer, dioctyl phosphate, triethanolamine, cetyl alcohol, retinyl palmitate, oat extract, tocopherol acetate, panthenol, dimethicone, trimethylsiloxysilicate, bisabolo, disodium EDTA, sorbitan isostearate, butylene glycol, phenoxyethanol, carbomer, xanthan gum and diasolidinyl urea.

Sun care products may also include one or more of the following: PVP/hexadecene, isopropyl myristate, 2-ethylhexyl salicylate, acrylates/C10-30 alkyl acrylate crosspolymer, acrylates/octylacrylamide copolymer, aloe extract, aluminum stearate, avobenzone (parsol 1789), barium sulfate, benzophenone-3, benzyl alcohol, butylcarbamate, C12-15 alkyl benzoate, ceteareth-20, cetearyl alcohol, cetyl palmitate, cyclomethicone, DEA-cetyl phosphate, DMDM hydantoin, edetate disodium, elastin, emulsifying wax NF, ethylhexyl P-methoxycinnamate, fluoroalkyldimethicone, fragrance, glyceryl monostearate-450, glyceryl stearate SE, hydrolyzed collagen, hydroxypropyl cellulose, imidazolidinyl urea, iodopropynyl, isohexadecane, isopropyl palmitate (palm oil), jojoba oil, menthyl anthranilate, methylparaben, mineral oil, octadecene/MA copolymer, octocrylene, octyl palmitate, octyldodecy neopentanoate, oxybenzone, paraffin, petrolatum, phenethyl alcohol, phenylbenzimidazole sulfonic acid, polyglyceryl-3 distearate, PPG-12/SMDI copolymer, PPG-15 stearyl ether, proplyene glycol, propylparaben, PVP/hexadecene, SD alcohol 40, shea butter, silica, sorbitan sesquioleate, sorbitol, stearic acid, stearoxytrimethylsilane, stearyl alcohol, titanium dioxide, tribehenin, trifluoromethyl C1-4 and zinc oxide.

The present invention provides for novel formulations of sun care products by incorporating bioactive glass into a combination of any of the above-listed ingredients. Examples 1-3 below provide exemplary embodiments of sun care formulations incorporating bioactive glass, including sol-gel-derived bioactive glass.

EXAMPLE 1

Composition of Sunscreen Gel with Bioactive Glass

| INGREDIENTS | wt % |
|---|---|
| Jojoba Glaze | 82.5 |
| Octyl Methoxycinnamate | 7.5 |
| Benzophenone-3 | 5.0 |
| Schott Glass Bioactive Glass (<4 μ ave. part. size) | 5.0 |
| | 100.0 |

EXAMPLE 2

Composition of Sunscreen Gel with Sol-gel-derived Bioactive Glass

| INGREDIENTS | wt % |
|---|---|
| Jojoba Glaze | 82.5 |
| Octyl Methoxycinnamate | 7.5 |
| Benzophenone-3 | 5.0 |
| Schott Glass sol-gel-derived bioactive glass | 5.0 |
| | 100.0 |

EXAMPLE 3

Composition of Sunscreen Gel

Formulas CPD3-32, J, K, N, O, R, S

Sunscreen Base Formula

| INGREDIENTS | % |
|---|---|
| Jojoba Glaze | 87.5 |
| Octyl Methoxycinnamate | 7.5 |
| Benzophenone 3 | 5.0 |
| | 100.0 |

Formulas to be tested
CPD3-32 J=Sunscreen Base Formula (above), SPF~15
CPD3-32 K=Jojoba Glaze, SPF~0
CPD3-32 N=Sunscreen Base Formula+2% 45s, d50=1.6µ
CPD3-32 O=Sunscreen Base Formula+2% 58s, d50=0.771µ
CPD3-32 R=Sunscreen Base Formula+4% 45s, d50=1.6µ
CPD3-32 S=Sunscreen Base Formula+4% 58s, d50=0.77µ

Diaper, Baby Wipe and Handwipe, Baby Powder and Body Powder Products, and Diaper Rash Products The present invention includes novel formulations which incorporate bioactive glass into various brands of diaper, baby wipe and hand wipe, baby powder and body powder products such as the products marketed under the brand names A&D, Aloe Vesta, Alpharma, Ammens, Aveeno, Baby Magic, Balmax, Borofax, Boudreaux's, Brite-Life, Burt's Bees, Caldesene, Calmoseptine, Cashmere Bouquet, Cetaphil, Chubbs, Clinipad, Comfort Bath, Cottonelle, Desitin, Diaparene, Diaper Doubler, Diaper Guard, Dr. Smith's, Drypers, Flander's, Fougera, Gerber, Gold Bond, Goodnites, Good Sense, G&W, Huggies, Johnson & Johnson, Kid Fresh, Kleenex, Little Bottoms, Little Forest, Luvs, Mexsana, Nature Boy & Girl, Neutrogena, Nice 'N Clean, Paladin, Pampers, Phisoderm, Playtex, Pull Ups, Pure 'N Gentle, Purell, Shower to Shower, Smiles, Suave, Sween, Tom's of Maine, Tushies, Vaseline, Wash-Up, Weleda, Wet Ones, and products produced by high-end and generic manufacturers.

The anti-inflammatory, antimicrobial, and hygroscopic properties of bioactive glass are particularly useful in diapers, baby powders, body powders, diaper rash products and moist towelettes to reduce inflammation, rash and odors. In addition, bioactive glass can reduce the acidity of urine and is activated by the aqueous nature of urine.

Generally, diaper products comprise synthetic or natural absorbent materials which absorb moisture, synthetic materials which prevent leakage, and fragrance and/or antibacterial agents.

The present invention provides for novel formulations of diaper products by incorporating bioactive glass into a combination of any of the above-listed ingredients. In addition, bioactive glass may be used in so-called adult brand diaper products.

Generally, baby wipe or hand wipe products comprise the active ingredient disodium cocoamphodiacetae, a protectant such as silicon oil, mineral oil, fatty acids, fatty alcohols or plant oils, and a moisturizer such as aloe gel, propylene glycol and PEG-60.

Common formulations of baby and hand wipe products comprise water, propylene glycol, PEG-75 lanolin, cocoamphodiacetate, polysorbate 20, methylparaben, 2-bromo-2-nitropane-1,3-diol, propylparaben, aloe vera gel and fragrance.

Baby and hand wipe products may also include one or more of the following: cocamidopropyl PG-dimonium chloride phosphate, acrylates/C10-30 alkyl acrylate crosspolymer, acetamidopropyl trimonium chloride, acrylates copolymer, alkyl polyglycoside, aminomethyl propanol, benzalkonium chloride, benzoic acid, C12-15 alkyl benzoate, citric acid, diazolidinyl urea, dimethicone, disodium EDTA, disodium phosphate, DMDH hydantoin, ethyl alcohol, glycerin, isopropyl myristate, malic acid, nonoxynol 9, oleth-20, phosphate, phospholipid CDM, phospholipid EFA, polyaminopropyl biguanide, potassium laureth phosphate, potassium sorbate, retinyl palmitate, SD alcohol 40, simethicone, sodium benzoate, sodium nonoxynol-9, sorbic acid, tetrasodium EDTA, tocopherol acetate and various vitamin and plant extracts.

The present invention provides for novel formulations of baby and hand wipe products by incorporating bioactive glass into a combination of any of the above-listed ingredients.

Generally, baby powder and body powder products comprise talc and/or corn starch, zinc oxide and fragrance.

Common formulations of baby powder and body powder products comprise corn starch or talc, sodium bicarbonate, aloe vera gel, tricalcium phosphate and fragrance.

Baby powder and body powder products may also include one or more of the following: tricalcium phosphate, bentonite (natural clay), kaolin clay, polysaccharides, purified rice bran flour, silica, zinc oxide, hydroxyquinoline, 8-hydroxyquinoline sulfate, isostearic acid, PPG-20, methyl glucose ether, magnesium carbonate, zinc stearate, camphor, benzalkonium chloride and various fruit, mineral, vitamin and herbal extracts.

The present invention provides for novel formulations of baby powder and body powder products by incorporating bioactive glass into a combination of any of the above-listed ingredients.

Generally, diaper rash products comprise zinc oxide and fish or cod liver oil.

Common formulations of diaper rash products comprise petrolatum, lanolin, cod liver oil, fragrance, mineral oil, microcrystalline wax and paraffin.

Diaper rash products may also include one or more of the following: balsam, benzoic acid, water, bismuth subnitrate, borax, silicone, methylparaben, talc, trihydroxystearin, bisabolol, polyparaben and imidazolidinyl urea.

The present invention provides for novel formulations of diaper rash products by incorporating bioactive glass into a combination of any of the above-listed ingredients.

The antimicrobial, anti-inflammatory, and hygoscopic properties of bioactive glass are particularly useful in diaper rash products to reduce inflammation, rash and odors.

Nursing Pads (for Bras)

Bioactive glass may also be incorporated into various brands of nursing pad (for bras), including nursing pads marketed under the brand names Curity, Healthflow, Gerber, Johnson's, Evenflo, Omron, and products produced by high-end and generic manufacturers.

The antimicrobial and anti-inflammatory effects of a bioactive glass are particularly useful in nursing pads (bras) to reduce inflammation, rash and odors.

Makeup Products

The present invention includes novel formulations which incorporate bioactive glass into various brands of makeup products including mascara, eyeshadow, eyeliner and eyebrow pencil, blush, concealer foundation, face powder, lipstick, lip gloss, lip treatment, lipliner, nail polish and nail polish remover products such as the products marketed under the brand names Almay, Alpha Hydrox, Aromatherapaes, Bari, Black Radiance, Blistex, Bonnie Bell, Brite-Life, Burt's Bees, Caboodles, Carmex, Chap-et, Chapstick, Chatterm, Clinipad, Coty, Cover Girl, Curity, Cutex, Dermatone, Garden Botanika, Herpecin-L, Jane, Jason, Kid Care, L'Oreal, Liquimat, Loud Music, M Professional, Max Factor, Maybelline, Milani, Natural Ice, Neutrogena, Noxzema, Ocusoft, Oil of Olay, Orly, Peterson's, Purpose, Revlon, Sally Hansen, Savex, Softlips, Stay Free, Tampax, United Colors of Benetton Cosmetics, Ultimates, Vaseline, Viractin, Wet 'n' Wild, Woltra, Zilactin, and products produced by high-end and generic manufacturers.

The anti-inflammatory and antimicrobial effects of bioactive glass are particularly useful in makeup products to reduce bacteria and inflammation.

Generally, mascara products comprise talc, a wax product, a preservative and coloring agents.

Common formulations of mascara products comprise water, beeswax, cyclopentasilosane, glyceryl stearate, PPG-17 copolymer, carnuba wax, stearic acid, paraffin, butylene glycol, EDTA, polyethylene, nylon-12, polymethylmethacrylate, PVP copolymer, PVP silica, triethanolamine, synthetic wax, hydrolyzed corn starch, panthenol, dimethiconol, isoceteth-20, hydroxyethyl cellulose, diazolidyl urea, methylparaben, simethicone, butylparaben, disodium octylacrylamide/acrylates/butyl aminoethyl methacrylate copolymer, cocoamphodiacetate, tocopheryl acetate, isopropyl titanium triisostrearate, lecithin, triethylamine, 2-oleamido-1,3-octadecanediol and propylparaben.

Mascara products may also include one or more of the following: mica, TEA-stearate, glyceryl stearate, tricontanyl PVP, silk powder, diglycol/CHDM/Isophthalates/sip copolymer, PTFE, stearate, sorbitan laurate, polysorbate 20, acacia, acrylates copolymer, alcohol denatured, aminomethyl propandiol, ammonium acrylates copolymer, ammonium hydroxide, ammonium lanolate, ascorbyl palmitate, benzyl alcohol, BHA, butyl stearate, C9-11 isoparaffin, candelilla wax, carmine, cetyl alcohol, cetyl stearate, chromium hydroxide green, citric acid, cyclomethicone, ethylparaben, fragrance, glycerin, glyceryl rosinate, hydgroplex Hhg Whn, hydrolyzed keratin, hydroxyethylcellulose, imidazolidinyl urea, iron oxides, kaolin, magnesium aluminum silicate, methyl ethyl propyl butylparabens/phenoxyethanol, MIPA-lanolate, MIPA-oleate, nnoxynol-10, oleic acid, oleyl alcohol, PEG-100 stearate, pentaerythrityl tetrastearate, phenoxyethanol, polybutene, polyethylene, polyquaternium 10, polyvinyl alcohol, potassium Ocotxynol-12, phosphate, propylene carbonate, propylene glycol, propyl, quaternium-15, quaternium-18, hectorite, quaternium-22, SD alcohol 40-B, silica, silk powder, sodium dehydroacetate, sodium laureth sulfate, sodium lauryl sulfate, sodium polymethacrylate, sorbitan sesquioleate, talc, titanium dioxide, triclosan, trimethylsiloxysilicate, trisodium EDTA, ultramarines and xanthan gum.

The present invention provides for novel formulations of mascara products by incorporating bioactive glass into a combination of any of the above-listed ingredients.

Generally, eyeshadow products comprise talc, mica, polyethylene fluorethylene, magnesium stearate and coloring agents.

Common formulations of eyeshadow products comprise cyclomethicone, talc, boron nitride, trimethylsiloxysilicate, polyethylene, synthetic wax, microcrystalline wax, zinc stearate, kaolin, dimethicone, retinyl palmitate, tocopheryl acetate, aloe extract, silk powder, silica PTFE, dehydroacetic acid, methylparaben, propylparaben, ethylparaben and diazolidinyl urea.

Eyeshadow products may also include one or more of the following: ascorbyl palmitate, beeswax, benzyldimethylstearylammonium hectorite, BHT, bismuth oxychloride, C12-C15 alkyl benzoate, calcium silicate, candelilla wax, caprylic/capric acid tryglyceride, carnauba wax, chromium hydroxide green, chromium oxide greens iron oxides, citric acid, coco caprylate caprate, D1 tocopherol, hydrogenated oil, hydroxylated lanolin, imidazolidinyl urea, isopropyl triisostearoyl titanate, lauroyl lysine, lauryl lysine, lecithin, lipophilic glyceryl monostearate, magnesium carbonate, manganese violet, methyl polysiloxane, mica, mineral oil, octyldodecyl stearoyl stearate, paraffin, parahydroxybenzoate ester, polymethyl methacrylate, polyvinylidene copolymer, propylene carbonate, quaternium-15, saturated fatty acid glycerides, sodium dehydroacetate, soybean phospholipid soybean lecithin, stearic acid, titanium dioxide, trilaurin, trioctanion, ultramarines, zinc oxides, iron oxides, ferric ferrocyanide, ferric ammonium ferrocyanide, carmine, polyglyceryl-3 diisostearate, hydrogenated coco-glycerides, ethylene/methacrylate copolymer, nylon-12, pentahydrosqualene, acrylates copolymer, polyglycery-4 isostearate, laurylmethicone copolyol, perfluoropolymethyliospropeth phosphate, butylparaben, phenoxyethanol and various coloring agents.

The present invention provides for novel formulations of eyeshadow products by incorporating bioactive glass into a combination of any of the above-listed ingredients.

Generally, eyeliner and eyebrow pencil products comprise talc, mica, polyethylene, fluorethylene, magnesium stearate and coloring agents.

Common formulations of eyeliner and eyebrow pencil products comprise cyclomethicone, synthetic beeswax, arachidyl behenate, microcrystalline wax, quaternium-18 hectorite, mineral oil, propylene carbonate, methylparaben, propylparaben and BHT.

Eyeliner and eyebrow pencil products may also include one or more of the following: PPG-2 myristyl ether propionate ceresin, castor oil, vegetable oil, lanolin, aluminum powder, bronze powder, copper powder, zinc oxide, aluminum powder, ammonium hydroxide, ascorbic acid, ascorbyl palmitate, benzyldimethylstearylammonium hectorite, BHA, bismuth oxychloride, butyl stearate, butylene glycol, butylparaben, candelilla wax, caprylic/capric acid triglyceride, carmine, carnauba cetyl alcohol, carnauba wax, ceresin, cerotic acid, cetyl alcohol, cetyl esters, cetyl palmitate, chromium hydroxide green, chromium oxide greens, citric acid, diazolidinyl urea, dimethicone, ferric ammonium ferrocyanide, fish glycerides, glycerin, hydrogenated castor oil, hydrogenated coco-glycerides, hydrogenated cottonseed oil, hydrogenated fish oil, hydrogenated palm glycerides, hydrogenated vegetable oil, hydroxyethylcellulose, hydroxylated lanolin, ipphilic glyceryl monooleate, iron oxides, isopropyl C12-15-pareth-9 carboxylate, japan wax, lipophilic glyceryl monostearate, manganese violet, mellisic acid, methyl polysiloxane, mica, myricyl alcohol, oleostearine, ozokerite, paraffin, parahydroxybenzoate ester, PEG-8, polyethylene, polysorbate 60, PPG-15, PPG-5 eteth-20, PVP laureth-4, quaternium-18 bentonite, saturated fatty acid glycerides, silica, sorbitan stearate, soybean phospholipid soybean lecithin, stearic acid, stearyl heptanoate, styrene/acrylates copolymerm, talc, tallow glyceride, titanium dioxide, tocopheryl acetate, tristearin, ultramarines, various mineral, vitamin, water, zinc stearate and various vegetable and plant extracts.

The present invention provides for novel formulations of eyeliner and eyebrow pencil products by incorporating bioactive glass into a combination of any of the above-listed ingredients.

Generally, blush products comprise talc, a preservative, an emollient, and coloring agents.

Common formulations of blush products comprise dimethicone, octyl palmitate, talc, nylon-12, neopentyl glycol diisooctanoate, tribehenin, isostearyl behenate, boron nitride, acrylates copolymer, tocopherol, retinyl palmitate, methoxypropylgluconamide, chitin extract, sodium hyaluronate, hydrolyzed glucosaminoglycans, lecithin, candelilla wax, soy amino acids, mimosa wax, pentahydrosqualene, sorbitan trioleate, water, propylene glycol, silica, phenoxyethanol, titanium butylparaben, isopropylparaben, isobutylparaben, BHA, lauryl lysine and methyldihydroiasmonate.

Blush products may also include one or more of the following: acetylated lanolin alcohol, allantoin, ascorbyl palmitate, barium sulfate, BHT, bismuth oxychloride, butylparaben, C12-15, alkyl benzoate, calcium silicate, camphor, carbomer, carmine, cethyl acetate, clove oil, coco caprylate caprate, diazolidinyl urea, ethylparaben, eucalyptus oil, ferric ammonium ferrocyanide, ferric ferrocyanidea, fragrance, imidazolidinyl urea, iron oxides, kaolin, manganese violet, menthol, methylparaben, mica, midazolidinyl urea, mineral oil, oat flour, octyldodecyl stearoyl stearate, panthenol, polyethylene, polyoxymethylene urea, polysorbate 20, polysorbate 80, quaternium-15, sodium dehydroacetate, tetrasodium edtapropylparaben, tin oxide, titanium dioxide, triethanolamine, trimethylsiloxysilicate, trioctanion, ultramarines, various coloring agents, various plant extracts, zinc stearate, hydrogenated coco-glycerides, octyl hydroxystearate, ultramarines and various coloring agents.

The present invention provides for novel formulations of blush products by incorporating bioactive glass into a combination of any of the above-listed ingredients.

Generally, concealer and foundation products comprise isoeicosane, carnauba, polyglyceryl-3 diisostearate, silica, titanium oxide and coloring agents.

Common formulations of concealer and foundation products comprise water, butylene glycol, dimethicone, isostearyl alcohol, synthetic wax, cyclomethicone, PEG-20 methyl glucose sesquistearate, sodium stearate, tribehenin, polymethyl methacrylate, salicylic acid, hydrolyzed vegetable protein, silica, talc, microcrystalline wax, dimethicone copolyol, polyglyceryl-6-polyricinoleate, aluminum stearate, boron nitride, dimethiconol, diisostearyl malate, casein, carrageenan, tocopheryl acetate, retinyl palmitate, aloe extract, ascorbic acids, menthol, calcium chloride, nylon-12, perfluoropolymethylisopropyl ether, methylparaben, propylparaben and phenoxyethanol.

Concealer and foundation products may also include one or more of the following: paraffin, pentaerythrityl tetrastearate, octyl hydroxystearate, ceteareth-20, setereth-2, DMDM hydantoin, quaternium-15, dextrin, calcium silicate, zinc stearate, octyldodecyl myristate, tridecyl trimellitate, bisdigly-ceryl caprylate/caprate/isostearate/stea, glyceryl rosinate, acetylated glycol stearate, acetylated lanolin, acetylated lanolin alcohol, acrylates copolymer, alcohol denatured, alkyl octanoate, allantoin, aluminum hydroxide, aluminum starch octenylsuccinate, aminoethylpropanol, arachidyl behenate, ascorbyl palmitate, barium sulfate, beeswax, bentonite, benzoic acid, BHA, BHT, bisabolol, bisacodyl, bismuth oxychloride, butylparaben, C12-15 alcohols octanoate, C12-15 alkyl benzoate, calcium aluminum borosilicate, candelilla wax, caprylic/capric triglyceride, carnauba, castor oil, cellulose gum, cetearyl alcohol, cetearyl octanoate, cethyl acetate, cetyl alcohol, cetyl dimethicone copolyol, cocoyl sarcosine, diazolidinyl urea, dicaprylate/dicaprate, dioctyl adipate, dipropylene glycol, disodium EDTA, disopropyl dimer dilinoleate, ethylene brassylate, ethylene/methacrylate copolymer, ethylene/vinyl acetate copolymer, fragrance, glycerin, glyceryl stearate, hexyl laurate, hydrogenated coco-glycerides, hydrogenated polyisobutane, imidazolidinyl urea, iron oxides, isocetyl stearate, isododecane, isooctahexacontane, isopropyl isostearate, isopropyl palmitate, isopropyl titanium triisostearate, isostearyl neopentanoate, isostearyl palmitate, kaolin, lanolin, lanolin alcohol, lanolin oil, laureth-7, lauroyl lysine, lecithin, lipophilic glyceryl monostearate, magnesium aluminum silicate, magnesium carbonate, magnesium sulfate, methicone, methyl glucose sesquistearate, methyl polysiloxane, mica, mineral oil, myristyl lactate, octamethyl cyclotetrasiloxane, octyl methoxycinamate, octyl palmitate, octyl salicylate, octyl stearate, octyldodecanol, octyldodecy neopentanoate, octyldodecyl stearoyl stearate, ozokerite, panthenol, pectin, PEG-100 stearate, PEG-2 stearate, PEG-20 sorbitan beeswax, PEG-32, PEG-6, PEG-8, petrolatum, phenyl dimethicone, polyethylene, polyglyceryl-4 isostearate, polyglyceryl-6, ricinoleate, polyisobutene, polysorbate 60, propylene glycol, PVP, quaternium-18 hectorite, SD alcohol 40 b, silk powder, sodium chloride, sodium dehydroacetate, sodium hyaluronate, sodium lauroyl sarcosinate, sorbic acid, sorbitan sesquioleate, stearic acid, stearoxytrimethylsilane, stearyl alcohol, stearyl stearoyl stearate, t-butyl hydroquinone, tetrasodium EDTA, titanium dioxide, tocopheryl linoleate, tricontanyl PVP, triethanolamine, trihydroxystearin, trimethylsiloxysilicate, trisodium EDTA, tristearin, ultramarine blue, va/vinyl butyl benzoate, xanthum gum and various coloring agents.

The present invention provides for novel formulations of concealer and foundation products by incorporating bioactive glass into a combination of any of the above-listed ingredients.

Generally, face powder products comprise talc, a preservative, calcium stearate, and coloring agents.

Common formulations of face powder products comprise talc, mineral oil, zinc stearate, kaolin, aluminum starch octenylsuccinate, acrylates copolymer, silk powder, silica, propylparaben, methylparaben, calcium silicate, imidazolidinyl urea, iron dioxides and ultramarines.

Face powder products may also include one or more of the following: acetylated lanolin alcohol, ascorbyl palmitate, beeswax, BHT, bismuth oxychloride, camphor, caprylic/capric triglyceride, carmine, clove oil, cyclomethicon, dextrin, diazolidinyl urea, dimethicone, ethylene/acrylic acid copolymer, ethylparaben, eucalyptus oil, fragrance, glyceryl rosinate, hydrogentated lecithin, isopropyl palmitate, lauroyl lysine, lecithin, magnesium stearate, magnesium sulfate, manganese violet, menthol, methicone, methyl-ethyl-propyl-ibutylparabens/phenoxyethanol, mica, nylon-12, oat flour, octyl palmitate, octyldodecanol stearoyl stearate, octyldodecyl myristate, panthenol, phenoxyethanol, phenyl trimethicone, polysorbate 20, propylene glycol, quaternium-15, quaternium-18 hectorite, retinyl palmitate, sodium dehydroacetate, sodium hydrogenated tallow glutamate, sorbitan sesquioleate, sorbitan trioleate, titanium dioxide, tocopheryl acetate, triclosan, tridecyl trimellitate, various coloring agents, various plant extracts, water, aloe extract and allontoin.

The present invention provides for novel formulations of face powder products by incorporating bioactive glass into a combination of any of the above-listed ingredients.

Generally, lipstick and lip gloss products comprise castor oil, caprylic/capric triglycerides, stearic acid, lanolin, polybutene, mineral oil, kanolin, silica, BHT, and coloring agents.

Common formulations of lipstick and lip gloss products comprise trictyldodecyl citrate, isotridecyl isononanoate, C10-20 cholesterol/lanosterol esters, synthetic beeswax, paraffin, cetyl alcohol, candelilla wax, aloe extract, retinyl palmitate, tocopheryl acetate, ascorbyl palmitate, sodium hyaluronate, PEG-20 sorbitan beeswax, quaternium-18 hectorite, benzoic acid, BHA, methylparaben, propylparaben, titanium dioxide, mica, iron dioxides and various coloring agents.

Lipstick and lip gloss products may also include one or more of the following: acetylated lanolin, acrylates copolymer, allantoin, ascorbyl palmitate, beeswax, bis-diglyceryl polyacyladipate-2, bismuth oxychloride, butylparaben, C10-30 cholesterol/lanosterol esters, carnauba, castor oil, cethyl acetate, cetyl dimethicone copolyol, cetyl octanoate, citric acid, cocoa butter, coconut oil, cyclomethicone, cyclopentasiloxane, cyclotetrasiloxane, diisopropyl, dimer dilinoleate, dimethicone, trissostearyl citrate, D1-tocopherol, drometrizole, D-tocopherol, ethylcellulose, fragrance, glyceryl oleate, grapeseed oil, hexyl laurate, hydrogenated polyisobutene, hydrogenated soy glyceride, hydrogenated vegetable oil, hydrolyzed collagen, hydrolyzed glucosaminoglycans, isocetyl stearate, isododecane, isopropyl myristate, isostearyl palmitate, lanolin, magnesium ascorbyl phosphate, menthol, methicone, methyl glucose sesquistearate, microcrystalline wax, mineral oil, myristyl lactate, neopentyl glycol dicoctanoate, octyl hydroxystearate, octyl methoxycinnamate, octyl palmitate, octyldodecanol, oleyl alcohol, oxybenzone, ozokerite, padimate, PEG-20 sorbitan beeswax, pentaerythrityl tetrabehenate, pentaerythrityl tetraisostearate, petrolatum, phytosterol/octyldodecyl lauroyl glutamate, polybutene, polyethelene, polyethylene, polyglyceryl-2 diisostearate, polyglyceryl-3 diisostearate, polyglyceryl-4 isostearate, polymethysilsesquioxane, PPG 51/smdi copolymer, propyl gallate, propylene glycol, PVP/hexadecene copolymer, sesame oil, shellac wax, silica, sodium hyaluronate, sodium lactate, sodium PCA, sodium phosphate, sodium saccharin, sorbic acid, squalane, stearic acid, stearyl dimethicone, sucrose acetate isobutyrate, T-butyl hydroquinone, tocopheryl acetate, trihydroxystearin, triisostearyl citrate, trilsostearin, trimethylsiloxysilicate, urea, various natural and artificial flavorings, various vitamin agents, water, wheat germ oil, caprylic/capric triglyceride, ceresin, trifluoromethyl C1-4 alkyl dimethicone, arachidyl propionate, phenyl trimethicon and BHT.

The present invention provides for novel formulations of lipstick and lipgloss products by incorporating bioactive glass, into a combination of any of the above-listed ingredients.

Example 4 below provides an exemplary embodiments of lipstick formulations incorporating bioactiv glass.

EXAMPLE 4

Lipstick with Bioglass

Formulas CPD3-33 A, B, C

| INGREDIENTS | wt % A | wt % B | wt % C |
| --- | --- | --- | --- |
| Part A | | | |
| Red 7 Ca Lake | 3.0 | 3.0 | 3.0 |
| Red 6 Ba Lake | 1.0 | 1.0 | 1.0 |
| Red 33 Al Lake | 1.0 | 1.0 | 1.0 |
| Castor Oil | 15.0 | 15.0 | 15.0 |
| Part B | | | |
| Castor Oil | 30.6 | 30.6 | 30.6 |
| Carnauba Wax | 2.0 | 2.0 | 2.0 |
| Candellila Wax | 7.0 | 7.0 | 7.0 |
| Ozokerite Wax | 2.0 | 2.0 | 2.0 |
| Microcrystalline Wax | 3.0 | 3.0 | 3.0 |
| Jojoba Oil | 25.0 | 25.0 | 25.0 |
| Vitamin E | 15.0 | 15.0 | 15.0 |

-continued

| INGREDIENTS | wt % A | wt % B | wt % C |
| --- | --- | --- | --- |
| Methyl Paraben | 0.1 | 0.1 | 0.1 |
| Propyl Paraben | 0.2 | 0.2 | 0.2 |
| Schott Glass 45s5 (<4 µ ave. part. size) | 0.1 | 0.1 | 0.1 |
| Part C | | | |
| Talc USP | 10.0 | — | — |
| Bioglass 45s @ 1.6 µ | — | 10.0 | — |
| Bioglass 58s @ 0.77 µ | — | — | 10.0 |
| | 100.0 | 100.0 | 100.0 |

Observations:
1) The Talc Formula did not set as well/quickly as either glass.
2) The 58s glass formula set up somewhat faster and appeared to make a smoother product as compared to the 45s glass formula.
3) The Talc formula showed more feathering (bleeding) at 1 hr.

Generally, lip treatment products comprise moisturizers, healants and protectants such as petrolatum jelly.

Common formulations of lip treatment products comprise white petrolatum, ethylhexyl P-methoxycinnamate, carnuba, hydroxylated milk glycerides, nylon-12, paraffin, tocopheryl acetate, bisabolol, retinyl palmitate, panthenol, lecithin, stearic, soya stearol, zinc sulfate, sodium saccaharin, various natural and artificial flavorings and various plant extracts.

Lip treatment products may also include one or more of the following: 2-ethylhexyl salicylate, 2-octyldodecanol, allantoin, aloe extract, alum, arachadyl propionate, beeswax, benzoic acid, benzophenone-3, BHT, bisacodyl, borage seed oil, camphor, carnuba wax, castor oil, cetyl alcohol, cetyl esters, cocoa butter, corn oil, dimethicone, dimethicone, dipentaerythrityl hexacaprate/hexacaprylate, fragrance, hydrogenated castor oil, isopropyl lanolate, kukui nut oil, lanolin, menthol, methylparaben, microcrystalline wax, mineral oil, mixed wax, octadecene/ma copolymer, octyl methoxycinamate, octyl palmitate, oxybenzone, ozokerite, padimate, paraffin, petrolatum, phenol, polybutene, polyphenylmethylsiloxane 556, polythylene, propylparaben, purified water, saccharin, salicylic acid, SD alcohol 36, stearyl alcohol, sunflower seed oil, talc, tridecyl stearate, tridecyl trimellitate, triisostearin esters, various coloring agents, wax paraffin and white wax.

The present invention provides for novel formulations of lip treatment products by incorporating bioactive glass into a combination of any of the above-listed ingredients.

Generally, lipliner products comprise a wax product, a preservative, mineral oil, stearic acid and coloring agents.

Common formulations of lipliner products comprise castor oil, isopropyl palmitate, lanolin, beeswax, candelilla wax, meadowfoam seed oil, fragrance, sesame oil, polybutene, ozokerite, dioctyldodecyl fluoroheptyl citrate, carnuba wax, paraffin, hydrogenated soy glyceride, propylene glycol, stearic acid, sodium saccharin, propylparaben, propyl gallate and citric acid.

Lipliner products may also include one or more of the following: aloe extract, BHA, bismuth oxychloride, bronze powder, butylparaben, carmine, castor oil, ceresin, copper powder, cyclomethicone, disostearyl dimer dilinoleate, hydrated silica, hydrogenated castor oil, hydrogenated cottonseed oil, hydrogenated vegetable oil, iron oxides, manganese violet methylparaben, mica, PEG-6 beeswax, polybutene, quaternium-18 bentonite, retinyl palmitate, sodium saccharin, synthetic wax, titanium dioxide, tocopheryl acetate, various coloring agents, various natural and artificial flavorings, zinc oxide, asorbyl palmitate, saturated fatty acid glycerides, caprylic/capric acid triglycerides, glyceryl tripalmitate, parahydroxybenzoate ester, soybean phospholipid, soybean lecithin and lipophilic glyceryl monostearate.

The present invention provides for novel formulations of lip liner products by incorporating bioactive glass into a combination of any of the above-listed ingredients.

Generally, nail polish products comprise nitrocellulose, a lacquer dissolved in solvents such as acetone or ethyl alcohol and coloring agents.

Common formulations of nail polish products comprise ethyl acetate, butyl acetate, isopropyl alcohol, nitrocellulose, glyceryl tribenzoate, acetyl tributyl citrate, stearalkonium bentonite, stearalkonium hectorite, glyceryl triacetate, camphor, SD alcohol 40, citric acid, malic acid, phosphoric acid, 2,4-di-t-butylphenyl-3,5-di-t-butyl-4 hydroxyben and tin oxide.

Nail polish products may also include one or more of the following: acrylates copolymer, algae extract, aluminum, amyul acetate, benzophenone-1, biotin, bismuth oxychloride, chromium hydroxide green, chromium oxide greens, diacetone alcohol, dibutyl phthalate, dimethicone copolyol, dipropylene glycol dibenzoate, ethyl tosylamide, etocrylene, ferric ammonium ferrocyanide, ferric ferrocyanide, fiberglass, fragrance, glycois copolymer, guanine, hydrated silica, iron oxides, isobutyl acetate, manganese violet, methyl acetate, mica, N-butyl alcohol, oxidized polyethylene, panthenol, phthalic anhydride, phthalic anhydride/glycerin/glycidyl decandate cop, phthalic anhydride/trimellitic anhydride/glycols copolymer, polyester resin, polyethylene terephithlate, propyl acetate, retinyl palmitate, silica, silver, styrene/acrylates copolymer, sucrose acetate isobutyrate, styrene/acrylates/acrylonitrile copolymer, tetrabutyl phenyl hydroxybenzoate, titanium dioxide, tocopheryl acetate, tosylamide/epoxy resin, tosylamide/formaldehyde resin, tribenzoin, trimellitic anhydride, ultramarines, various coloring agents, stearalkonium hectorite, dimethicone copolyol, acrylate copolymer, dipropylene glycol dibenzoate, tribenzoin, biotin, panthenol, retinyl palmitate, tocopheryl acetate, aluminum powder, bismuth oxychloride, polyester resin, sucrose acetate isobutyrate, diacetone alcohol, benzophenone-1, guanine, toluene, tosylamide/formaldehyde resin, dibutyl phthalate, tetrabutyl phenyl hydroxybenzoate, titanium dioxide, iron dioxides, mica, ferric ammonium ferrocyanide, calcium pantothenate, heptane, etocrylene, acetyl tributy citrate, hydrolyzed keratin and various coloring agents.

The present invention provides for novel formulations of nail polish products by incorporating bioactive glass into a combination of any of the above-listed ingredients.

Bioactive glass and sol-gel derived bioactive glass reacts with aqueous fluids to form a solution that is rich in inorganic elements, such as calcium, phosphorous, sodium and silicon. These inorganic elements can precipitate on nails to form a mineralogical layer (i.e., hydroxyapatite).

This mineralogical layer is expected to add strength to nails.

Examples 5-8 below provide exemplary embodiments of nail care formulations incorporating bioactive glass, including sol-gel-derived bioactive glass.

EXAMPLE 5

Composition of Anhydrous Nail-Strengthening Gel I

| INGREDIENTS | wt % |
| --- | --- |
| Jojoba Glaze | 80.0 |
| Schott Glass Bioactive Glass (<4 μ ave. part. size) | 20.0 |
| | 100.0 |

EXAMPLE 6

Composition of Anhydrous Nail-Strengthening Gel II

| INGREDIENTS | wt % |
| --- | --- |
| Jojoba Glaze | 90.0 |
| Schott Glass Bioactive Glass (<4 μ ave. part. size) | 10.0 |
| | 100.0 |

EXAMPLE 7

Composition of Nail Gel (Anhydrous with Bioactive Glass)

| INGREDIENTS | wt % |
| --- | --- |
| Glycerin | 90.50 |
| Pemulen ® TR-2 | 0.45 |
| Schott Glass Bioactive (<4 μ ave. part. size) | 9.05 |
| | 100.00 |

EXAMPLE 8

Composition of Skin and Nail Treatment (Anhydrous with Sol-gel-derived Bioactive Glass)

| INGREDIENTS | wt % |
| --- | --- |
| Jojoba Glaze | 91.5 |
| Brown Iron Oxide | 0.5 |
| Titanium Dioxide | 0.5 |
| Talc - USP | 2.5 |
| Schott Glass sol-gel-derived bioactive glass | 5.0 |
| | 100.0 |

Generally, nail polish remover products comprise acetone or ethyl acetate.

Common formulations of nail polish remover products comprise ethyl acetate, alcohol, water, propylene carbonate, dimethyl glutarate, dimethyl succinate, dimethyl adipate, gelatin, glycerin, diglycerol, fragrance, isopropanol, propyl acetate, benzophenone-1, castor oil and various coloring agents.

Nail polish remover products may also include one or more of the following: acetone, citric acid, denatonium benzoate, PEG-75 lanolin oil, mineral oil, panthenol and tocopheryl acetate.

Bioactive glass may be incorporated into a combination of any of the above-listed ingredients.

Tampon, Maxipad and Pantiliner Products

The present invention includes novel formulations which incorporate bioactive glass into various brands of tampon, maxipad and pantiliner products such as the products marketed under the brand names Always, Carefree, Kotex, o.b., Playtex, Tampax, and products produced by high-end and generic manufacturers.

Generally, tampon products comprise cotton and/or rayon overwrap and cotton cord.

Tampon products may also include one or more of the following: polyethylene/polyester cover, polysorbate-20, fragrance, and a plastic or cardboard applicator.

Generally, maxipad and pantiliner products comprise cellulose, plastic and adhesive strips. Maxipad and pantiliner products may also include a fragrance.

The present invention provides for novel formulations of tampon, maxipad and pantiliner products by incorporating bioactive glass into a combination of any of the above-listed ingredients.

The antimicrobial and hygroscopic effects of bioactive glass are particularly useful in tampon, maxipad, and pantiliner products to reduce bacteria and odor.

Acne Prevention and Treatment Products

The present invention includes novel formulations which incorporate bioactive glass into various brands of acne prevention and treatment products such as the products marketed under the brand names Acne Aid, Aconmel, Aveeno, Biore, Burt's Bees, Clean & Clear, Clear Logix, Clearasil, Desert Essence, Exact, Fostex, Garden Botanika, Hyland's Homeopathic, Ionax, Jason, Johnson & Johnson, Kiss My Face, Liquimat, Neutrogena, Noxzema, Orange Daily, Oxy, Pamoxyl, Pernox, Pond's, Rezamid, Sal Ac, Salicylic Acid, Sastid, Sebasorb, Stiefel, Stridex, Suave, Sulforcin, Sulfur Soap, Sulpho-Lac, T-Zone, Zirh, and products produced by high-end and generic manufacturers.

Generally, acne prevention and treatment products comprise the active ingredient benzoyl peroxide or salicylic acid.

Common formulations of acne prevention and treatment products comprise active ingredients consisting of a combination of resorcinol, sulfur and alcohol or benzoyl peroxide.

Acne prevention and treatment products may also include one or more of the following inactive ingredients: alcohol, attapulgite, bentonite, butylparaben, carbomer, citric acid, dioctyl sodium sulfosuccinate, disodium EDTA, edetate disodium, EDTA, fragrance, glycerin, hydroxyethylcellulose, hydroxypropyl methylcellulose, iron oxides, isopropyl myristate, kaolin, lauramide dea, methylparaben, parachlorometaxylenol, PEG-8 laurate, potassium hydroxide, propylene glycol, propylparaben, salicylic acid, simethicone, sodium bisulfite, sodium borohydride, sodium chloride, sodium cocoate, sodium hydroxide, sodium polynapthalene sulfonate, sodium tallowate, talc, titanium dioxide, trisodium hedta, various plant and mineral extracts, water, xanthan gum, zinc oxide, aluminum hydroxide, glyceryl stearate SE and PEG-12.

The present invention provides for novel formulations of acne prevention and treatment products by incorporating bioactive glass into a combination of any of the above-listed ingredients.

The antimicrobial and anti-inflammatory properties of bioactive glass are particularly useful in acne prevention and treatment products. Bioactive glass can be used in topical acne creams to reduce inflammation, while also killing the bacteria and micro-organisms that cause acne.

Facial Cleansing, Toning, Exfoliating and Makeup Removal Products

The present invention includes novel formulations which incorporate bioactive glass into various brands of facial cleansing, toning, exfoliating products and makeup removal products such as the products marketed under the brand names Aapri, Albolene, Almay, Alpha Hydrox, Ambi, Aqua Glycolic, Aquanil Lotion, Artra, Aveeno, Basis, Biore, Bodycology, Bonnie Bell, Brite-Life, Burts's Bees, Camocare, Cetaphil, Clean & Clear, Clairol, Clearasil, Clearly Natural, Cover Girl, Curad, Dickinson's, DML, Earth Science, Freeman, Garden Botanika, Ionax, Jason, Jergens, Johnson & Johnson, Keri, Kiss My Face, La Bella, L'Oreal, Maybelline, Moisturel, Neutrogena, Nivea, Noxzema, Oil of Olay, Oxy, Phisoderm, Plenitude, Pond's, Propa pH, Purpose, Reviva, Revlon, RoC, Sea Breeze, Seban, St. Ives Swiss Formula, Stiefel, Stridex, Suave, T-Zone, Ten-O-Six, Vegee Tonic, and products produced by high-end and generic manufacturers.

Generally, facial cleansing, toning, or exfoliating products or makeup removal products comprise camphor, water, menthol, stearic acid, calcium hydroxide, ammonium hydroxide and an exfoliant such as alpha or beta hydroxy acid, retinoic acid, azelaic acid or adapelene.

Common formulations of facial cleansing, toning, exfoliating products and makeup removal products comprise water, glycerin, sodium laureth sulfate, cocamidopropyl betaine, tocopheryl acetate, panthenol, methyl lactate, carylates/steareth-20, methacrylate copolymer, xanthan gum, microcrystalline wax, sodium magnesium, silicate, sodium hydroxide, fragrance, DMDM hydantoin, iodopropynl butyl carbamate, various vitamin, mineral, fruit and vegetable extracts and various coloring agents.

Facial cleansing, toning, and exfoliating products and makeup removal products may also include one or more of the following: 1-hexadecanol, iodopropyl butylcarbamate, acrylate crosspolymer, acrylates/C10-30 alkyl, allantoin, ammonium hydroxide, beeswax, benzophenone-4, benzyl alcohol, beta carotene, BHT, boric acid, butylene glycol, butylparaben, camphor, caprylic/capric triglyceride, carbomer, ceresin, ceteareth-20, cetearyl alcohol, cetearyl isononanoate, cetyl alcohol, cetyl hydroxyethylcellulose, cetyl octanoate, chlorhexidrine digluconate, chromium hydroxide green, citric acid, cocamide mea, cocamidopropyl phosphatidyl pg-dimonium chloride, cocamidopropylamine oxide, colloidal oatmeal, corn germ oil, dea-cetyl phosphate, diazolidinyl urea, dicaprylate/dicaprate, dimethicone, disodium EDTA, disodium laureth sulfosuccinate, disodium lauroamphodiacetate, disodium oleamido PEG-2 sulfosuccinate, disodium ricinoleamido mea-sulfosuccinate, edetate disodium, EDTA, ethoxydiglycol, ethylparaben, gelatin, glyceryl laurate, glyceryl polymethacrylate, glyceryl stearate, glycol DS, hexylene glycol, hydroxycetyl hydroxyethyl dimonium chloride, hydroxypropyl guar hydroxypropyltrimonium chloride, hydroxypropylcellulose, imidazolidinyl urea, iron oxides, isocetyl alcohol, isopropyl myristate, isopropyl palmitate, lactic acid, lanolin oil, laureth-4, laureth-9, lauric acid, lauryl phosphate, lauryl polyglucose, magnesium aluminum silicate, menthol, methyl gluceth 20, methylchloroisothiazolinone, methyldibromo glutaronitirle, methylisothiazolinone, methylparaben, mineral oil, myristic acid, octyl hydroxystearate, olive oil, palmitic acid, paraffin, PEG-10 hydrogenated castor oil, PEG-10 soya sterol, PEG-100 stearate, PEG-120 glucose dioleate, PEG-120 methyl glucose dioleate, PEG-150 distearate, PEG-2 stearate, PEG-20, PEG-200 glyceryl tallowate, PEG-3 distearate, PEG-7 glyceryl cocoate, PEG-8, PEG-80 sorbitan laurate, PEG-9 tridecyl ether, pentasodium penetate, petrolatum, PG-acetate phosphate, phenoxyethanol, phenylethyl alcohol, poloxamer 184, polydecene, polyol alkoxy esters, polyoxyethylene 15 cocoamine phosphate/oleate comp, polyquaternium-10, polyquaternium-24, polyquaternium-7 capryloyl salicylic acid, polysorbate 20, polysorbate 60, polysorbate 80, potassium hydroxide, potassium myristate, potassium palmitate, potassium sorbate, potassium stearate, PPG-10 butanediol, PPG-10 methyl glucose ether, PPG-12 buteth-16, PPG-15 stearyl ether, propylene glycol, propylparaben, quaternium-15, safflower oil, salicylic acid, sesame oil, simethicone, sodium borate, sodium C12-15 alcohol ethoxycarboxylate, sodium chloride, sodium cocoate, sodium cocoyl glutamate, sodium cocoyl isethionate, sodium cocoyl isethionate, sodium dodecylbenzenesulfonate, sodium isethionate, sodium isostearoyl lactylate, sodium lactate, sodium lauroamphoacetate, sodium lauroyl sarcosinate, sodium lauryl sulfate, sodium lauryl sulfoacetate, sodium myristoyl sarcosinate, sodium palm kernelate, sodium PCA, sodium stearate, sodium sulfite, sodium tallowate, sodium trideceth sulfate, sodium cocoyl isethionate, stearamidopropyl pg-dimonium chloride phosphate, steareth-2, steareth-21, stearic acid, stearyl alcohol, sucrose laurate, talc, tea-stearate, tetrasodium EDTA, tetrasodium etibronate, titanium dioxide, triclocarban, pentasodium pentetate, triclosan, triethanolamine, trisodium hedta, tromethamine, sodium cetyl sulfate, oleyl betaine, laureth-3, self-emulsifying wax, cocoamphocarboxyglycinate, lauramide DEA, lauramide MEA, linoleamide DEA, polyethylene, lauryl methyl gluceth-10 dihydroxypropyldimonium chloride, sodium lauroamphodiacetate and decy glucoside.

The present invention provides for novel formulations of facial cleansing, toning, and exfoliating products and makeup removal products by incorporating bioactive glass into a combination of any of the above-listed ingredients.

The anti-inflammatory and antimicrobial effects of bioactive glass are particularly useful in facial cleansing, toning, and exfoliating products and makeup removal products to reduce bacteria and inflammation. Additionally, the abrasive quality of bioactive glass is useful in exfoliation.

Facial Moisturizing Anti-Wrinkle, Eye Treatment and Hand and Body Lotion Products The present invention includes novel formulations which incorporate bioactive glass into various brands of facial moisturizing, anti-wrinkle, anti-aging, eye treatment and hand and body lotion products such as the products marketed under the brand names Acid Mantle, A-Derma, Abra, Alba Botanica, Albolene, Almay, Ala Derm, Allercreme, Aloe Vera 80, Alpha Hydrox, Alpha Keri, AmLactin, Aqua Care, Aqua Glycolic, Aqua Lactin, Aquanil, Asorbase, Arthi-Care, Atrac-Tran, Aveeno, Avon, Baby Magic, Baker Cummins, Balm Barr, Basis, Beauty Without Crvetty, Beta Care, Biore, Bodycology, Brite-Life, Burt's Bees, Calgon, Camocare Gold, Ca-Rezz, Carmol, Carrington, CBI, Cetaphil, Chamberlain, Clairol, Clean & Clear, Complex 15, Coral Springs, Corn Huskers, Curel, Cutar, Cutemol, Dermal Therapy, Dermacerin, Dermasil, Dermatone, Dermovan, DiaDermal, DiabetiDerm, Dixie Health, DML, Doak, DPM, Earthly Elements, Earth Science, Earth Therapeutics, Elta, Epilyt, Esoterica, Estar, Eucerin, Evian, Exorex, Face Lift, Formula 405, Fougera, Freeman, Fruit of the Earth, Galderma, Garden Botanika, Gold Bond, Golden Sun, Good Sense, Healthflow, Hydrox-C, Jamieson & Co., J. C. Brillantine, Jason, Jean Nate, Jergens, Jockey Club, KC & Company, Keri, Kerodex 51, Kiss My Face, La Bella, Lac-Hydrin Five, LactiCare, Lady Esther, Lander, Lanolar, Lantiseptic, Little Forest, Lubrex, Lubriderm, MG-217, Moisturel, Nate' Naturals, Naturade, Naturalife, Nature's Apothecary, Natures Family, Nature's Gate, Neutrogena, Nivea, Noxzema, Nutraderm, Nutra-E, Nutraderm, Nutraplu, Oilatum Ad, Oil of Olay, Optimum Series, Orange Daily, Pacquin, Palmer's, Pen-Kera, Perfect Solutions, Petal Fresh, Plenitude, Pond's, Porcelana, Prax, Pretty Feet & Hands, Proteque, Purpose, Queen Helene, Revlon, Rex Eme, RoC, Rose Milk, Sarah Michaels, Sarna, Sea Breeze, SFC, Seba Nil, Shepard's, Shikai, Simply Be Well, Soft Sense, State of Mind, St. Ives Swiss Formula, Stik, Stretch Mark, Suave, Sudden Change, Sundance, Sween, The Healing Garden, Theraplex, Triple Lanolin, University Medical, U-Lactin, Ultra Mide 25, Vanicream, Vaseline, Vas Pet, Vital Care, Vitec, Wibi, Wild Yam Complex, Woltra, Xpressions, Yardley's of London, Zim's Crack Creme, and products produced by high-end and generic manufacturers.

Bioactive glass is particularly useful in these products since it possesses anti-inflammatory and antimicrobial properties. The mild abrasive and high pH in certain formulations generate an exfoliant effect on the skin to remove wrinkles. In addition, these formulations which incorporate bioactive glass may be used to hide shadows created by wrinkles.

Skin formulations comprising bioactive glass also provide a protective HCA layer on the corneal layer of the skin. In addition, the anti-inflammatory action of bioactive glass reduces redness and irritation while the anti-microbial action disinfects.

Generally, facial moisturizing, anti-wrinkle, and eye care products or hand and body lotion products comprise an emollient, a preservative and collagen.

Common formulations of facial moisturizing, anti-wrinkle, and eye care products and hand and body lotion products comprise water, glycerin, stearic acid, aloe gel, glycol stearate, soya sterol, lecithin, dimethicone, glyceryl stearate, cetyl alcohol, magnesium aluminum silicate, fragrance, carbomer, stearamide AMP, methylparaben, DMDM hydantoin, iodopropynl, butycarbamate, disodium EDTA, butylene glycol, titanium dioxide, various mineral, fruit, vegetable, and vitamin extracts and various coloring agents.

Facial moisturizing, anti-wrinkle, and eye care products and hand and body lotion products may also include one or more of the following: 1-hexadecanol, acemannan hydrogel, acetylated lanolin alcohol, acrylates copolymer, acrylates/C10-30 alkyl acrylate crosspolymer, acrylates/carbamate copolymer, alantoin octyl dimenthyl paba, alcohol, allantointetra EDTA, alpha lipoic acid, aluminum starch octenylsuccinate, ammonium glycolate, ammonium hydroxide, ammonium lactate, apricot kernel oil, ascorbic acid polypeptide (vitamin c), ascorbyl palmitate, avobenzone, beeswax, benzophenone-4, benzyl alcohol, BHT, bisaboloi, blyceryl stearate, boric acid, butyrolactone, C10-30 cholesterol/lanosterol esters, C12-15 alkyl benzoate, C13-14 isoparaffin, calcium chloride, calcium hydroxide, calcium sulfate, camphor, caprylic acid, castor oil, ceramide 3, ceresin, ceteareth 20, cetearyl alcohol, cetearyl octanoate, ceteth-24, cetrimonium chloride, cetyl acetate, cetyl dimethicone, cetyl esters, cetyl octanoate, cetyl palmitate, cetyl ricinoleate, chloride, chlorphenesin, cholecalciferol, cholesteryl isostearate, choleth-24, citric acid, coco caprylate caprate, cocoa butter, cocobetaine, colloidal oatmeal, copolymer, cyclomethicone, cyclopentasiloxane, dea-cetyl phosphate, dea-oleth-3 phosphate, dermasterone (bioactive multi wild yam species complex), diazolidinyl urea, dicaprylate/dicaprate, dicaprylyl ether, dicaprylyl maleate, diisopropyl sebacate, dioctanoate, dioctyl succinate, dipropylene glycol, distearlydimonium chloride, distearyldimonium, emulsifiers, ethoxydiglycol, ethylene brassylate, ethylhexyl P-methoxycinnamate, glycerin, eucalyptol, eucalyptus oil, fumaric acid, gelatin, glucose, glyceryl dilaurate, glycolic acid, glycoproteins, glysine, GMS/PEG 100 stearate, guar gum, hexyl laurate, hyaluronic acid, hydrogenated castor oil, hydrogenated lanolin, hydrogenated polyisobutane, hydrolyzed animal protein, hydroxyethylcellulose, imidazolidinyl urea, isocetyl stearate, isodecyl oleate, isohexadecane, isopropyl isostearate, isopropyl myristate, isopropyl palmitate, isostearic acid, isostearyl alcohol, isostearyl benzoate, isotearyl neopentandate, kaolin (natural clay), lactic acid, lanolin, diazolidinyl urea, laureth-23, laureth-4, laureth-7, lauroyl lysine, linoleamidopropyl pg-dimonium chloride phosphate, linseed oil, magnesium ascorbyl phosphate, magnesium sulfate, malic acid, menthol, menthyl anthranilate, menthyl lactate, methoxypropylgluconamide, methyl gluceth-20, methylcellulose, methylchloroisothiazolinone, methylisothiazol, methylisothiazolinone, mineral oil, mink oil, monoglyceride citrate, myristyl lactate, myristyl myristate, neopentyl glycol dicaprylate/dicaprate, nylon-12, octyl hydroxystearate, octyl methoxycinamate, PEG-8 beeswax, phenylbenzimidazole sulfonic acid, octyl methoxycinnamate, octyl palmitate, octyl salicylate, octyldodecanol, octyldodecyl myristate, octyldodecyl neopentanotate, oleyl sarcosin, oxybenzone, palm oil, palmitic acid, PEG 100 stearate, PEG-10 soya sterol, PEG-100 stearate, PEG-15 cocamine, PEG-4 dilaurate, PEG-40 stearate, PEG-5 glyceryl stearate, PEG-50 stearate, PEG-8 distearate, PEG-8 stearate, petrolatum, PG-dioctanoate, phenol, phenoxyethanol, phenylcarbinol, phenyldimethicone, phospholipids, polyacrylamide, polyglyceryl-3 methyl glucose distearate, polyglyceryl-4 isostearate, polyglycerylmethacrylate, polyoxyl 40 stearate, polysorbate 20, polysorbate 40, polysorbate 60, potassium hydroxide, potassium sorbate, potassium stearate, progesterone USP, propylene glycol, PVM/MA decadiene crosspolymer, PVP/eicosene copolymer, PVP/hexadecene copolymer, pyridoxine HCL (vitamin B6), quaternium-15, resorcinol, retinyl palmitate, saccharide isomerate, salicylic acid, SD alcohol 40-b, shea butter, silk amino acid, sodium benzoate, sodium borate, sodium calcium alginate, sodium carbomer, sodium chloride, sodium DNA, sodium hyaluronate, sodium isostearoyl lactylate, sodium lauryl sulfate, sodium PCA, sodium pyruvate, sodium stearate, sorbic acid, sorbitan laurate, sorbitan stearate, sorbitol, soybean oil, special petrolatum fraction, squalane, steapyrium chloride, stearamide dea, stearamidopropyl PG-dimonium chloride phosphate, steareth-2, steareth-21, stearoxytrimethylsilane, stearyl alcohol, tea, tea-acrylates/c10-30 alkyl acrylate crosspolymer, tea-carbomer 941, TEA-stearate, tetrasodium EDTA, transvector-delivery system (lipo copolymer complex), tri citrate, tricaprin, tridecyl stearate, tridecyl trimellitate, triethanolamine, triisocetyl citrate, trilaurin, trisodium EDTA, trolamine, urea, wool wax, alcohol, collagen, elastin, propylparaben, PEG-40, sodium cetearyl sulfate, stearyl alcohol, quaterinium-22, sodium hydroxide and silica.

The present invention provides for novel formulations of facial moisturizing, anti-wrinkle, and eye care products and hand and body lotion products by incorporating bioactive glass into a combination of any of the above-listed ingredients.

Examples 9 and 10 below provide exemplary embodiments of skin lotion/makeup base and cream foundation makeup formulations incorporating bioactive glass, including sol-gel-derived bioactive glass.

EXAMPLE 9

Composition of Skin Lotion/makeup Base with Sol-gel-derived Bioactive Glass

| INGREDIENTS | wt % |
| --- | --- |
| Mineral Oil (70ssu) | 20.0 |
| Polawax ® | 5.0 |
| Glycerin | 2.0 |
| Deionized Water | 65.4 |
| Jaguar C-14S | 0.5 |
| Phenobact | 1.0 |
| Fragrance (High End Botanicals AFF #ACR2492019E) | 0.1 |
| Citric Acid monohydrate powder | 2.0 |
| Schott Glass sol-gel-derived bioactive glass | 4.0 |
| | 100.0 |

EXAMPLE 10

Cream Foundation Makeup with Bioglass

Formulas CPD3-34 A, B, C

| INGREDIENTS | wt % A | wt % B | wt % C |
| --- | --- | --- | --- |
| Part A | | | |
| Crodafos CES | 3.0 | 3.0 | 3.0 |
| Volpo 10 | 0.8 | 0.8 | 0.8 |
| Volpo 3 | 0.6 | 0.6 | 0.6 |
| Jojoba Oil | 10.0 | 10.0 | 10.0 |
| Cyclomethicone D5 | 5.0 | 5.0 | 5.0 |
| Part B | | | |
| Deionized Water | 59.9 | 59.9 | 59.9 |
| NaOH | 0.1 | 0.1 | 0.1 |
| Volpo 10 | 0.1 | 0.1 | 0.1 |
| $TiO_2$ | 7.0 | 7.0 | 7.0 |
| Yellow Iron Oxide | 0.8 | 0.8 | 0.8 |
| Red Iron Oxide | 0.3 | 0.3 | 0.3 |
| 50/50 Black/Brown Iron Oxide Blend | 0.1 | 0.1 | 0.1 |
| Part C | | | |
| Propylene Glycol | 3.0 | 3.0 | 3.0 |
| Jaguar 13S | 0.3 | 0.3 | 0.3 |
| Part D | | | |
| Talc USP | 8.0 | — | — |
| Bioglass 45s @ 1.6 μ | — | 8.0 | — |
| Bioglass 58s @ 0.77 μ | — | — | 8.0 |
| Part E | | | |
| Germaben II | 1.0 | 1.0 | 1.0 |
| | 100.0 | 100.0 | 100.0 |

Observations: Both 34 B and 34 C have more even application than 34 A (the talc formulation) and both feel much less oily than 34 A after drying. 34 C is less oily than 34 B.

Foot Care Products

The present invention includes novel formulations which incorporate bioactive glass into various brands of foot care products including products directed to treating athlete's foot, fungal conditions and odor, as well as foot pumice products such as the products marketed under the brand names Absorbine Jr., Afiate, Aloe Vesta, Alpha Hydrox, BFI, Baza, Blis-to-Sol, Brite-Life, Carrington, Cruex, Desenex, Desert Essence, Dr. Scholl's, Earth Therapeutics, Fougera, Freeman, Fungi Care, Fungiclear, FungiCure, Funginail, Fungi Nail, Fungus Stop, Gold Bond, Health at Home, Johnson's, LA Cross, Lamisil, Lotrimin, Mavis, Micatin, Miconazole, Neutrogena, NP-27, Odor-Eaters, Orly, Outgrow, Parex, Pinaud, Podiacin, Pretty Feet & Hands, Quinsana, St. Ives Swiss Formula, Sween, Tetterine, Tinactin, Ting, TingAF, Trim, Triple Care, Vaseline, Zeasorb, and products produced by high-end and generic manufacturers.

Foot care formulations comprising bioactive glass are anti-microbial and create a soothing effect. The anti-microbial effect of bioactive glass includes antifugal properties making bioactive glass particularly well-suited for foot care products. In addition, the hygroscopic properties of bioactive glass help to reduce foot moisture. Bioactive glass also can be used to create or be incorporated into a foot pumice. For example, powders may be sintered by any acceptable method to form a porous solid material for use in a foot pumice.

Generally, foot care products comprise the active ingredient allylamine, azole, griseofulvin, oxiconazole or tolnaftate.

Common formulations of foot care products comprise active ingredients consisting of a combination of tolnaftate, zinc undecylenate, miconazole, nitrate, corn starch, zinc oxide, kaolin and benzethonium chloride.

Foot care products may also include one or more of the following inactive ingredients: acetone, acrylate copolymer, aldioxa, behenoxy dimethicone, calendula, carbohydrate acrylic copolymer, ceteareth-6, chloroxylenol, diazolidinyl urea, edetate disodium, fragrance, imidurea, iodine, isobutane, isopropyl myristate, menthol, microporous cellulose, monobasic sodium phosphate, stearamidoethyl diethylamine, myristyl myristate, polysorbate 60, polysorbate 80, potassium iodide, quaternium, SD alcohol 40, sodium bicarbonate, stearalkonium hectorite, stearamidoethyl diethylamine, stearic acid, stearyl alcohol, talc, thymol, triglyceryl diisostearate, wormwood oil, xanthan gum, water, salicylic acid, methyl salicylate, bentonite, camphor, benzethonium chloride, terbinafine hydrochloride, benzyl alcohol, cetyl alcohol, cetyl palmitate, sodium hydroxide, sorbitan monostearate, starch, magnesium stearate and various herbal, plant and mineral extracts.

The present invention provides for novel formulations of foot care products by incorporating bioactive glass into a combination of any of the above-listed ingredients.

Anti-itch Products

The present invention includes novel formulations which incorporate bioactive glass into various brands of anti-itch products such as the products marketed under the brand names A&D Ointment, After Bite, Americaine, Aquaphor, Arctic Spray, Aveeno, Baciguent, Bactine, Benadryl, Betadine, Blue Star, Boil Ease, Caladryl, Caldecort, Campho-Phenique, Chiggerex, Cortaid, Cortizone, Dermarest, Dermoplast, Exorex, Foille, Gold Bond, Good Sense, Humco, Itch-X, Ivarest, Ivy Block, Ivy-Dry, KeriCort-10, Lanabiotic, Lanacane, Lanacort, Lander, Lotrimin, Medi-Quik, Micatin, Mycitracin, Neosporin, Nupercainal, Polysporin, Rhuli, Sarnol-HC, Solarcaine, Sting Kill, Tecnu, Tegrin, Tinactin, Unguentine, and products produced by high-end and generic manufacturers.

Generally, anti-itch products comprise the active ingredient benzocaine, novacaine or bacitracin.

Common formulations of anti-itch products comprise active ingredients consisting of a combination of camphor, benzocaine, pramoxine hydrochloride, zinc acetate or hydrocortisone.

Anti-itch products may also include one or more of the following inactive ingredients: 1-hexadecanol, 5-chloro-2-methyl-4-isothiazolin-3-one (and) 2-met, acetic acid, adhesives, alcohol, aloe vera, aluminum sulfate, ammonia, benzalkonium chloride, benzyl alcohol, bisabolol, butylene glycol, calamine, calcium acetate, carbomer, ceresin, ceteareth-20, cetearyl alcohol, ceteth-2, cetyl alcohol, cetyl palmitate, chlorothymol, citric acid, coal tar solution, diazolidinyl urea, dimethicone, dioctyl sodium sulfosuccinate, diphenhydramine HCl, disodium EDTA, distearlydimonium chloride, edetate disodium, ethoxydiglycol, fragrance, glycerin, glyceryl stearate SE, glyceryl tribehenate, hydroxypropyl methylcellulose, hydroxypropylcellulose, iodopropyl butylcarbamate, isobutane (propellant), isopropanol, isopropyl alcohol, isopropyl myristate, isopropyl palmitate, isostearyl neopentanoate, karaya, laneth-16, lanolin, laureth-23, lidocaine hydrochloride, maltodextrin, menthol, menthol, isopropyl alcohol, methyl gluceth-20, methyl salicylate, methylparaben, mineral oil, oatmeal flour, octoxynol-9, olive oil, panthenol, PEG-2 oleate, petrolatum, polyethylene glycol, polysorbate 40, potassium hydroxide, potato dextrin, PPG-1 trideceth-6, propylene glycol, propylparaben, SD alcohol 38-b, SD alcohol 40, sodium acrylates copolymer, sodium borate, sodium cetearyl sulfate, sodium chloride, sodium citrate, sodium lauryl sulfate, steareth-2, steareth-21, stearic acid, stearyl alcohol, styrene/acrylates copolymer, sulfated castor oil, thymol, titanium dioxide, tocopheryl acetate, triethanolamine, various coloring agents, water, white petrolatum, white wax, zinc oxide, zinc pyrithione, paraffin, yellow wax, maltodextrin, and various fruit, vegetable, mineral and vitamin extracts.

The present invention provides for novel formulations of anti-itch products by incorporating bioactive glass into a combination of any of the above-listed ingredients.

Antibacterial, Antiseptic, Antibiotic and First Aid Products

The present invention includes novel formulations which incorporate bioactive glass into various brands of antibacterial, antiseptic, antibiotic and first aid products such as the products marketed under the brand names Absorbine, B-D, Baciguent, Bactine, Bag Balm, Ben Gay, Betadine, Betasept, BFI, Blue Star, Boil Ease, Brite-Life, Campho-Phenique, Carraklenz, Clinipad, Clocream, Dermoplast, Dyna-hex, Family Medic, Flex-All, Fougera, Glover's, Gold Bond, Good Sense, Hibiclens, Hibistat, Humco, Iodex, Johnson & Johnson, Lanabiotic, Lanacort, Lander, Lanocane, Lavocal, Medi-Quik, Mentholatum, Mineral Ice, Myciguent, Mycitracin, Neosporin, Nexcare, Polysporin, Resinol, Sayman, Sensogard, Spectrocin, Sportscreme, Stopain, Swan, Top Care, Unguentine, Vicks, Zephiran Chloride, and products produced by high-end and generic manufacturers.

Generally, antibacterial, antiseptic, antibiotic and first aid products comprise alcohol, hydrogen peroxide, povo-iodine, phenol or resorcinol.

Common formulations of antibacterial, antiseptic, antibiotic, and first aid products comprise active ingredients consisting of a combination of polymyxin B sulfate, bacitracin zinc, neomycin and pramoxine hydrochloride.

Antibacterial, antiseptic, antibiotic, and first aid products may also include one or more of the following inactive ingredients: bacitracin, benzalkonium chloride, benzoic acid, bismuth-formiciodide, butylparaben, camphor, cholesterolized ointment, citric acid, base, dibasic sodium phosphate, edetate disodium, emulsifying wax, isopropyl alcohol, licocaine hydrochloride, glycerin, hydrogen peroxide, imidurea, isopropyl alcohol, light mineral oil, magnesium carbonate, menthol, methylparaben, microcrystalline wax, octoxynol-9, petrolatum, phosphoric acid, poloxamer 188, polymyxin B sulfate, potassium sorate, pramoxine HCl, propylene glycol, silica, sodium benzoate, sodium lauryl sulfate, sodium matabisulfite, thymoli, tocopheryl acetate, water, white petrolatum and zinc phenol sulfenate.

The present invention provides for novel formulations of antibacterial, antiseptic, antibiotic, and first aid products by incorporating bioactive glass into a combination of any of the above-listed ingredients.

Formulations of particulate bioactive glass yield a composition which is capable of dramatically reducing the amount of time necessary for wound healing to occur and can augment the natural healing process. The effect of these formulations is most dramatically illustrated in the immune compromised patient whose ability to heal wounds is somewhat suppressed.

Particulate bioactive glasses which are useful in treating wounds, burns, and abrasions typically have the following composition by weight percentage:

| Component | Percent |
| --- | --- |
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5 |

The preferred composition of the bioactive glass is:

| | |
| --- | --- |
| $SiO_2$ | 45 |
| CaO | 24.5 |
| $Na_2O$ | 24.5 |
| $P_2O_5$ | 6 |

The preferred particle size range for the bioactive glass is small and less than 90 microns is recommended. Particle sizes less than 10 microns as well as less than 2 microns can also be used. Particles of such a small size range generally are effective without illiciting any undesirable immune response.

Topical antibiotics are antibiotics suitable for skin treatment. Examples of such antibiotics include: chloramphenicol, chlortetracycline, clyndamycin, clioquinol, erythromycin, framycetin, gramicidin, fusidic acid, gentamicin, mafenide, mupiroicin, neomycin, polymyxin B, bacitracin, silver sulfadiazine, tetracycline and chlortetracycline. Those of ordinary skill in the art will appreciate that there are other appropriate topical antibiotics such as those listed in U.S.P.D., for example.

The bioactive glass and topical antibiotic can be combined in any pharmaceutically acceptable carrier to facilitate application to a wound, burn, or abrasion. These compositions can be combined with an ointment, white petrolatum, mineral oil and other substances known to those of ordinary skill in the art.

These bioactive glass and topical antibiotic compositions may also be combined with other wound, burn and abrasion treatments or dressings such as collagen, fibrin, fibronectin, vitamin E, gauze, cotton, cellulosic, synthetic wound or burn dressings and other wound or burn dressings/treatments known to those of ordinary skill in the art. Dressings of fiberglass and fiberglass made from fibers of bioactive glass can also be used.

Bioactive glass may also be used to a skin grafting particulate bioactive glass may be added to the graft before it is placed in its intended location. The graft may also be further treated with a topical antibiotic prior to placement. The application of bioglass to grafts is intended to increase the likelihood that the graft will "take" and incorporate in the host bed.

While not being bound to any particular theory or mechanism, it is believed that the high surface area and reactivity of particulate bioactive glass provides for a release of sodium which increases pH and increase oxygen in the wound or burn which otherwise has a lower pH. This has an antimicrobial effect when bioactive glass is used and when used in combination with an antibiotic permits the antibiotic to function by activating various growth factors implicated in tissue repair. These reactions cause a higher negative surface charge on the glass surface and the development of a high specific surface area (e.g., from 0.5 m2/g by 12 hours) which attracts collagen, fibronectin and cells. Moreover, the bioactive glass provides for the precipitation of calcium and phosphorous naturally present in wound exudate and blood which cause the rapid formation of a calcium and phosphate layer that may incorporate collagen, fibrin and fibronectin to stabilize the wound quickly and effectively. In some cases, wounds, burns, or abrasions healed with the composition or method of the present invention heal without the necessity of scab formation. That is, new epithelial tissue is formed directly.

When bioactive glass is to be used in combination with an antibiotic it is preferable to mix the particulate bioactive glass and the antibiotic just before application to wound, burn, or abrasion. Accordingly, bioactive particulate glass and a topical antibiotic may be incorporated into a two part system wherein bioactive glass and topical antibiotic are mixed and simultaneously applied. For example, a two part mixing syringe with two separate storage chambers and a mixing chamber can be used. Other two part systems could also be used. For example, particulate bioactive glass can be incorporated into a bandage and the topical antibiotic can be applied to a wound, burn, or abrasion followed by application of the bandage. Alternatively, other two part delivery systems may be used.

Soap and Bath Salt Products

The present invention includes novel formulations which incorporate bioactive glass into various brands of bath and shower soap in bar, liquid, gel form and bath salts such as the products marketed under the brand names Abra, Alba Botanica, Albolene, Aloe Vera 80, Alpha Hydrox, Aroma, Aura Cacia, Aussie, Aveeno, Baby Magic, Balmex, Bare Elegance, Basis, Body & Earth, Bodycology, Bubble Factory, Burt's Bees, Calgon, Camay, Capri, Caress, Carrington, Cashmere Bouquet, Cetaphil, Clairol, Clearasil, Clearly Natural, Coast, Conti Castile, Cuticura, Dermalab, Desert Essence, Dial, Dove, Earth Therapeutics, Eucerin, Exorex, Fa, Fels Naptha, Formula 405, Gillette, Grandpa's, Humco, Irish Spring, Ivory, Jason, Jean Nate, Jergens, Johnson & Johnson, Johnson's, Keri, Kirks Castile, Kiss My Face, Lava, Lever 2000, LifeBuoy, Lindora, Lowila, Lubriderm, Lux, Masada, Moisturel, Nate' Naturals, Naturade, Nature's Gate, Neutrogena, Nivea, No Rinse, Noxzema, Oil of Olay, Oilatum, Packer's, Palmolive, PanOxyl Bar, Phisoderm, Polytar, Purell, Pure & Natural, Pure Pleasure, Purpose, Revlon, Safeguard, San Francisco Soap, Sarah Michaels, Sayman, Shield, Shikai, Simply Be Well, Softsoap, Stiefel, St. Ives Swiss Formula, State of Mind, Suave, Summer's Eve, Sween, The Healing Garden, Tom's of Maine, Tone, Ultra Swim, Vaseline, Vel Beauty Bar, Village Naturals, White Rain, Yardley's of London, Zest, and products produced by high-end and generic manufacturers.

The anti-microbial properties of bioactive glass are particularly useful in soap formulations. In addition, since soap-making is generally an anhydrous process, creating such formulations is a relatively straightforward process. Bioactive glass having certain particle sizes, create an abrasive effect and are particularly well-suited for certain hand soaps (i.e., "Lava"). In addition, bioactive glass may be spheroidized for facial soap similar to polymer beads included in certain facial cleaners.

Anti-inflammatory properties of bioactive glass are particularly useful in both soak and anti-itch soak products. Such novel products reduce redness and skin irritation.

Generally, bath and shower soap in bar, liquid and gel form and bath salt products comprise sodium or ammonium hydroxide, tallow, coconut or palm kernel oil and fragrance.

Common formulations of bath and shower soap in bar, liquid, and gel form and bath salt products comprise triclocarboin, soap, sodium tallowate, sodium pamitate, sodium cocoate, palm kernelate types, water, PEG-6, methyl ether, fragrance, glycerin, sorbitol, sodium chloride, tetra sodium etibronate, pentasodium pentetate, BHT and various coloring agents.

Bath and shower soap in bar, liquid, and gel form and bath may also include one or more of the following: acetamidopropyl trimonium chloride, alkyl aryl polyether alcohol, allantoin, aminomethyl propanol, ammonium laureth sulfate, ammonium lauryl sulfate, behenamidopropyl pg-dimonium chloride, benzopheonone 4, BHT, biotin, boric acid, C12-15 alkyl benzoate, calcium pantothenate, carbomer, cetyl alcohol, chromium hydroxide green, cocamide DEA, cocamidopropyl oxide, cocoa butter, cocobetane PEG 18, cocoglyceryl ether sulfonate, coconut fatty acid, corn oil, cottonseed oil, decyl glucoside, diazolidinyl urea, dimethicone, dimethicone copolyol, disodium cocoyl, disodium EDTA, disodium phosphate, EDTA, ethoxydiglycol, ethyl alcohol, etidonic acid, etidronic acid, glyceryl laurate, glycol stearate, glycolipids, guar hydroxypropyltrimonium chloride, hexylene glycol, hydrolyzed silk protein, hydroxpropyl, hydroxypropyl methylcellulose, imidazolidinyl urea, iodopropyl butylcarbamate, isopropyl lanolate, isopropyl myristate, lanolin oil, lauramide DEA, lauramide MEA, laureth-10, laureth-23, lauric acid, lauryl alcohol, lauryl sulfate, lecithin, lemon juice, linoleamide DEA, magnesium cocoate, magnesium laurate, magnesium stearate, methyl gluceth-10, methyl gluceth-20, methylcellulose, methylchloroisothiazolinone, methylisothiazolinone, methylparaben, mineral oil, oleate/cocoate, oleyl alcohol, oleyl lactate, palm acid, palmitic acid, paraffin, PEG 55 propylene glycol oleate, PEG 7 glyceryl cocoate, PEG-12, PEG-120 methyl glucose dioleate, PEG-20, PEG-3 distearate, PEG-5M, PEG-75, PEG-8, PEG-90M, petrolatum, phenoxyethanol, polyquaternium-10, polyquaternium-22, polysorbate 20, PPG-5-ceteth-20, propylene glycol, propylparaben, retinyl palmitate, silk peptide, sodium benzoate, sodium citrate, sodium cocglyceryl ether sulfonate, sodium cocoyl glutamate, sodium cocoyl isethionate, sodium dodecyl benzene sulfonate, sodium dodecylbenzenesulfonate, sodium formate, sodium hydroxide, sodium isethionate, sodium laurate, sodium laureth sulfate, sodium laureth sulfate, sodium lauroyl lactylate, sodium lauroyl sarcosinate, sodium myreth sulfate, sodium palm kernelate, sodium ricinoleate, sodium stearate, sodium styrene/acrylates copolymer, sodium styrenel acrylates/divinylbenzene copolymer, sodium sulfate, stearamidopropyl PG-dimonium chloride phosphate, stearic acid, sunflower seed oil, tallow acid, tealauryl sulfate, tea-oleate, TEA-stearate, titanium dioxide, tocopheryl acetate, triclosan, sodium c14-16 olefin sulfonate, triethanolamine, trisodium EDTA, trisodium etidronate, trisodium HEDTA, ultramarine blue, sodium laureth sulfate, water, disodium laureth sulfosuccinate, cocamidopropyl betaine, sodium laureth-13 carboxylate, fragrance, glycerin, panthenol, aloe gel, ammonium chloride, DMDM hydantoin, PEG-150 distearate, glycol distearate, citric acid, polyquaternium-7, cocamide MEA, tetrasodium EDTA, laureth-7, various coloring agents, and various plant, mineral and vitamin extracts.

The present invention provides for novel formulations of bath and shower soap in bar, liquid, and gel form and bath salt products by incorporating bioactive glass into a combination of any of the above-listed ingredients.

Shampoo Detangling, Hair Mousse, Hair Gel and Hair Spray Products

The present invention includes novel formulations which incorporate bioactive glass into various brands of shampoo, hair detangling, hair mousse, hair gel and hair spray products such as the products marketed under the brand names Adorn, Agree, Alberto VO5, Allercreme, Aloe Vera 80, American Crew, Aqua Net, Aussie, Aussie Land, Baby Magic, Balsam, Breck, Brite-Life, Brylcreem, Citre Shine, Clairol, Color Soft, Condition 3-in-1, Consort, Cortexx, DeepEarth, Denorex, Dep, DHS, Dippity-Do, Dry Look, Dry Style, Elta, European Mystique, Final Net, Finesse, Flex, Free and Clear, Freeman, Freeze It, Frizz Control, Frizz Ease, Garden Botanika, Gillette, Good Sense, Groom Clean, Hask, Head & Shoulders, Henna Gold, Herbold, Infusium 23, Ionil T, Ivory, Jason, Jeris, Jheri Redding, Jhirmack, John Frieda, Johnson & Johnson, Johnson's, Joico, Kiss Kids, Kiss My Face, La Bella, L.A. Looks, Landers, Looney Tunes, L'Oreal, Loving Care, Marci Gelle, Mane 'n Tail, Mink Difference, Nestle, Neutrogena, Nexxus, Nizoral, No Rinse, Ogilvie, Pantene, Paul Mitchell, Perma Soft, Pert Plus, Physique, Pinaud, Protein 29, Pro-V, Prell, Progaine, Pssssst, Queen Helene, Rave, Redken, Revlon, Royal Crown, Russ Kalvin's Generic, Salon Grafix, Salon Selectives, Salon Style, Scalpicin, Sebastian, Sebucare, Sebulex, Sebutane, Selsun Blue, St. Ives Swiss Formula, Stiff Stuff, Style, Suave, Superset, Tegrin, The Dry Look, Theorie, Thermasilk, Thicker Fuller Hair, Tigi, Tom's of Maine, Top Brass, Tres Flores, Tresemme, Ultimate Look, UltraSwim, University Medical, Vaseline, Venture, Vidal Sassoon, Vital Care, Vitalis, White Rain, Wildroot, Willow Lake, Youth Hair, Zincon, and products produced by high-end and generic manufacturers.

Generally, shampoo and hair detangling products comprise ammonium lauryl sulfonate, triethanolamine, lauramide DEA, lecithin, glycol stearate, methylparaben and methylisothiozoline.

Bioactive glass and sol-gel derived bioactive glass can react with aqueous fluids to form a solution that is rich in inorganic elements, such as calcium, phosphorous, sodium and silicon. Incorporating bioactive glass into such hair care products allows these inorganic elements to precipitate on hair to form a mineralogical layer (i.e., hydroxyapatite). This mineralogical layer is expected to add strength to hair, while also possibly improving the "softness" and "style-ability" of hair. In addition, bioactive glass provides an anti-microbial effect which reduces the occurance of dandruff.

Common formulations of shampoo and hair detangling products comprise water, ammonium laureth sulfate, ammonium lauryl sulfate, glycol distearate, dimethicone, cocamide MEA, cetyl alcohol, fragrance, polymethacrylamidopropyl, trimonium chloride, sodium citrate, DMDM hydantoin, sodium chloride, PEG-14M, dihydrogenated tallowmidoethyl hydroxyethylmonium, disodium EDTA, phenoxyethanol, citric acid, methyldibromoglutaronitrile, ammonium xylene-sulfonate and various coloring agents.

Shampoo and hair detangling products may also include one or more of the following: 2-oleamido-1,3-octadecanediol (ceramide-r), acetamide MEA, acrylates/C10-30 alkyl acrylate crosspolymer, acrylic acid polymer (carbomer 1342), alcohol, aloe vera gel, aluminum starch octenylsuccinate, amodimethicone, arginine, benzophenone-3, benzophenone-4, biotin, butylated hydroxytoluene, butylene glycol, butylparaben, carbomer, carboxylic acid, cetrimonium chloride, chloroxylenol, coal tar distillate, cocamide DEA, cocamide MIPA, cocamidopropyl betaine, cocamidopropyl hydroxysultaine, cocamidopropylamine oxide, cocobetaine, cocodimonium hydroxypropyl hydrolyzed hair keratin, cocotrimonium chloride, cyclomethicone, cysteine, DEA-methoxycinnamate, decyl polyglucose, diazolidinyl urea, dimethiconol, dimethyl ether, disodium cocoamphodiacetate, disodium laureth sulfosuccinate, disodium lauroamphodiacetate, disodium oleamido MEA sulfosuccinate, disodium phosphate, disodium ricinoleamido, ergocalciferol, ethylparaben, glycerin distearyldimonium chloride, glycerin, glycol stearate, glycosaminoglycans, guar hydroxypropyltrimonium chloride, hydrochloric acid, hydrolyzed animal protein, hydrolyzed collagen, hydrolyzed keratin, hydrolyzed silk, hydrolyzed vegetable protein, hydrolyzed wheat protein, hydrolyzed wheat starch, hydrolyzed yeast, hydroxypropyl guar hydroxypropyltrimonium chloride, hydroxypropyl methylcellulose, hydroxypropyltrimonium hydrolyzed wheat protein, imidazolidinyl urea, inositol, iodopropyl butylcarbamate, iodopropynyl butylcarbamate, isobutane, isolaureth-6, isostearamidopropyl morpholine lactate, keratin amino acids, ketoconazole, lactamide MEA, lauramide DEA, lauramphoglycinate, laureth-10, laureth-23, laureth-4, laureth-6, lauryl alcohol, lecithin, magnesium citrate, magnesium laureth sulfate, measulfosuccinate, menthol, methenamine, methoxypropylgluconamide, methylchloroisothiazolinone, methylisothiazolinone, methylparaben, mica, octoxynol-40, octyl Dimethyl PABA, octyl hydroxystearate, octyl methoxycinamate, olealkonium chloride, palmitic acid, pantethine, panthenol, panthenyl ethyl ether, pantothenic acid, PEG-12, PEG-120 methyl glucose dioleate, PEG-15 coco polyamine, PEG-150 distearate, PEG-23M, PEG-27 lanolin, PEG-55 propylene glycol oleate, PEG-60 almond glycerides, PEG-600, PEG-7 glyceryl cocoate, PEG-80 sorbitan laurate, phosphoric acid, phytantriol, phytic acid, polyquaternium-16, polyquaternium-10, polyquaternium-11, polyquaternium-30, polyquaternium-4, polyquaternium-46, polyquaternium-7, polysorbate 20, polysorbate 80, potassium cocoyl hydrolyzed collagen, potassium sorbate, PPG-12 buteth-16, PPG-5 laureth 5, PPG-9, propylene glycol, propylparaben, pyrithione zinc, quaternium-15, quaternium-22, quaternium-75, quaternium-80, retinyl palmitate, ricinoleamidopropyl ethyldimonium ethosulfate, SD alcohol 40, serum protein, silk amino acids, silk protein, silsesquioxane copolymer, sodium benzoate, sodium C14-17 alkyl SEC sulfonate, sodium cocoyl sarcosinate, sodium glutamate, sodium hydroxide, sodium hydroxymethyglycinate, sodium laureth sulfate, sodium laureth-13 carboxylate, sodium lauriminodipropionate, sodium lauroyl sarcosinate, sodium lauryl sulfate, sodium methylparaben, sodium myreth sulfate, sodium oleth sulfate, sodium phosphate, sodium styrene/acrylates/divinylbenzene copolymer, sodium sulfate, sodium trideceth sulfate, solubilized coal tar extract, soluble collagen, soyamide DEA, stearyl alcohol, talloweth-60 myristyl glycol, TEA-dodecylbenzenesulfonate, TEA-dodecylphenylsulfonate, TEA-lauryl sulfate, tetrasodium EDTA, tissular fluid extract, titanium dioxide, tocopheryl acetate, topical tar solution, trideceth-12, triethanolamine lauryl sulfate, trimethylsilylamodimethicone, wheat oligosaccharides, wheatgermamidopropyl dimethylamine, xanthan gum, yeast extract, hydrolyzed soy protein, sodium PCA, ethoxydiglycol, linoleamidopropyl PG-dimonium chloride phosphate, hydrogenated polydecene, trimethylolpropane, phenoxyethanol and various fruit, mineral and vitamin extracts.

The present invention provides for novel formulations of shampoo and hair detangling products by incorporating bioactive glass into a combination of any of the above-listed ingredients.

Generally, hair mousse, hair gel and hair spray products comprise mineral oil, lanolin, stearic acid and zinc pyrithione.

Common formulations of hair mousse, hair gel, and hair spray products comprise water, isobutane, polyquaternium-4, propane, propylene glycol, C9-11 pareth-8, DMDM hydantoin, fragrance, panthenol, disodium EDTA, panthenyl ethyl ether, pantethine, lauramine oxide, keratin amino acids and citric acid.

Hair mousse, hair gel, and hair spray products may also include one or more of the following: acetamide MEA, acrylate copolymer, acrylates/dimethicone/methacrylate copolymer, alanine, alcohol denat, allantoin, aminoethylpropanol, aminomethyl propanol, ammonium benzoate, ammonium hydroxide, amodimethicone, arachidonic acid, arginine, ascorbyl palmitate, behenic acid, benzophenone-3, benzophenone-4, betaine, boric acid, butyl ester of PVM/MA copolymer, C13-14 isoparaffin, calcium pantothenate, carbomer, carbopol, catalase, cetearyl octanoate, ceteth-16, ceteth-20, cetrimonium bromide, cetrimonium chloride, cetyl alcohol, chlorhexidine dihydrochloride, cocamide DEA, cocamidopropyl betaine, cocamidopropyl hydroxysultaine, collagen, cyclomethicone, DEA-methoxycinnamate, diazolidinyl urea, diisobutyl adipate, dimethicone copolyol, dimethiconol, dimethyl ether, dimethyl lauramine isostearate, dimethyl stearamine, dioctyl sebacate, distearlydimonium chloride, ethosulfate, ethyl ester of PVM/MA copolymer, ethyldimonium, gelatin, glutamic acid, glycerin, glycine, hyaluronic acidm, hydrofluorocarbon 152A, hydrolyzed elastin, hydrolyzed soy protein, hydrolyzed wheat protein, hydrolyzed wheat starch, hydrophilic polyether polyurethane, hydroxyethyl cellulose, hydroxypropyl guar, hydroxypropyl methylcellulose, iodopropynyl butylcarbamate, isododecane, isopropyl alcohol, isosteareth-10, keratin protein, lactamide MEA, laneth-16, lauramide DEA, lauramide MEA, laureth-11, laureth-23, laureth-4, laureth-7, laureth-9, lecithin, linoleamidopropyl, linoleic acid, lysine, lysine hydroxypropyl trimonium chloride, methylchloroiosothiazolinone, methylchloroisothiazolinone, methylchloroisothiazolinone, methylisothiazoline, methylisothiazolinone, methylparaben, mineral oil, myristoyl hydrolyzed collagen, niacinamide, SD alcohol 40, nonoxynol-10, octyl hydroxystearate, octyl salicylate, octylacrylamide/acrylates copolymer, octylacrylamide/acrylates/butylaminoethyl meth, octylmethoxycinnamate, olealkonium chloride, oleic acid, oleth 20, oleth-16, palmitic acid, palmitoyl myristyl serinate, PEG-15 cocamine chloride, PEG-40 hydrogenated castor oil, PEG-6 cocamide, PEG-60 hydrogenated castor oil, PEG-75 lanolin, PEG-8 sorbitol, phenoxyethanol, phenyl trimethicone, phospholipids, phytantriol, polyacrylamide, polyquaternium-11, polyquaternium-46, polyquaternium-7, polysorbate 20, polysorbate 80, polyzophenone-4, potassium dimethicone copolyol panthenyl phosphate, potassium hydroxide, potassium sorbate, PPG-12-PEG-50 lanolin, PPG-5-ceteth-20, PPG-9 diethylmonium chloride, proline, PVP, pyridoxine HCL, quaternium-15, retinyl palmitate, ribonucleic acid, serine, silk amino acids, silk protein, sodium benzoate, sodium C13-15 pareth-8 butyl phosphate, sodium C13-15 pareth-8 phosphate, sodium C14-16 olefin sulfonate, sodium chloride, sodium cocoyl isethionate, sodium hydroxymethylglycinate (amino acid derived), sodium PCA, sorbitol, soyamide DEA, stearalkonium chloride, steareth-16, steareth-2, stearic acid, stearyl alcohol, tea-dodecylbenzenesulfonate, tetrasodium EDTA, threonine, tocopheryl acetate, trideceth-12, triethanolamine, trisopropanolamine, urethane/C1-C20 peg alkyl copolymer, VA/crotonates/vinyl neodecandate copolymer, various fruit, plant, vitamin extracts, wheat germamidopropyl ethyldimonium ethosulfate, yeast extract, isobutane, AMP-isostearoyl hydrolyzed soy protein, butylene glycol, and SD alcohol 40.

The present invention provides for novel formulations of hair mousse, hair gel, and hair spray products by incorporating bioactive glass into a combination of any of the above-listed ingredients.

The antimicrobial and pH effects of bioactive glass are particularly useful in shampoo and other hair care products to reduce bacteria and to normalize the pH level of hair. In addtion, the ability of bioactive glass to release minerals which bind to the hair surface is useful for enhancing hair strength, body, and volume.

Examples 11-13 below provide exemplary embodiments of shampoo formulations incorporating bioactive glass, including sol-gel-derived bioactive glass.

EXAMPLE 11

Composition of Hair Shampoo with Bioactive Glass

| INGREDIENTS | wt % |
|---|---|
| Standapol ES-2 | 30.0 |
| Crosultaine C-50 | 10.0 |
| Foamid C | 5.0 |
| Deionized Water | 47.3 |
| Jaguar C-14S | 0.5 |
| Phenobact | 1.0 |
| Fragrance (Wildberry AFF #24551) | 0.2 |
| Citric Acid monohydrate powder | 3.0 |
| Schott Glass Bioactive (<4 µ ave. part. size) | 3.0 |
| | 100.0 |

EXAMPLE 12

Hair Shampoos with 45s5 Glass (Three Separate Formulas: CPD3-15A, B, C, D)

| INGREDIENTS | wt % A | wt % B | wt % C | wt % D |
|---|---|---|---|---|
| Standapol ES-2 | 30.0 | 30.0 | 30.0 | 30.0 |
| Consultaine C-50 | 10.0 | 10.0 | 10.0 | 10.0 |
| Foamid C | 5.0 | 5.0 | 5.0 | 5.0 |
| Deionized Water | 48.0 | 48.0 | 48.0 | 48.0 |
| Phenobact | 1.0 | 1.0 | 1.0 | 1.0 |
| Citric Acid monohydrate powder | 1.0 | — | 1.0 | — |
| Schott Glass 45s5 (<4 µ ave. part. size) | 5.0 | — | — | 5.0 |
| | 100.0 | 94.0 | 95.0 | 99.0 |

EXAMPLE 13

Hair Shampoos with Bioactive Glass

Formulas CPD3-31 A, B, C, D

| INGREDIENTS | wt % A | wt % B | wt % C | wt % D |
|---|---|---|---|---|
| Steol CS-230 | 30.0 | 30.0 | 30.0 | 30.0 |
| Crosultaine C-50 | 10.0 | 10.0 | 10.0 | 10.0 |
| Foamid C | 5.0 | 5.0 | 5.0 | 5.0 |
| Deionized Water | 49.0 | 48.0 | 47.0 | 46.0 |
| Phenobact | 1.0 | 1.0 | 1.0 | 1.0 |
| Citric Acid monohydrate powder | — | 1.0 | 2.0 | 3.0 |
| Bioglass (<5 µ ave. part. size) | 5.0 | 5.0 | 5.0 | 5.0 |
| | 100.0 | 100.0 | 100.0 | 100.0 |

Initial pH values $pH_0$ 31A - 8.9
$pH_0$ 31B - 8.2
$pH_0$ 31C - 5.7
$pH_0$ 31D - 4.8

24 hour pH values $pH_{24}$ 31A - 9.6
$pH_{24}$ 31B - 9.2
$pH_{24}$ 31C - 8.5
$pH_{24}$ 31D - 7.2

Anti-Perspirant and Deodorant Products

The present invention includes novel formulations which incorporate bioactive glass into various brands of anti-perspirant and deodorant products in powder, creme, roll-on, aerosol and stick form such as the products marketed under the brand names 5 Day, Allercreme, Almay, Aqua Velva, Arm & Hammer, Arrid XX, Ban, Banish, Brut, Certain Dri, Clearly Fresh & Natural, Crystal Clean, Crystal Stick, Degree, Desert Essence, Dove, Dry Idea, English Leather, Gillette, Hi & Dri, Jason, Jockey Club, Kiss My Face, Lady Crystal, Lady Mitchum, Lady Speed Stick, Lady's Choice, Mennen, Mitchum, Nair, Nature's Gate, Nautica, Nullo, Old Spice, Pinaud, Power Stick, Revlon Hi & Dri, Right Guard, Secret, Soft & Dry, Speed Stick, Suave, Sure, Teen Spirit, Tom's of Maine, Tussy, Soft & Dri, Yodora, and products produced by high-end and generic manufacturers.

The anti-microbial and hygroscopic properties of bioactive glass in deodorant and anti-perspirant formulation control odor causing bacteria, while the anti-inflammatory properties reduce underarm irritation. Bioactive glass may be incorporated into solid amorphous forms, similar to deodorant "crystals". A wipe with the polished solid form also has an anti-microbial effect.

Generally, antiperspirant or deodorant products comprise aluminum chlorohydrate, aluminum chloride, zirconium chlorides or triclosan.

Common formulations of antiperspirant and deodorant products in stick, roll-on, aerosol, creme, pad, and powder form comprise active ingredients consisting of aluminum zirconium tetrachlorohydrex gly or aluminum chlorohydrate.

Anti-perspirant and deodorant products may also include one or more of the following: alcloxa, alcohol, allantoin, aloe vera gel, aluminum chloride, PPG-14 butyl ether, cyclomethicone, baking soda, behenyl alcohol, benzethonium chloride, benzoic acid, BHT, C12-15 alkyl benzoate, C18-36 acid triglyceride, ceteareth-20, cetearyl alcohol, citric acid, corn starch, cyclomethicone, cyclopentasiloxane, cyclotetrasiloxane, dibenzylidene sorbitol, dicaprylate/dicaprate, diisopropyl adipate, diisopropyl sebacate, dimethicone, dipropylene glycol, L panthenol, farnesol, fragrance, glycerin, glyceryl oleate, glyceryl stearate, hectorite, hydrofluorocarbon 152A, hydrogenated castor oil, hydrogenated polyisobutane, hydrogenated vegetable oil, hydroxyethylcellulose, isobutane, isopropyl alcohol, isopropyl myristate, laureth-4, methylparaben, mineral oil, myristyl myristate, octoxynol-9, octyl isononanoate, octyl palmitate, octyldodecanol, PEG-100 stearate, PEG-20, PEG-25 propylene glycol stearate, PEG-8 distearate, pentadecalactone, petrolatum, PG, phenyl trimethicone, polyethylene, polyol, polysaccharides, polysorbate 20, polythylene, potassium alum, potassium sorbate, PPG-14 butyl ether, PPG-1-PBG-9 lauryl glycol ether, propane, propylene carbonate, propylene glycol, propylparaben, purified clay, quaternium-18, SD alcohol 40, silica, silk powder, sodium bicarbonate, sodium laureth 13 carboxylate, sodium stearate, soyaethyl morpholinium ethosulfate, starch, stearyl alcohol, talc, T-butyl alcohol, T-butyl hydroquinone, tetrasodium EDTA, tribehenin, triclosan, triclosan, triethyl citrate, urea, various coloring agents, various mineral and vitamin extracts, vegetable oil, vegetable starches, water, xanthan gum, zinc oxide.

The present invention provides for novel formulations of anti-perspirant and deodorant products by incorporating bioactive glass into a combination of any of the above-listed ingredients.

The antimicrobial, anti-inflammatory, and hygroscopic effects of bioactive glass are particularly useful in anti-perspirant and deodorant products to reduce bacteria, odor and moisture.

Aftershave and Shaving Lotion Products

The present invention includes novel formulations which incorporate bioactive glass into various brands of aftershave and shaving lotion products such as the products marketed under the brand names Aceite, Afta, Aqua Velva, Aspen, Brut, Bump Fighter, Burt's Bees, Earth Science, Edge, Flents, Gillette, Hoyt Co., Ice Sport, Iodex, Jason, Jovan, Mennen, Old Spice, Pinaud, Pomada, Requa, Samborns, Saxon, Skin Bracer, Super Macho, Williams, and products produced by high-end and generic manufacturers.

Aftershave and shaving lotion formulations which include bioactive glass provide excellent anti-inflammatory effects to reduce post-shaving irritation.

Generally, aftershave and shaving lotion products comprise propylene glycol, menthol and benzoic acid.

Common formulations of aftershave and shaving lotion products comprise SD alcohol 40, water, glycerin, menthol, fragrance, benzophenone-1 and various coloring agents.

Aftershave and shaving lotion products may also include one or more of the following: aloe extract, aluminum starch octenylsuccinate, benzoic acid, benzyl alcohol, BHT, C12-15 alkyl benzoate, carbomer 980, cassava flour, cyclomethicone, dimethicone, disodium EDTA, ethylenediamine, isodecyl oleate, isopropyl myristate, methylparaben, myristyl propionate, panthenol, PEG/PPG-17/6 copolymer, PEG-60 hydrogenated castor oil, PG, phenoxyethanol, polysorbate 80, PPG-15, propylene glycol, SD alcohol 39-C, stearyl ether, tetrahydroxypropyl, tocopheryl acetate, triethanolamine, various plant, fruit, and vitamin extracts, xanthan gum, propylene glycol, benzoic acid, benzophenone-2, BHT, PG, and benzyl alcohol.

The present invention provides for novel formulations of aftershave and shaving lotion products by incorporating bioactive glass into a combination of any of the above-listed ingredients.

The anti-inflammatory effects of bioactive glass are particularly useful in aftershave and shaving lotion products to reduce inflammation.

Shaving Products

The present invention includes novel formulations which incorporate bioactive glass into various brands of shaving products in creme, gel, powder and soap form such as the products marketed under the brand names Afta, Alba Botanica, Aveeno, Barbasol, Brut, Bump Stopper, Burma-Shave, Burt's Bees, CAM, Colgate, Earth Science, Edge, Everready, Gillette, Jason, Kiss My Face, Lady Legs, Magic Platinum, Magic Shaving Powder, Noxzema, Old Spice, Palmolive, Pinaud, Remington, Requa, Rise, Shave in the Shower, Skin Bracer, Skinmate, Skintimates, Soft Shave, Tom's of Maine, Williams, and products produced by high-end and generic manufacturers.

Generally, shaving products in cream gel, powder, or soap form comprise a moisturizer such as aloe gel and a protectant such as stearic acid.

Common formulations of shaving products cream gel, powder, or soap powder comprise water, triethanolamine, palmitic acid, stearic acid, isopentane, monoglycerides, sorbitol, PEG-90M, PVP, fragrance, isobutane, various coloring agents, and various floral, vitamin, and mineral extracts.

Shaving products in cream gel, powder, or soap form may also include one or more of the following: 1-dodecanol, allantoin, aloe extract, aluminum starch octenylsuccinate, ammonium hydroxide, barium sulfide, behentrimonium methosulfate, benzaldehyde, benzophenone-1, benzyl alcohol, BHA, BHT, bromelain, butane, C16 to C22, calcium carbonate, calcium hydroxide, calcium thioglycolate, carbomer, cellulose polymer, cetearyl alcohol, cetyl alcohol, chlorhexidine gluconate, corn starch, diazolidinyl urea, dimethicone, dimethyl sulfate quaternized, dioctyl succinate, esters with triethanolamine, fatty acid esters, glycerides, glycerin, glyceryl oleate, glyceryl stearate, guanidine carbonate, hydroxyethycellulose, isopropyl myristate, isopropyl palmitate, lanolin alcohol, lanolin oil, laureth-23, lecithin, menthol, methylparaben, milk protein, myristyl propionate, nonoxynol 10, oxidized polyethylene, paraffin, PEG 14M, PEG 150 pentaerythrityl tetrastearate, PEG 6 caprylic/capric glycerides, pentane, pentasodium pentetate, petrolatum, phenycarbinol, polyethylene, polyquaternium 10, polysorbate 20, polysorbate 60, potassium myristate, PPG-12-PEG-65, propane, propyl gallate, propylene glycol, propylparaben, resorcin, retinyl palmitate, SD alcohol 40, soap, sodium benzoate, sodium borate, sodium chloride, sodium lauryl sulfate, sodium metasilicate, sodium myristate, stearyl alcohol, TEA stearate, teamaleate, tetrasodium etibronate, titanium dioxide, tocopheryl acetate, triclosan, isobutane, cyclomethicone, and C12-15 alkyl benzoate.

The present invention provides for novel formulations of shaving cream and gel products by incorporating bioactive glass into a combination of any of the above-listed ingredients.

The antimicrobial effects of bioactive glass are particularly useful in shaving products to reduce bacteria and the possibility of infection from nicks and cuts inflicted during shaving.

Depilatory and Hair Bleaching Products

The present invention includes novel formulations which incorporate bioactive glass into various brands of depilatory, epilatory and hair bleaching products in cream, wax, and powder form such as the products marketed under the brand names Andrea, Ardell, Better-Off, Bikini Bare, Hair Off, Jolen, Nair, Natural, Neet, Nudit, One Touch, Sally Hanson, Zip, and products produced by high-end and generic manufacturers.

Generally, depilatory, epilatory, and hair bleaching products comprise the active ingredient calcium thioglycolate or calcium hydroxide.

Common formulations of depilatory, epilatory or hair bleaching products comprise water, mineral oil, calcium hydroxide, cetearyl alcohol, calcium thioglycolate, sodium thioglycolate, ceteareth-20, various floral and herbal, and vitamin extracts, and various coloring agents.

Depilatory, epilatory and hair bleaching products may also include one or more of the following: ammonium bicarbonate, benzalkonium chloride, camphor, cetyl alcohol, chamomile extract, citric acid, dimethicone, fragrance, glyceryl stearate, hydrogen peroxide, iron oxides, isopropyl myristate, isopropyl palmitate, isopropyl stearate, maltodextrin, octoxynol-9, pentaerythrityl tetracaprylate/caprate, petrolatum, phosphoric acid, potassium sorbate, SD alcohol 40, stearamidopropyl dimethylamine, stearyl stearate, sweet almond oil, calcium glyceryl stearate, octyl palmitate, stearic acid, propylene glycol, triethanolamine, imidazolidinyl urea, PEG-100 stearate, soluble collagen, lanolin alcohol, disodium EDTA, carbomer, methylparaben, thioglycolate, stearyl alcohol, and silica.

The present invention provides for novel formulations of depilatory, epilatory, and wax products by incorporating bioactive glass into a combination of any of the above-listed ingredients.

The anti-inflammatory and anti-microbial effects of bioactive glass are particularly useful in depilatory, epilatory, and wax products to reduce inflammation, bacteria, and odor.

Toothpaste Products

Bioactive glass may also be incorporated into various brands of toothpaste products such as the products marketed under the brand names Act, Aim, Aquafresh, Arm & Hammer, Biore, Biotene, Boiron, Breath Remedy, Brite-Life, Butler, Cepacol, Close-Up, Colgate, Crest, Dentu-Creme, Desert Essence, Enamelon, Fixodent, Fresh 'N Brite, Gel-Kam, Gleem, Interplak, Keep, Kids Dental Kare, Listerine, Mentadent, Natural White, Nature's Gate, Orajel, Oral-B, Pearl Drops, Pepsodent, Plak Smacker, Plus+White, Pollident, Q-Dent, Rembrandt, Sensodyne, Thermodent, Tom's of Maine, Topol, Ultra Brite, Ultra Plus, Vademecum, Viadent, and products produced by high-end and generic manufacturers.

Generally, toothpaste products comprise fluoride, triclosan, pyrophosphates, silica, baking soda, potassium nitrate and natural and/or artificial flavoring.

Common formulations of toothpaste products comprise sodium fluoride, water, sorbitol, hydrated silica, zinc citrate trihydrate, sodium lauryl sulfate, SD alcohol 38-B, flavor, cellulose gum, sodium saccharin, and various coloring agents.

Toothpaste products may also include one or more of the following: acesulfame potassium, alumina, ammonium chloride, beta-d-glucose, calcium peroxide, calcium sulfate, carbomer, carboxymethylcellulose, citric acid, coenzyme Q10, dicalcium phosphate dihydrate, glycerin, hydrogen peroxide, lactoperoxidase, glucose oxidase, lysozyme, magnesium chloride, methylparaben, microdent poloxamer, monoammonium phosphate, papain, PEG 300, PEG 60, hydrogenated castor oil, PEG-12, PEG-32, PEG-6, PEG-75, phosphoric acid, poloxamer 407, poloxapol 1220, Potassium Nitrate, potassium sorbate, potassium thiocyanate, propylene glycol, propylparaben, pyrophosphate, SD alcohol 38-B, silica, simethicone, sodium benzoate, sodium bicarbonate, sodium carbonate, sodium carrageenan, sodium chloride, sodium citrate, sorbitol and related polyols, sodium hydroxide, sodium lauroyl sarcosinate, sodium monofluorophosphate, sodium monofluurophosphate, sodium percarbonate, sodium phosphate, sodium tripolyphosphate, tetrapotassium pyrophosphate, tetrasodium pyrophosphate, titanium dioxide, trisodium phosphate, PEG-8, various natural and artificial flavorings, xanthan gum, zinc chloride, zirconium silicate, thymol, methyl salicylate, and benzoic acid.

Bioactive glass compositions are useful in, for example, enamel remiralization, incipient caries remineralization, carious dentin remineralization, caries prevention, arresting decay, reversing decay, anti-caries, pit and fissure sealants, prophylactic pastes, fluoride treatments, dentinal sealants, etc. Bioactive glass may be included in toothpastes, liners, bases, gels, and restorative material e.g., packing, indirect pulp capping agent, etc. Such compositions are also useful in the treatment of surfaces after periodontal surgery to decrease dentinal sensitivity and enhance tissue attachment. These compositions are active in treating various defects associated with a variety of dental and other conditions and actually chemically and physically bond to the tooth thereby remineralizing tooth structure.

As referred to herein, remineralization is the formation of hydroxyapatite. The formation of hydroxyapatite begins with exposure of a bioactive glass composition to aqueous solutions. It is believed that the sodium ions (Na+) in the bioactive glass exchanges with H+ ions in body fluids causing pH to increase. Calcium and phosphorus then migrate from the bioactive glass forming a calcium-phosphorous rich surface layer. An underlying silica rich zone slowly increases as the sodium ion in the bioactive glass continues to exchange with the hydrogen ion of the solution. After time, the calcium-phosphorous rich layer crystallizes into a hydroxyapatite material. Collagen can become structurally integrated with the apatite agglomerates. An effective remineralizing amount refers to any amount capable of forming hydroxyapatite.

As the term "a tooth structure" is used herein, it is intended to refer to any feature or features of a tooth including but not limited to enamel, dentin, pulp, tooth root structure, cementum, root dentin, coronal dentin, any dental manufacture, etc.

For example, the following composition by weight will provide a bioactive glass suitable for toothpaste and mouthwash formulations:

| Component | Percent |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5 |

Such bioactive glasses provide an efficacious material for interaction with the tooth structure and do not trigger an overwhelmingly adverse immune response.

Bioactive glasses of specified particle sizes are particularly useful in toothpaste and mouthwash formulations especially when small and very small particles are combined. For example, when compositions including small particles that are capable of bonding with tooth structure (e.g., less than about 90 microns) as well smaller particles (e.g., less than about 10) are used in combination, the larger of these particles adhere to tooth structure and act as ionic reservoirs while the smaller are capable of entering and lodging inside of various tooth structure surface irregularities. The larger of these particles provide a reservoir of additional calcium and phosphorous so that the mineralization, or depositing of the calcium phosphate layer begun by the small particles can continue. Additional calcium and phosphorous can be leached to all tooth structure as well as to particles which have become attached to the inside or at the openings of surface irregularities of tooth structure such as dentinal tubules. This in turn provides for continuation of the entire reaction and continued growth of the smaller of these particles which have lodged inside or over the openings of such surface irregularities and can result in effectively coating or filling the surface irregularity. This excess concentration of ions of calcium and phosphorous is necessary for continued reaction of the smaller of these particles to take place because the smaller particles quickly exhaust their ions as a result of their relatively high surface area. The larger of these particles will react and release their ions more slowly as a longer term effect. Furthermore, the larger of these particles will mechanically abrade the tooth surface opening various surface irregularities allowing small particles to enter and react with the surface irregularity.

This effect is very beneficial in a variety of applications. For example, in preventing caries or decay, the composition of the present invention is capable of penetrating into the depths of the smallest of surface irregularities and receiving a continued supply of ions from larger nearby particles so that it is able to grow after exhausting its stored ion supply. This is also very useful in sealing pits and fissures and a much more effective and long lasting seal is obtained.

For some applications extremely small particles are used. For example, particles that are in the range of 2 microns are used to fit inside dentin tubules that are approximately 1-2 microns in diameter. The occlusion of these tubules leads to a significant reduction in the amount of sensitivity after, for example, periodontal surgery. A particularly effective combination includes a mixture of particles, wherein the mixture comprises particles less than 2 microns and particles more than 45 microns.

Theses bioactive glass compositions generally do not require time to set and are not easily washed away by mechanical abrasion caused by brushing, exposure to mild acids in food, salivary flow or other liquids which normally come in contact with the teeth. Such compositions can generally withstand significant agitation, rinsing with water and long term soaking in simulated saliva for five days. Moreover, many of the small particles do not require a set time because they begin to chemically react and adhere to tooth structure as soon as they come into contact with these surfaces and fluids naturally present in the mouth. Although such compositions are effective with a single application, it is likely that multiple applications will be more efficacious.

As previously noted, relatively small particulate bioactive glass does not generate a significant immune response. Moreover, it is generally not engulfed by macrophages and rendered inactive.

In addition, these bioactive glass compositions are capable of providing a bioactive layer that will form a new structural layer which is a lasting remineralization of tooth structure. This has been verified by the reformation of a hydroxycarbonate apatite layer on dentin surfaces after treatment with bioactive glass compositions with Fourier Transform Infrared spectroscopy (FTIR).

Such bioactive glass compositions may comprise particles having a particle size of about 20 microns with about 30 percent of the particles less than 10 microns. Other formulations may comprise bioactive glass particles have an average particle size of 10 microns with at least 25% smaller than 2 microns.

These compositions may be formulated into toothpaste. In fact, the particles may replace the silica currently used in toothpastes. The addition of fluoride in the glass composition will enhance and strengthen the tooth structure. In addition to direct application of the bioactive glass to the teeth, these bioactive glass compositions may also be applied in a saline or distilled water based medium. These compositions may also be formulated into mouthwash, gel or they may be applied by a dentist as a paste.

These compositions can be used in methods for whitening, lightening or bleaching teeth. These methods are also useful for removing stains from teeth. These methods include contacting teeth with an effective tooth-whitening amount of bioactive glass, especially methods using multiple applications. Each application may include between about 0.02 to 0.3 grams of bioactive glass. Suitably, these methods of whitening teeth comprise contacting the teeth with an effective tooth-whitening amount of bioactive glass twice daily for two weeks or more. "Tooth-whitening amount" generally refers to any amount that will result in a Vita shade guide lightening of one or more shades in a patient with a pre-treatment shade darker than A3.5 after 4 weeks of application twice daily for two minutes or more per application.

Methods for whitening teeth may also comprise contacting teeth with an effective tooth-whitening amount of particulate bioactive and biocompatible glass comprising silicon oxide or hydroxide and optionally one or more elements such as Na, K, Ca, Mg, B, Ti, Al, P, N or F.

Such bioactive glass compositions usually comprises at least Na, Ca and P, although it is possible to use simple sodium silica glasses together with external sources of calcium and phosphate. An external source of calcium and phosphate may be from saliva itself, or may be formulated into the oral hygiene composition.

The addition of fluoride in bioactive glass compositions enhances and strengthens the tooth structure. Other examples include sol gel glasses having, for example, about 40 to about 86% by weight $SiO_2$, substantially no amount of sodium, about 6-36% by weight Ca and about 2-12% by weight $P_2O_5$.

Bioactive glass compositions comprising extremely small particles may also be used. For example, particles that are in the range of 2 microns are beneficial. Particle size may be determined by scanning electron microscopy or laser light scattering techniques (e.g., Coulter LS100). As stated previously, relatively small bioactive particulate glass does not generate a significant immune response. Moreover, it is generally not engulfed by macrophages and rendered inactive.

These compositions may be formulated as oral hygiene compositions such as dentifrice's, toothpaste, gels, powders, mouthwashes, irrigating solutions, and presentations for sucking or chewing such as gums, pastilles, tablets, and lozenges. Such oral hygiene compositions may comprise between 0.1 to 50% by weight. Formulations comprising 1 to 25% by weight are preferable, while formulations comprising 5 to 10% by weight of the bioactive glass are even more preferable.

In addition to the active ingredients, suitable oral hygiene compositions may contain the usual carriers, binders, surfactants, humectants, coloring agents, pigments, antiplaque agents, anti-bacterial agents, bioadhesive-type agents, abrasives, anticaries agents, flavorings, sweeteners, bulking agents, and the like.

In the case of a toothpaste formulation, an abrasive typically includes amorphous, gelled, precipitated, or fumed silica, plastics particles, alumina, calcium carbonate, and zinc orthophosphate, insoluble metaphosphates and calcium pyrophosphate. Silica is an especially suitable abrasive. The bioactive glass particles may replace all, some, or none of the abrasive currently used in toothpastes.

Inorganic thickeners may be included in the dentifrice's and further include fumed silicas such as Cabosil available from Cabot Corporation, and thickening silicas including those available from J. M. Huber designated Zeodent 165. Organic thickeners such as natural and synthetic gums and colloids may also be incorporated in dentifrice compositions. Examples of such thickeners include carrageenan (Irish moss), xanthan gum and sodium carboxymethyl cellulose, starch, polyvinlpyrrolidone, hydroxyethyl propyl cellulose, hydroxbutyl methyl cellulose, hydroxypropyl methyl cellulose, and hydroxyethyl cellulose (co-dried blends of microcrystalline celluloselcellulose gum). The inorganic or organic thickener may be incorporated in such compositions at a concentration of about 0.05 to about 2% by weight and preferably about 0.1 to about 1.5% by weight.

Fluoride-providing salts having anti-caries efficacy may also be incorporated in the oral compositions and are characterized by their ability to release fluoride ions in water. It is preferable to employ a water-soluble salt fluoride providing about 10 to 5,000 ppm of fluoride ion and preferably about 1000 to 1500 ppm of fluoride ion. Among these materials are water-soluble alkali metal salts, for example, sodium fluoride, potassium fluoride, sodium monofluorophosphate and sodium fluorosilicate. Sodium monofluorophosphate is a preferred fluoride-providing salt.

Pigments may include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C Yellow #15 lake. The pigments have a particle size in the range of 5-1000 microns, preferably 250-500 microns, and are present at a concentration of 0.5 to 3% by weight. Dyes are generally sensitive to the presence of the peroxide ingredient and are not included in the dentifrice although FD&C Green #3 has been found to be resistant to fading when $CaO_2$ is present in the dentifrice.

Any suitable flavoring or sweetening material may be employed. Examples of suitable flavoring ingredients are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into these oral compositions. For example, preservatives, silicones and chlorophyll compounds, vitamins such as vitamins B6, B12, C, E and K, antibacterial agents such as chlorhexidine, halogenated diphenyl ethers such as triclosan, desensitizing agents such as potassium nitrate and potassium citrate and mixtures thereof may be included. These adjuvants are incorporated in the dentifrice in amounts which do not substantially adversely affect the properties and characteristics desired, and are selected and used in proper amounts, depending upon the particular type of component involved.

The making of gels, toothpastes, rinses, mouthwashes, gums, and chewing gums are well known in the art. Bioactive glasses can be introduced into these products by a variety of methods including simple mixing. In some circumstances it will be necessary to keep the bioactive glass from coming into contact with the aqueous or other components of the delivery vehicle to prevent the bioactive glass from pre-reacting. This can be accomplished in a number of ways including, for example, two piece syringes with a mixing chamber.

Mouthwash and Mouth Rinse Products

The present invention includes novel formulations which incorporate bioactive glass into various brands of mouthwash and mouth rinse products such as the products marketed under the brand names Act, Doctor Tichenor, Glyoxide Antiseptic, Betadine, Biotene, Cepacol, Colgate, Good Sense, Lavoris, Listerine, Listermint, Plax, Reach, Rembrandt, Salivart, Scope, Signal, Targon, Tom's of Maine, Viadent, Vince, Weleda, and products produced by high-end and generic manufacturers.

Generally, mouthwash and mouth rinse products comprise fluoride, antibacterial agents, hydrogen peroxide and sodium carbonate.

Common formulations of mouthwash and mouth rinse products comprise thymol, eucaluptol, methyl salicylate menthol, water, alcohol, benzoic acid, poloxamer 407, sodium benzoate, and caramel.

Mouthwash and mouth rinse products may also include one or more of the following: aloe vera, calcium chloride, calcium lactate, cetylpyridinium chloride, citric acid, domiphen bromide, glucono delta lactone, glucose oxidase, glycerin, hydrogenated starch, hydroxyethylcellulose, lactoferrin, lactoperoxidase, lysozyme, magnesium chloride, methylparaben, natural and artificial flavorings, nitrogen, poloxamer 237, polysorbate 20, polysorbate 80, potassium chloride, potassium phosphate, povidone-iodine, propylene glycol, saccharin, saccharin sodium, SD alcohol 38-B, sodium carboxymethylcellolose, sodium chloride, sodium citrate, sodium gluconate, sodium hydroxide, sodium lauryl sulfate, sodium saccharin, sorbitol, sodium pyrophosphate, various natural and artificial flavorings, xanthan gum, xylitol, zinc chloride and zinc oxide.

The present invention provides for novel formulations of mouthwash and mouth rinse products by incorporating bioactive glass into a combination of any of the above-listed ingredients.

In addition to direct application of the bioactive glass to the teeth, these bioactive glass compositions can also be applied in a saline or distilled water based medium.

These oral formulations may be used together with a source of calcium and/or phosphate in the manufacture of a composition for whitening teeth.

The antimicrobial and abrasive effects of bioactive glass are particularly useful in mouthwash and mouth rinse products to reduce bacteria and to remove stains.

Eye Drop Products

The present invention includes novel formulations which incorporate bioactive glass into various brands of eye drop products such as the product's marketed under the brand names Medic's Choice, Alcon, All Clear, Baush & Lomb, Bio, Tears Naturale, Clear Eyes, Murine Plus, Naphcon, OcuClear, Opcon-A, Prefrin, Vasoclear, Visine, and products produced by high-end and generic manufacturers.

Generally, eye drop products comprise polyethylene glycol 300, naphazoline hydrochloride and benzalkonium chloride.

Eyedrop products may also include one of the following: boric acid, edetate disodium, water, sodium borate, polyvinyl alcohol, povidone, tetrahydrozoline hydrochloride, dextrose, disodium EDTA, potassium chloride, water, sodium bicarbonate, sodium chloride, sodium citrate, sodium phosphate, oxymetazoline HCl, hydroxpropyl methyl cellulose, pheniramine maleate, liquifilm, phenylephrine HCl, sodium acetate, sodium thiosulfate and hydrochloric acid.

The present invention provides for novel formulations of eye drop products by incorporating bioactive glass into a combination of any of the above-listed ingredients.

Contact Lens Treatment Products

Bioactive glass may also be incorporated into various brands of contact lens treatment products, including cleaning solutions for hard and soft lens, saline solutions, and rewetting solutions, such as the products marketed under the brand names Alcon, Allergan, Barnes Hind, Bausch & Lomb, Boston, Ciba, Clean-N-Soak, Clerz Z, Liquifilm, Opti-Soak, ProFree, Resolve, Soac-Lens, Wet-N-Soak, Alcon, Allergan, Ciba Vision, Complete, Lens Plus, Miraflow, Opti-Clean, Opti-Free, Opti-Zyme, Pliagel, ReNu, Sensitive Eyes, Ultra Zyme, drugstore.com, Softwear, Unisol, Clear Eyes, Clerz Z, Opti-One, and products produced by high-end and generic manufacturers.

Generally, contact lens treatment products comprise boric acid, sodium chloride, thimersol, and edetate disodium.

Contact lens treatment products may also include one or more of the following: benzalkonium chloride, alkyl ether sulfate, ethoxylated alkyl phenol, tri-quaternary cocoa-based phospholipid, silica gel, titanium dioxide, fragrance, phenylmercuric nitrate, polyvinyl alcohol, anionic detergents, sodium phosphates, polysorbate 80, hydroxyethyl cellulose, polyquad, papain, cocoamphocarboxyglycinate, sodium lauryl sulfate, hexylene glycol, pancreatin, tyloxapol, sorbic acid, subitilisin A, poloxame 407, amphoteric 10, tween 21 stabilizer, microclens, potassium chloride, proteolytic enzyme, sodium carbonate, poloxamine, sodium borate, isotonic saline, antimicrobial buffer system, sodium perborate, hydrogen peroxide, phosphonic acid, nitrogen, borate buffer system, water, EDTA, caramide, glycerin, and povidine.

In addition, bioactive glass may be added to or included in ear drops and nose drops to provide or enhance antibacterial, anti-inflammatory, and hygroscopic effects.

Bioactive glass also may be added to or incorporated into nail files, e.g., fingernail and toenail files. The anti-inflammatory properties of bioactive glass make it particularly well-suited for use with such nail care devices.

In addition, bioactive glass may be used with men's or women's shaving devices, including but not limited to disposable and electric razors. The antibacterial and anti-inflammatory properties of bioactive glass make it well-suited for use in such products.

Bioactive glass may also be added to or included in oral care products such as Ambisol. The anti-inflammatory and antimicrobial properties of bioactive glass can be beneficial in such products.

Example 14 below provides exemplary embodiments of additional prototype cosmetic formulations incorporating bioactiv glass, including sol-gel-derived bioactive glass.

EXAMPLE 14

Additional Protype Cosmetic Formulations

Several prototype cosmetic products comprising bioactive glass were developed as follows.

1. A soft focus cosmetic product was developed and comprised a sol-gel-derived bioactive glass powder mixed with a commercially available facial cream. This product gave the appearance of wrinkle reduction and skin-tightening when applied to the face.

2. A shampoo product, containing 5 wt % of 4 µm bioactive glass formulated in a combination of Standapol ES-2, Crosultaine C-50, Foamid C, deionized $H_2O$, Phenobact and citric acid.

3. A nail-hardening/protecting gel, containing gelled jojoba oil or glycerin and a Pemulen® polymer, or glycerin, water, citric acid, Jaguar C-14S and phenobact.

4. Makeup formulas, containing gelled jojoba oil and with Lubrajel® MS with various pigments 5. A skin lotion/makeup, containing Polawax, mineral oil, glycerin, Jaguar C14-S, citric acid, Phenobact, colorant and fragrance 6. A sunscreen product, containing gelled jojoba oil, octyl methoxycinnamate and benzophenone-3

7. A deodorant stick containing 8% bioactive glass and composition MV00/036/02/01

8. A deodorant stick containing 8% bioactive glass and composition MV00/036/01/01

9. A deodorant stick containing 5% bioactive glass and composition MV00/030/02/01

10. A deodorant cream containing 50% bioactive glass and composition MV00/036/03/01

11. A nail hardening creme containing 15% bioactive glass and composition MV00/036/04/01A.

12. A nail hardening creme containing 30% bioactive glass and composition MV00/036/04/01B Example 15 below demonstrates that the cosmetic formulations comprising bioactive glass, including sol-gel-derived bioactive glass, do not irritate the skin or result in any perceivable allergic hypesensitivity.

EXAMPLE 15

Skin Sensitivity Tests

Several prototype products (Bioglass (30% utl.) in an O/W-Formulation) were tested to determine if skin irritation or allergic hypersensitivity was present following the use of any of the protypte cosmetic compositions comprising bioactive glass.

Patch testing represents a sound, relatively safe and reasonable reliable method for identifying allergens. A positive reaction to a correctly applied patch-test proves that the person has a contact sensitivity to the substance tested, but not necessarily that the substance is the cause of the clinical dermatitis.

In patch testing, the suspected topical allergen has to penetrate the stratum corneum to the viable (effector) cells of the skin to present a local challenge to the immune system.

Methods: The product to be tested is applied on a patch of filter paper, placed on an impermeable sheet and fixed to the skin with adhesive tape (Leukotest (R), Fa. Hartmann). Test site: inner side of the forearm. The test patch is left in place for 24 hours then removed. The examination by the dermatologist followes. A second and third examination are performed after 48 and 72 hours by the dermatologist.

All assessments were performed under standard lighting conditions by the responsible dermatologist.

Panellists were instructed to keep the test sites dry over the application period.

Results: Under the conditions of this test no evidence of primary irritation or allergic hypersensitivity was present. None of the thirty patch-tests resulted in positive reactions after 24, 48 and 72 hours. The tested products are considered safe for use.

Examples 16 and 17 below provide the results of inhibition zone tests and demonstrates the anti-microbial effects of bioactive glass. The anti-microbial effects of bioactive glass are useful in many of the cosmetic formulations described above.

EXAMPLE 16

Inhibition Zone Test

Liquid Caso agar or Sabouraud agar was mixed with the corresponding test organism (target: $10^5$ CFU/plate) and poured into petri dishes. After the agar had cooled, a disk (approx. 1 cm in diameter) was punched out of the agar and was filled with approximately 0.5 g 45S (Bioglass™) bioactive glass powder. The agar was stored for 2 hours at 5° C. and subsequently incubated. After completion of the incubation period (1-5 days), the samples were checked for inhibition zone formation and growth.

The test organisms used were:
*Bacillus subtilis* ATCC 6633
*Staphylococcus aureus* ATCC 6538
*Pseudomonas aeruginosa* ATCC 9027
*Candida albicans* ATCC 10231
*Aspergillus niger* ATCC 16404

Results:
Size of inhibition zone in mm per sample batch

|  | Batch No. | | |
|---|---|---|---|
| Test organism | 1 | 2 | 3 |
| *Bacillus subtilis* | | | |
| 1 day | 5 | 5 | 3 |
| 2 days | 2 | 2 | 1 |
| 3 days | 2 | 1 | 1 |
| 5 days | 2 | 0 | 0 |
| *Staphylococcus aureus* | | | |
| 1 day | 4 | 4 | 4 |
| 2 days | 3 | 3 | 2 |
| 3 days | 3 | 3 | 2 |
| 5 days | 3 | 2 | 2 |
| *Pseudomonas aeruginosa* | | | |
| 1 day | 4 | 4 | 3 |
| 2 days | 2 | 2 | 1 |
| 3 days | 2 | 2 | 0 |
| 5 days | 2 | 0 | 0 |
| *Candida albicans* | | | |
| 1 day | 3 | 3 | 3 |
| 2 days | 0 | 1 | 1 |
| 3 days | 0 | 0 | 0 |
| 5 days | 0 | 0 | 0 |
| *Aspergillus niger* | | | |
| 1 day | 5 | 5 | 5 |
| 2 days | 5 | 5 | 4 |
| 3 days | 3 | 3 | 2 |
| 5 days | 2 | 2 | 0 | pH controls on nutrient media without seeding with microorganisms, but in the presence of the sample resulted in the following:

| on glass powder: | pH >= 10 |
|---|---|
| on agar near glass powder | pH 9.5 |
| on agar (periphery): | pH 8.5 |
| (control plate without glass powder: pH 7.5) | |

EXAMPLE 17

Concentration Dependent Inhibition Test

Liquid Caso agar or Sabouraud agar was mixed with the corresponding test organism (target: $10^5$ CFU/plate) as well as variable amounts (see chart below) of 45S bioactive glass powder and poured into petri dishes. The agar was stored for 2 hours at 5° C. and subsequently incubated. After completion of the incubation period (1-5 days) the samples were checked for inhibition zone formation and growth.

The test organisms used were:

*Bacillus subtilis* ATCC 6633
*Staphylococcus aureus* ATCC 6538
*Pseudomonas aeruginosa* ATCC 9027
*Candida albicans* ATCC 10231
*Aspergillus niger* ATCC 16404

Results: Organism count using different amounts of glass powder

|  | Content of glass in mg | | | | |
|---|---|---|---|---|---|
| Test organism | 10 | 100 | 200 | 500 | 1000 |
| *Bacillus subtilis* | | | | | |
| 1 day | >$10^5$ | >$10^5$ | >$10^4$ | 0 | 0 |
| 2 days | >$10^5$ | >$10^5$ | >$10^4$ | 0 | 0 |
| 3 days | >$10^5$ | >$10^5$ | >$10^4$ | 0 | 0 |
| 5 days | >$10^5$ | >$10^5$ | + | − | − |
| *Staphylococcus aureus* | | | | | |
| 1 day | >$10^5$ | >$10^5$ | >$10^4$ | 0 | 0 |
| 2 days | >$10^5$ | >$10^5$ | >$10^4$ | 0 | 0 |
| 3 days | >$10^5$ | >$10^5$ | >$10^4$ | 0 | 0 |
| 5 days | >$10^5$ | >$10^5$ | + | − | − |
| *Pseudomonas aeruginosa* | | | | | |
| 1 day | >$10^5$ | >$10^5$ | >$10^4$ | 0 | 0 |
| 2 days | >$10^5$ | >$10^5$ | >$10^4$ | 0 | 0 |
| 3 days | >$10^5$ | >$10^5$ | >$10^4$ | 0 | 0 |
| 5 days | >$10^5$ | >$10^5$ | + | − | − |
| *Candida albicans* | | | | | |
| 1 day | >$10^5$ | >$10^5$ | 0 | 0 | 0 |
| 2 days | >$10^5$ | >$10^5$ | >300 | 0 | 0 |
| 3 days | >$10^5$ | >$10^5$ | >300 | 0 | 0 |
| 5 days | >$10^5$ | >$10^5$ | + | + | + |
| *Aspergillus niger* | | | | | |
| 1 day | n.d. | n.d. | n.d. | n.d. | n.d. |
| 2 days | >$10^5$ | >300 | >30 | 0 | 0 |
| 3 days | >$10^5$ | >300 | >30 | 0 | 0 |
| 5 days | >$10^5$ | + | + | + | + |

+ = growth detectable after subcultivation
− = no growth detectable after subcultivation
n.d. = not performed The antimicrobial effect of bioactive glass could be detected both in the inhibition zone test as shown in Example 16 and as a function of concentration as shown in Example 17.

The reduction in microbial growth correlates with a pH increase in the medium.

Examples 18 and 19 below demonstrate the effect of bioactive glass on a variety of microorganisms.

EXAMPLE 18

Microbiological Test Series

Microbiological test series with individual microorganisms of an aqueous solution of bioactive glass (clear supernatant), O/W emulsion, W/O emulsion each with different concentrations of bioactive glass.

Conditions:
Individual microorganism suspension
With common salt (in the aqueous solution)
pH value unchanged
Non-sterilized aqueous solution
Arrangement:
Overview tables of load test of individual microorganisms
Test formulas V99/020/01/11-19 (aqueous supernatant)
Test formulas V99/020/02/01a-h (O/W emulsion) (a-h=different concentrations BioGlas/none to 0.2% VSM12650)
Test formulas V99/020/02/02a-f (O/W emulsion) (a-f=different concentrations BioGlas/none to 20% VSM12650)
Test formulas V99/020/03/01a-h (W/O emulsion) (a-h=different concentration BioGlas/none to 0.2% VSM 12650)
Test formulas V99/020/03/02a-f (W/O emulsion) (a-f different concentration BioGlas/none to 20% VSM12650)
Load test MB990669-713 (aqueous supernatant)
Load test MB990714-743 (O/W emulsion)
Load test MB990744-773 (W/O emulsion)
Stability test S990029 (for V99/020/02/01h)
Stability test S990046 (for V99/020/02/02e)
Stability test S990030 (for V99/020/03/01h)
Stability test S990047 (for V99/020/03/02e)

Results:

Aqueous Supernatent

Except for *Aspergillus niger*, all load tests show a logical course of the test series. From a concentration of between 3% and 5% of bioactive glass, no growth is detectable even after 6 load cycles. Bioactive glass is most effective against *Staphylococcus aureus*. *Aspergillus niger*, starting from the 4th load cycle, no longer shows any growth inhibition. Bioactive glass is effective against *Aspergillus niger* at higher concentrations up to the 4th load cycle. (Note: this result is not surprising since *Aspergillus niger*, compared to other species, frequently presents a problem with other preservation systems as well.)

O/W Emulsion/W/O Emulsion

Even at lower concentrations of bioactive glass (2%), a clear preservative effect is observed. But here, too, *Aspergillus niger* exhibits the behavior described above.

Stability

S990029=O/W emulsion base V99/020/02/01h=0.2% VSM12650
Normal test: −7° C./40° C.; stable
Extreme test: −14° C./60° C.; separation in 3rd cycle
S990046=O/W emulsion base V99/020/02/02e=20% VSM12650
Normal test: stable
Extreme test: stable
S990030=W/O emulsion base V99/020/03/01h=0.2% VSM12650
Normal test: separation after 3rd cycle
Extreme test: n/a
S990047=W/O emulsion base V99/020/03/02e=20% VSM12650
Separation of emulsion even before the start of the test series.

LOAD TEST with BIOGLAS
*ASPERGILLUS NIGER*
Test Series 3A
V99/020/01/11–V99/020/01/19 Aqueous Solution/Supernatant
V99/020/02/02 O/W Emulsion
V99/020/03/02 W/O Emulsion

| Concentration | Cycle 0 | Cycle 1 | Cycle 2 | Cycle 3 | Cycle 4 | Cycle 5 | Cycle 6 | |
|---|---|---|---|---|---|---|---|---|
| *Aqueous Solution (Supernatant without Sediment) (V99/020/01/11–19)* | | | | | | | | |
| 0.5% | − | +++ | +++ | +++ | +++ | +++ | +++ | Explanation: |
| 0.8% | − | +++ | +++ | +++ | +++ | +++ | +++ | Cycle 0: smear without |
| 1% | − | +++ | +++ | +++ | +++ | +++ | +++ | inoculation |
| 2% | − | +++ | +++ | +++ | +++ | +++ | +++ | Cycles 1–6: inoculated |
| 3% | − | +++ | +++ | +++ | +++ | +++ | +++ | with above species |
| 5% | − | +++ | +++ | − | +++ | +++ | +++ | Concentration in sample |
| 10% | − | +++ | − | − | +++ | +++ | +++ | container: ca. $10^5$ |
| 15% | − | ++ | − | − | +++ | ++ | +++ | |
| 20% | − | − | − | − | +++ | +++ | +++ | |
| *O/W Emulsion (V99/020/02/02)* | | | | | | | | |
| 2% | − | +++ | +++ | + | +++ | ++ | +++ | Explanation: |
| 5% | − | − | − | − | + | − | + | Cycle 0: smear without |
| 10% | − | − | − | − | − | − | − | inoculation |
| 15% | − | − | − | − | ++ | + | ++ | Cycles 1–6: inoculated |
| 20% | − | − | − | − | ++ | + | ++ | with above species |
| Blank test | − | +++ | +++ | +++ | +++ | +++ | +++ | Concentration in sample container: ca. $10^5$ Blank test: without BioGlas |
| *W/O Emulsion (V99/020/03/02)* | | | | | | | | |
| 2% | − | +++ | +++ | +++ | +++ | +++ | +++ | Explanation: |
| 5% | − | +++ | +++ | +++ | +++ | ++ | + | Cycle 0: smear without |
| 10% | − | +++ | − | − | − | − | − | inoculation |
| 15% | − | − | − | − | − | − | + | Cycles 1–6: inoculated |
| 20% | − | − | − | − | − | − | − | with above species |
| Blank test | − | +++ | +++ | +++ | +++ | +++ | +++ | Concentration in sample container: ca $10^5$ Blank test: without BioGlas |

RESULTS OF LOAD TEST with BIOGLAS
*CANDIDA ALBICANS*
Test Series 3B
V99/020/01/11–V99/020/01/19 Aqueous Solution/Supernatant
V99/020/02/02 O/W Emulsion
V99/020/03/02 W/O Emulsion

| Concentration | Cycle 0 | Cycle 1 | Cycle 2 | Cycle 3 | Cycle 4 | Cycle 5 | Cycle 6 | |
|---|---|---|---|---|---|---|---|---|
| *Aqueous Solution (Supernatant without Sediment) (V99/020/01/11–19)* | | | | | | | | |
| 0.5% | − | − | − | ++ | +++ | +++ | +++ | Explanation: |
| 0.8% | − | − | − | + | +++ | +++ | +++ | Cycle 0: smear without |
| 1% | − | − | − | − | +++ | +++ | +++ | inoculation |
| 2% | − | − | − | − | − | ++ | +++ | Cycles 1–6: inoculated |
| 3% | − | − | − | − | − | − | − | with above species |
| 5% | − | − | − | − | − | − | − | Concentration in sample |
| 10% | − | − | − | − | − | − | − | container: ca. $10^6$ |
| 15% | − | − | − | − | − | − | − | |
| 20% | − | − | − | − | − | − | − | |
| *O/W Emulsion (V99/020/02/02)* | | | | | | | | |
| 2% | − | − | − | − | − | − | − | Explanation: |
| 5% | − | − | − | − | − | − | − | Cycle 0: smear without |
| 10% | − | − | − | − | − | − | − | inoculation |
| 15% | − | − | − | − | − | − | − | Cycles 1–6: inoculated |
| 20% | − | − | − | − | − | − | − | with above species |
| Blank test | − | +++ | +++ | +++ | +++ | +++ | +++ | Concentration in sample container: ca. $10^6$ Blank test: without BioGlas |

-continued

RESULTS OF LOAD TEST with BIOGLAS
*CANDIDA ALBICANS*
Test Series 3B
V99/020/01/11–V99/020/01/19 Aqueous Solution/Supernatant
V99/020/02/02 O/W Emulsion
V99/020/03/02 W/O Emulsion

| Concentration | Cycle 0 | Cycle 1 | Cycle 2 | Cycle 3 | Cycle 4 | Cycle 5 | Cycle 6 | |
|---|---|---|---|---|---|---|---|---|
| W/O Emulsion (V99/020/03/02) | | | | | | | | |
| 2% | − | − | − | +++ | +++ | +++ | +++ | Explanation: |
| 5% | − | − | + | − | − | − | − | Cycle 0: smear without |
| 10% | − | − | − | − | − | − | − | inoculation |
| 15% | − | − | − | − | − | − | − | Cycles 1–6: inoculated |
| 20% | − | − | − | − | − | − | − | with above species |
| Blank test | − | +++ | +++ | +++ | +++ | +++ | +++ | Concentration in sample container: ca. $10^6$ |
| | | | | | | | | Blank test: without BioGlas |

LOAD TEST with BIOGLAS
*ESCHERICHIA COLI*
Test Series 3C
V99/020/01/11–V99/020/01/19 Aqueous Solution/Supernatant
V99/020/02/02 O/W Emulsion
V99/020/03/02 W/O Emulsion

| Concentration | Cycle 0 | Cycle 1 | Cycle 2 | Cycle 3 | Cycle 4 | Cycle 5 | Cycle 6 | |
|---|---|---|---|---|---|---|---|---|
| Aqueous Solution (Supernatant without Sediment) (V99/020/01/11–19) | | | | | | | | |
| 0.5% | − | − | + | − | +++ | +++ | +++ | Explanation: |
| 0.8% | − | − | + | − | − | − | − | Cycle 0: smear without |
| 1% | − | − | − | − | − | +++ | +++ | inoculation |
| 2% | − | − | − | − | − | − | +++ | Cycles 1–6: |
| 3% | − | − | − | − | − | − | − | inoculated with above |
| 5% | − | − | − | − | − | − | − | species |
| 10% | − | − | − | − | − | − | − | Concentration in sample |
| 15% | − | − | − | − | − | − | − | container: ca. $10^6$ |
| 20% | − | − | − | − | − | − | − | |
| O/W Emulsion (V99/020/02/02) | | | | | | | | |
| 2% | − | − | − | − | − | − | − | Explanation: |
| 5% | − | − | − | − | − | − | − | Cycle 0: smear without |
| 10% | − | − | − | − | − | (+) | − | inoculation |
| 15% | − | − | − | − | − | − | − | Cycles 1–6: |
| 20% | − | − | − | − | − | − | − | inoculated with above |
| Blank test | − | − | − | − | − | − | − | species |
| | | | | | | | | Concentration in sample container: ca. $10^6$ |
| | | | | | | | | Blank test: without BioGlas |
| W/O Emulsion (V99/020/03/02) | | | | | | | | |
| 2% | − | + | − | (+) | (++) | (++) | − | Explanation: |
| 5% | − | − | − | − | − | − | − | Cycle 0: smear without |
| 10% | − | − | − | − | − | − | − | inoculation |
| 15% | − | − | − | − | − | − | − | Cycles 1–6: |
| 20% | − | − | − | − | − | − | − | inoculated with above |
| Blank test | − | − | − | − | − | − | ++ | species |
| | | | | | | | | Concentration in sample container: ca. $10^6$ |
| | | | | | | | | Blank test: without BioGlas |

(+), (++): contamination with foreign microorganisms

LOAD TEST with BIOGLAS
*PSEUDOMONAS AERUGINOSA*
Test Series 3D
V99/020/01/11–V99/020/01/19 Aqueous Solution/Supernatant
V99/020/02/02 O/W Emulsion
V99/020/03/02 W/O Emulsion

| Concentration | Cycle 0 | Cycle 1 | Cycle 2 | Cycle 3 | Cycle 4 | Cycle 5 | Cycle 6 | |
|---|---|---|---|---|---|---|---|---|
| Aqueous Solution (Supernatant without Sediment) (V99/020/01/11–19) | | | | | | | | |
| 0.5% | – | – | – | – | +++ | +++ | +++ | Explanation: |
| 0.8% | – | – | +++ | +++ | +++ | +++ | +++ | Cycle 0: smear without |
| 1% | – | – | – | – | +++ | +++ | +++ | inoculation |
| 2% | – | – | – | +++ | +++ | +++ | +++ | Cycles 1–6: inoculated |
| 3% | – | – | – | – | +++ | +++ | +++ | with above species |
| 5% | – | – | – | – | – | + | – | Concentration in sample |
| 10% | – | – | – | – | – | – | – | container: ca. $10^6$ |
| 15% | – | – | – | – | – | – | – | |
| 20% | – | – | – | – | – | – | – | |
| O/W Emulsion (V99/020/02/02) | | | | | | | | |
| 2% | – | – | – | – | – | – | – | Explanation: |
| 5% | – | – | – | – | – | – | – | Cycle 0: smear without |
| 10% | – | – | – | – | – | – | – | inoculation |
| 15% | – | – | – | – | – | – | – | Cycles 1–6: inoculated |
| 20% | – | – | – | – | – | – | – | with above species |
| Blank test | – | – | – | – | – | – | – | Concentration in sample |
| | | | | | | | | container: ca. $10^6$ |
| | | | | | | | | Blank test: without BioGlas |
| W/O Emulsion (V99/020/03/02) | | | | | | | | |
| 2% | – | – | – | +++ | +++ | +++ | +++ | Explanation: |
| 5% | – | – | – | – | – | – | – | Cycle 0: smear without |
| 10% | – | – | – | – | – | – | – | inoculation |
| 15% | – | – | – | – | – | – | – | Cycles 1–6: inoculated |
| 20% | – | – | – | – | – | – | – | with above species |
| Blank test | – | – | +++ | +++ | +++ | +++ | +++ | Concentration in sample |
| | | | | | | | | container: ca. $10^6$ |
| | | | | | | | | Blank test: without BioGlas |

EXAMPLE 19

Microbiological Test Series

Microbiological Test Series with individual microorganisms of selected O/W emulsion
(V99/020/04/03 (G4)=new laboratory sample V99/020/06/01)
Conditions:
individual microorganism suspension
pH value changed to values typical in cosmetics (citric acid)
non-sterilized
Arrangement:
overview table of load test of individual microorganisms
overview table of pH adjustment and change over time
test formulas V99/020/06/01a-f
load test MB991000-1034

Results/Conclusions:

Although, microorganism sterility with O/W emulsions is difficult to achieve the first smear (blank) shows sterility except for *E.coli*. In addition, despite selecting a suitable O/W emulsion base this base has its own preservative effect against *E.coli* and *Staphylococcus aureus*.

The results from Example 19 indicate:

1. The pH value of the O/W base increases again in the course of the test series to the values before adjustment with citric acid. The pH value of the sample without bioactive glass remains unchanged.
2. Microorganism growth is clearly inhibited.
3. With hight concentrations even a difficult to control organism such as *Aspergillus niger* is effectively inhibited.
4. High pH value correlates with microorganism inhibition.

Load Test with Bioglas  
Test Series 7A  
*Aspergillus niger/Candida albicans*  
V99/020/06/01 O/W Emulsion (Dragil)  
non-sterile/pH non-adjusted

| Product NE O/W Cream (Dragil) | | | Test Number | Prod. date | Test start | |
|---|---|---|---|---|---|---|
| Cons. No. | Bioglas | | V99/020/06/01 | Oct. 11, 1999 | Oct. 15, 1999 | |
| MB99 | % | Blank | Cycle 1 | Cycle 2 | Cycle 3 | pH Value before start of test |
| | | | *A. niger* $10^6$ CFU/ml | | | |
| 1000 | a) 2 | – | +++ | +++ | +++ | 10.9 |
| 1001 | b) 5 | – | – | – | – | 11.6 |
| 1002 | c) 10 | – | – | – | – | 11.8 |
| 1003 | d) 15 | – | – | – | – | 12.1 |
| 1004 | e) 20 | – | – | – | – | 12.2 |
| 1005 | f) none | – | +++ | +++ | +++ | 7.1 |
| | | | *C. albicans* $10^7$ CFU/ml | | | |
| 1006 | a) 2 | – | – | – | – | 10.9 |
| 1007 | b) 5 | – | – | – | – | 11.6 |
| 1008 | c) 10 | – | – | (+++P) | – | 11.8 |
| 1009 | d) 15 | – | – | – | – | 12.1 |
| 1010 | e) 20 | – | – | – | – | 12.2 |
| 1011 | f) none | – | +++ | +++ | +++ | 7.1 |

Load Test with Bioglas  
Test Series 7B  
*Escherichia coli/Pseudomonas aeruginosa*  
V99/020/06/01 O/W Emulsion (Dragil)  
non-sterile/pH non-adjusted

| Product NE O/W Cream (Dragil) | | | Test Number | Prod. date | Test start | |
|---|---|---|---|---|---|---|
| Cons. No. | Bioglas | | V99/020/06/01 | Oct. 11, 1999 | Oct. 15, 1999 | |
| MB99 | % | Blank | Cycle 1 | Cycle 2 | Cycle 3 | pH Value before start of test |
| | | | *E. coli* $10^7$ CFU/ml | | | |
| 1012 | a) 2 | – | – | – | – | 10.9 |
| 1013 | b) 5 | – | – | – | – | 11.6 |
| 1014 | c) 10 | – | – | – | – | 11.8 |
| 1015 | d) 15 | – | – | – | – | 12.1 |
| 1016 | e) 20 | – | – | – | – | 12.2 |
| 1017 | f) none | – | +++ | +++ | +++ | 7.1 |
| | | | *Ps. aeruginosa* $10^7$ CFU/ml | | | |
| 1018 | a) 2 | – | – | – | – | 10.9 |
| 1019 | b) 5 | – | – | – | – | 11.6 |
| 1020 | c) 10 | – | – | – | – | 11.8 |
| 1021 | d) 15 | – | – | – | – | 12.1 |
| 1022 | e) 20 | – | – | – | – | 12.2 |
| 1023 | f) none | – | +++ | +++ | +++ | 7.1 |

Load Test with Bioglas
Test Series 7C
*Staphylococcus aureus/Escherichia coli* (pH adjusted)
V99/020/06/01 O/W Emulsion (Dragil)
non-sterile/pH non-adjusted

| Product | Test Number | Prod. date | Test start |
|---|---|---|---|
| NE O/W Cream (Dragil) | V99/020/06/01 | Oct. 11, 1999 | Oct. 15, 1999 |

*St. aureus* $10^7$ CFU/ml

| Cons. No. MB99 | Bioglas % | Blank | Cycle 1 | Cycle 2 | Cycle 3 | pH Value before start of test |
|---|---|---|---|---|---|---|
| 1024 | a) 2 | – | – | – | – | 10.9 |
| 1025 | b) 5 | – | – | – | – | 11.6 |
| 1026 | c) 10 | – | – | – | – | 11.8 |
| 1027 | d) 15 | – | – | – | – | 12.1 |
| 1028 | e) 20 | – | – | – | – | 12.2 |
| 1029 | f) none | – | + | + | + | 7.1 |

*E. coli* $10^7$ CFU/ml (control measurement with adjusted pH value)

| Cons. No. MB99 | Bioglas % | Blank | Cycle 1 | Cycle 2 | Cycle 3 | pH Value Nov. 09, 1999 |
|---|---|---|---|---|---|---|
| 1030 | a) 2 | + | +++ | +++ | +++ | 8.5 |
| 1031 | b) 5 | – | – | – | – | 10 |
| 1032 | c) 10 | ++ | – | – | – | 10 |
| 1033 | d) 15 | – | – | – | – | 10 |
| 1034 | e) 20 | – | – | – | – | 10 |

Cleaning Agents

General

The present invention provides novel cleaning agent compositions comprising bioactive glass. The present invention also provides methods of making and using these novel non-toxic cleaning agents.

Particulate bioactive glass and/or aqueous extracts of particulate bioactive glass can be added to standard household cleaning agents as well as industrial cleaning agents. The resulting formulations provide cleaning agents with enhanced cleaning and anti-microbial properties. In addition to the direct anti-microbial effects of bioactive glass, the increased pH resulting from the presence of bioactive glass also enhances cleaning. In addition, bioactive glass has a high affinity for proteinaceous matter, such as blood and food as well as oil and grease. Cleaning agents containing bioactive glass may be used to effectively clean and disinfect surfaces including, but not limited to painted walls, wood furniture, vinyl floors (waxable and nonwax), vitreus china, porcelain enamel, stainless steel, plastic laminate (Formica®), plastic, acrylic, fiberglass, and chrome. These new cleaning agents may also be used to effectively clean textile materials, including but not limited to, rugs woven from wool, various synthetic fibers, and articles of clothing.

A traditional cleaning agent may be, for example, a compound containing one or more surfactants useful for dissolving dirt in a solvent, especially in an aqueous solvent. Surfactants are generally effective in cleaning grease or oily dirt. However, other dirt, such as proteins or dirt containing proteins, e.g., blood, other staining substances such as coffee or tea, as well as invisible dirt, including dirt from microorganisms, cannot be cleaned in this way alone. For this reason a bleaching agent and/or disinfecting agent are usually added to the cleaning formulations, so that the remaining dirt is at least removed to the point that it is no longer visible. Stains are usually removed oxidatively after the grease and pigment dirt is dissolved.

Oxidative removal is generally accomplished, for example, with chlorine-containing chemicals. Chlorine-containing chemicals generally remove only the coloring part of the stain, whereas the other indissoluble substances remain with the basic substance. Because of its high reactivity, the disadvantage of chlorine is that it aggressively attacks colored surfaces or substances such as fabrics changing the color tone or causing the colors to bleed. In addition, chlorine aggressively attacks the substance to be cleaned, especially fabrics, so that their basic structure is destroyed after multiple washings.

Previous attempts to alleviate the oxidizing effect of chlorine involved the use per-acetic acid. Although per-acetic acid has an adequate disinfecting effect, its ability to penetrate porous material is insufficient, which in turn leads to an unsatisfactory sterilization effect. In addition, per-acetic acid has an oxidizing effect, although to a smaller degree. Although the oxidizing effect of per acetic acid may not create a color-destroying bleaching effect, in most cases its disinfecting effect is not sufficient. For this reason is not possible, for example, to remove aerobic spore producers. Furthermore, the use of per-acids results in significant damage to some materials, such as woolens.

Accordingly, a goal of one embodiment of present invention is to produce cleaning agents which are non-toxic, yet provide an antimicrobial effect, while also providing good cleaning qualities.

Since bioactive glass releases $Ca^{2+}$ ions, it was expected that the presence of bioactive glass in an aqueous solution would significantly increase the hardness of the solution. It was therefore expected that calcification would increase resulting in a reduction of cleaning action, so that these glasses would not be suitable for use as washing and cleaning agents. Moreover, it was expected that the abrasive effect of glass particles would result in a mechanical damage of materials, especially in textiles, which would lead to a corrosion of the fabric. Nevertheless, applicants unexpectedly found that a variety of effective cleaning agents could be formulated comprising bioactive glass. Surprisingly, the effectiveness of the washing agent is not hindered by the release of alkaline ions and there is no increase in the hardness of the water or calcification. Also, these novel cleaning agents do not corrode or damage the materials being cleaned, especially textile fabrics, as feared through the addition of the glass particles.

Bioactive glass is well-suited as a glass cleaner since it is "softer" than standard household cleaners and is suitable as a mild abrasive. In addition, the soluble minerals released by bioactive glass strengthens glass. For example, silicon released by bioactive glass is especially helpful in strengthening and protecting glass products by preventing crack propagation. Bioactive glass coats cracks in glass and builds up a protective silicon layer.

The present invention also provides a cleaning agent containing bioactive glass which not only acts as a biocide against viruses and bacteria, but is also gentle on skin and materials, causes no allergic reactions and cleans hard to remove dirt such as set-in proteins. The present invention also provides non-toxic cleaning agents having biocidal and dirt removing properties to be used in conjunction with a solvent having at least one surface active agent.

In one embodiment the cleaning agent is non-toxic and has biocide and dirt-removing features for joint usage with a dissolving agent containing at least a surface active agent and contains bioactive glass particles that release more than 250 μg of alkaline ions per gram of glass particles. In another embodiment the cleaning agent comprises bioactive glass particles which release at least 300 μg of alkaline ions per gram of glass particles.

The glass particles preferably have an average particle size of smaller than 400μm. In another embodiment the glass particles have an average particle size of smaller than 100 μm.

In one embodiment the cleaning agent comprises tenside as a surface active agent. In another embodiment the cleaning agent contains bioactive glass which has components within the following ranges on a % weight basis: 40-60% $SiO_2$; 10-30% CaO; 0-35% $Na_2O$; 2-8% $P_2O_5$, 0-25% $CaF_2$; 0-10% $B_2O_3$; 0-8% $K_2O$; and 0-5% MgO.

In one embodiment the cleaning agent comprises approximately 1-7% of the weight of glass particles in terms of the total weight of cleaning agent. In one embodiment the invention provides a method of making a cleaning agent in which glass particles are added to at least one surface active agent, which release at least 250 μg of alkaline ions per gram of glass particles. In another embodiment the invention provides a method of using a cleaning agent in clean objects such as a variety of surfaces and textile materials. In one embodiment the cleaning agent is a dish-washing agent. In another embodiment the invention provides a method of using a cleaning agent for cleaning in hospitals, clinics, and in the gastronomy industry.

In one embodiment the cleaning agent containing bioactive glass releases more than 250 μg of alkaline ions per gram of glass particles. The glass particles contained in the cleaning agent according to another embodiment of the present invention preferably release more than 300 μg, and especially more than 500 μg of alkaline ions per gram of glass particles. Glass particles that release more than 1 mg of alkaline ions per gram of glass are even more especially preferred.

Such cleaning agents are not only useful for cleaning and sterilizing surfaces and textile materials but also may be used to clean and sterilize surgical instruments. In addition, cleaning agents containing bioactive glass are useful as dish washing agents, especially for use in dish washers. These novel cleaning agents may also be used in for disinfecting and cleaning surfaces and materials in the sanitation, hospital, and gastronomy industries.

Methods of Making

The present invention also provides a method of making cleaning agent compositions comprising bioactive glass. An effective antimicrobial amount of the bioactive glass is added to or included in a cleaning agent formulation. An "effective, antimicrobial amount of bioactive glass" refers to a sufficient amount of bioactive glass having an appropriate particle size to effectively prevent or control microbial contamination. The amount and particle size of bioactive glass to include in a cleaning agent formulation will vary depending on the desired length and degree of purity as well as the anticipated microbial challenge. An "effective antimicrobial amount of bioactive glass" also may refer to a sufficient amount of an aqueous extract of bioactive glass to effectively prevent or control microbial contamination. An effective antimicrobial amount of bioactive glass may also refer to a combination of particulate bioactive glass and aqueous extract of bioactive glass to effectively prevent or control microbial contamination.

Bioactive glass may be added to or included in cleaning agent formulations using, for example, techniques or combinations of techniques such as general mixing with slow medium, moderate, or even vigorous agitation. Sufficient agitation should be provided to achieve relative homogeneity. Preferably, mixing and agitation will avoid excessive aeration and will have a low sheer rate. Other methods or combinations of methods of blending, dispersing, mixing, combining, and/or emulsifying may be utilized. Agitation may be achieved, for example, with devices such as standard mixers. General mixing and blending may be achieved, for example, with an impeller.

Bioactive glass may be added to or included in virtually any known cleaning agent formulation. Applicants anticipate as well that bioactive glass will be suitable for inclusion in any as yet to be developed cleaning agent formulation. In one embodiment the bioactive glass may be particulate. In another embodiment the bioactive glass may be an aqueous solution derived from particulate bioactive glass. In still another embodiment the bioactive glass may be a combination of particulate bioactive glass and an aqueous solution derived from bioactive glass.

In one embodiment the method of making these novel cleaning agents comprises combining a cleaning agent with one or more surfactants and with bioactive glass. The method may also include adding a solvent. In one embodiment the method comprises adding particulate bioactive glass and/or an aqueous extract of bioactive glass. The aqueous solutions of bioactive glass may be dried, for example, by spray drying or by drying in vacuo to provide an antimicrobial composition. The compositions can be incorporated into other antimicrobial solutions or cleaning agents to provide an additional antimicrobial component to the solutions or cleaning agents.

The present invention will be more clearly understood with reference to the following non-limiting examples.

Categories of Cleaners

The present invention will produce novel formulations which incorporate bioactive glass into various brands of cleaning products including: laundry detergents, stain removers, and fabric softening products, dish washing products, air fresheners, deodorizing products, bathroom tissues, facial tissues, paper towels, napkin products, cotton swabs, handiwipes, scouring and sponge products, oven cleaning products, toilet cleaning products, tub and shower cleaning products, carpet cleaning products, all purpose cleaning products, and jewelry and metal cleaning products.

Laundry Detergent, Stain Remover and Fabric Softening Products

The present invention includes novel formulations which incorporate bioactive glass into various brands of varieties of laundry detergent, stain remover, and fabric softening products, such as the products marketed under the brand names Ajax, All, Arm & Hammer, Biz, Bold, Bounce, Carbona, Cheer, Cling Free, Clorox, Dow, Downy, Dreft, Dryel, Era, Fab, Febreze, Fresh Start, Gain, Ivory, K2R, Oxydol, Purex, Rit, Shout, Snuggle, Spray & Wash, Stain Devil, Sun Cuddle, Surf, Thoro, Tide, Ultra, Windfresh, Wisk, Woolite, Z'Out, and products produced by high-end and generic manufacturers.

Generally, laundry detergent, stain remover, and fabric softening products comprise cleaning agents (anionic and nonionic surfactants), enzymes, water softener, dispensing aid (propylene glycol), buffering agents, water, stabilizing agents, soil suspending agents, color-protecting agents, coloring agents and fragrance.

Common formulations of laundry detergent, stain remover, and fabric softening products comprise cleaning agents (anionic an nonionic surfactants), buffering agent, stabilizer, perfume, brightening agents and coloring agents.

Laundry detergent, stain remover, and fabric softening products may also include one or more of the following: sodium hypochlorite, hydrogen peroxide, water softeners (aluminosilicates, sodium carbonate), various processing aids (sodium sulfate), various washer protection agents, various soil suspending agents, cationic surfactants and various preservatives.

The present invention provides for novel formulations of laundry detergent, stain remover, and fabric softening products by incorporating bioactive glass into a combination of any of the above-listed ingredients.

The antimicrobial and pH effects of bioactive glass are particularly useful in laundry detergent products to reduce bacteria and odor and to increase pH.

Dish-Washing Products

The present invention includes novel formulations which incorporate bioactive glass into various brands of dish-washing products such as the products marketed under the brand names Ajax, All, Cascade, Crystal White, Dawn, Dove, Earth Friendly, Easy Off, Electrosol, Extra Plus, Glass Magic, Ivory, Jet Dry, Joy, Palmolive, Sun Light, Surf, and products produced by high-end and generic manufacturers.

Generally, dish-washing products comprise a detergent, an alkaline compound to increase pH, a surfactant and a fragrance.

Common formulations of dish-washing products comprise triclosan, water, ammonium laureth sulfate, lauryl polyglucose, sodium dodecylbenzenesulfonate, SD alcohol 3-A, sodium xylene sulfonate, quaternium-15, lauramide myristamide MEA, fragrance and various coloring agents.

Dish-washing products also may include one or more of the following: chlorine bleach, silicate salts, lauryl polyglucose, DMDM hydantoin, methylchloroisothiazolinone, calcium carbonate, methylisothiazolinone, anionic surfactants, sodium carbonate, trisodium HEDTA, sodium metabisulfite, and various quality control agents.

The present invention provides for novel formulations of dish-washing products by incorporating bioactive glass into a combination of any of the above-listed ingredients.

The antimicrobial and pH effects of bioactive glass are particularly useful in dish-washing products to reduce bacteria and to increase cleaning power.

Air-Freshener and Room Deodorizing Products

The present invention includes novel formulations which incorporate bioactive glass into various brands of air freshener and room deodorizing products such as the products marketed under the brand names Airwick, Arm & Hammer, Clorex, Country Air, Country Rose, Dale, Enoz, Glade, Lemon Fresh, Little Tree, Lysol, Moonlight Bay, One Drop, Pine Closet, Renuzit, Solid Sachet, Wizard, and products produced by and high-end and generic manufacturers.

Common formulations of air freshener and room deodorizing products comprise N-alkyl, dimethyl benzyl ammonium chloride, octyl decyl dimethyl ammonium chloride, dioctyl dimethyl ammonium chloride, and didecyl dimethyl ammonium chloride.

Air freshener and room deodorizing products also may include one or more of the following: alkyl methyl benzyl ammonium saccharinate and ethanol.

The present invention provides for novel formulations of air freshener and room deodorizing products by incorporating bioactive glass into a combination of any of the above-listed ingredients.

The antimicrobial and pH effects of bioactive glass are particularly useful in air freshener and room deodorizing products to reduce bacteria and odor.

Bathroom and Kitchen Paper Products

The present invention includes novel formulations which incorporate bioactive glass into various brands of bathroom tissue, facial tissue, paper towel and napkin products such as the products marketed under the brand names Angel Soft, Bounty, Brawny, Brite-Life, Charmin, Cottonelle, Good & Plenty, Green Forest, Hi Dri, Kleenex, Marcal, Mardi Gras, Md Bath Tissue, Northern, Puffs, Purely Cotton, Scott, Scotties, So-Dri, Soft 'N Gentle, Sparkle, Vanity Fair, Viva, Wash 'N Dri, Zee, and products produced by high-end and generic manufacturers.

Common formulations of bathroom tissue, facial tissue, paper towel, and napkin products comprise purified wood pulp, skin conditioners, coloring agents and fragrance.

The present invention provides for novel formulations of bathroom tissue, facial tissue, paper towel and napkin products by incorporating bioactive glass into a combination of any of the above-listed ingredients.

Cleaning Accessory Products

The present invention includes novel formulations which incorporate bioactive glass into various brands of cotton swab, handiwipe, scouring and sponge products such as the products marketed under the brand names Arden, Ecko, Guardsman, Handi Wipes, Johnson & Johnson, Lysol, Mr. Clean, O-Cel-O, Pledge, Q-tips, S.O.S., Scotch Brite, and products produced by high-end and generic manufacturers.

The present invention provides for novel formulations of cotton swab, handiwipe, scouring and sponge products by incorporating bioactive glass into a combination of any of the above-listed ingredients.

The antimicrobial and pH effects of bioactive glass are particularly useful in cotton swab, handiwipe, scouring and sponge products to reduce bacteria and odor. Additionally, the abrasive effects of bioactive glass aid in the removal of dirt and stains.

Oven Cleaning Products

The present invention includes novel formulations which incorporate bioactive glass into various brands of oven cleaning products such as the products marketed under the brand names Dow, Easy Off, Kleen King, and products produced by high-end and generic manufacturers.

Generally, oven cleaning products comprise the active ingredient sodium hydroxide.

Common formulations of oven cleaning products comprise water, surfactants, grease cutting agents, sodium hydroxide, water conditioning agents, fragrance, and various coloring agents.

The present invention provides for novel formulations of oven cleaning products by incorporating bioactive glass into a combination of any of the above-listed ingredients.

The antimicrobial effects of bioactive glass are particularly useful in oven cleaning products to reduce bacteria and odor.

Toilet Cleaning Products

The present invention includes novel formulations which incorporate bioactive glass into various brands of toilet cleaning products such as the products marketed under the brand names Blu Boy, Bowl Fresh, Clorox, Dale, Dow, Lime Away, Lysol, Septonic, Sno Bol, Tiolet Duck, Ty-D-Bol, Vanish, Willert Bowl, and X-14, and products produced by high-end and generic manufacturers.

Generally, toilet cleaning products comprise the active ingredient oxacil acid.

Common formulations of toilet cleaning products comprise bromine, chlorine, 1-bromo-3-chloro-5,5-dimethylhydantoin, 1,3-dichloro-5,5-dimethylhydantoin, and 1,3-dichloro-5-ethyl-5-methylhydantoin.

Toilet cleaning products also may include one or more of the following: hydrogen chloride, alkyl, dimethyl benzyl ammonium chloride, octyl decyl dimethyl ammonium chloride, didecyl dimethyl ammonium chloride, and dioctyl dimethyl ammonium chloride.

The present invention provides for novel formulations of toilet cleaning products by incorporating bioactive glass into a combination of any of the above-listed ingredients.

The antimicrobial and pH effects of bioactive glass are particularly useful in toilet cleaning products to reduce bacteria and odor.

Tub and Shower Cleaning Products

The present invention includes novel formulations which incorporate bioactive glass into various brands of tub and shower cleaning products such as the products marketed under the brand names Clean Shower, Comet, Dow, Edfred, Lime-Away, Lysol, Parsons, Pine Sol, Scrub Free, Shower Power, Soft Scrub, Tilex, X-14, and products produced by high-end and generic manufacturers.

Generally, tub and shower cleaning products comprise sodium hypochlorite and/or calcium hypochlorite, a detergent and bleach.

Common formulations of tub and shower cleaning products comprise alkyl, dimethyl benzyl ammonium chlorides and detergents.

Tub and shower cleaning products also may include one or more of the following: dipropylene glycol butyl ether, citric acid, perfume, water, calcium carbonate, sodium hypochlorite, dimethyl ethylbenzyl ammonium chlorides, glycol ether, surfactants, soil suspending agents, cleaning agents, various processing agents, various coloring agents, and various quality control agents.

The present invention provides for novel formulations of tub and shower cleaning products by incorporating bioactive glass into a combination of any of the above-listed ingredients.

The antimicrobial and pH effects of bioactive glass are particularly useful in tub and shower cleaning products to reduce bacteria and odor.

Carpet Cleaning Products

The present invention includes novel formulations which incorporate bioactive glass into various brands of carpet cleaning products such as the products marketed under the brand names Arm & Hammer, Carpet Fresh, Folex, Formula 409, Glade, Simply Spot-Less, Spot Shot, Resolve, Shout, Woolite, and products produced by high-end and generic manufacturers.

Generally, carpet cleaning products comprise the active ingredient sodium bicarbonate and fragrance.

The present invention provides for novel formulations of carpet cleaning products by incorporating bioactive glass into a combination of any of the above-listed ingredients.

The antimicrobial and pH effects of bioactive glass are particularly useful in carpet cleaning products to reduce bacteria and odor.

All Purpose Cleaning Products

The present invention includes novel formulations which incorporate bioactive glass into various brands of all purpose cleaning products such as the products marketed under the brand names Amazing White, Biz, Borateem, Cloralen, Clorox, Ajax, Armstrong, Barkeepers Friend, Behold, Bon Ami, Brasso, Brite, Cameo, Cinch, Clear Calcium Lime Rust Remover, Clorox, Comet, Dow, Easy-Off, Endust, Fantastik, Formula 409, Glass Magic, Glass Plus, International Brass & Metal Polish, Johnson, Lysol, Mop & Glo, Mr. Clean, Murphy's, Old English, Pine O Pine, Pine Sol, Pledge, Proctor & Gamble, Orange Clean, Orange Glo, Scotts, Simple Green, Soft Scrub, Sparkle, Spic & Span, Tilex, Twinkle, Xtra, Weinmans, Wince, Wright, Wrights, and products produced by high-end and generic manufacturers.

Generally, all purpose cleaning products comprise sodium hypochlorite and/or calcium hypochlorite, a detergent, ammonia and alcohol.

Common formulations of all purpose cleaning products comprise sodium dichloro-S-triazinetrione dihydrate, cleaning agents (calcium carbonate, sodium carbonate, anionic surfactants), perfume, various quality control agents and various coloring agents.

All purpose cleaning products also may include one or more of the following: dipropylene glycol butyl ether, citric acid, bleach, N-alkyl dimethyl benzyl ammonium chlorides, N-alkyl dimethyl ethylbenzyl ammonium chloride, ammonia-D, octyl decyl dimethyl ammonium chloride, dioctyl dimethyl ammonium chloride, isopropanol and surfactants.

The present invention provides for novel formulations of all purpose cleaning products by incorporating bioactive glass into a combination of any of the above-listed ingredients.

The antimicrobial and pH effects of bioactive glass are particularly useful in general purpose cleaning products to reduce bacteria and odor. Additionally, the abrasive quality of bioactive glass aids in the removal of dirt and stains.

Jewelry and Metal Cleaning Products

The present invention includes novel formulations which incorporate bioactive glass into various brands of jewelry and metal cleaning products such as the products marketed under the brand names Brasso, International Brass & Metal Polish, Twinkle, and Wrights.

The present invention provides for novel formulations of jewelry and metal cleaning products by incorporating bioactive glass into any of the above-listed ingredients.

The abrasive and pH effects of bioactive glass are particularly useful in jewelry and metal cleaning products to reduce bacteria and to remove stains.

Food Preservatives, Nutritional Supplements and Functional Food Formulations

Food Preservatives

Numerous foods are potentially infected with bacteria, such as E. coli. Ground beef and chicken are particularly susceptible to bacterial infection. Aqueous solutions including an aqueous extract from bioactive glass have anti-bacterial properties. The anti-bacterial effect is due, in part, to the basic nature of the solution (pH greater than about 7, preferably greater than about 9, more preferably greater than about 10.5). However, sodium hydroxide solutions of relatively high pH are not as effective at killing bacteria. Accordingly, the solutions have additional antibacterial elements present than merely a relatively high pH.

The bioactive glass compositions may be sprayed on contaminated surfaces, or incorporated into food products such as ground beef. Since bioactive glass has been approved for various uses by the FDA, the extract of bioactive glass should be harmless to humans. In addition, bioactive glass has no effect on taste or texture.

It should be noted that in addition to bioactive glass, antibiotics may also be added to food preservatives, nutritional supplements and functional food formulations. The addition of antibiotics to food preservatives, nutritional supplements and functional food formulations which include bioactive glass is particularly effective in formulations which are orally ingested.

Functional Foods/Nutritional Supplements

It has been shown in several animal models that soluble silica is essential for proper absorption/metabolization of calcium. Thus, without adequate levels of soluble silica, the effects of supplemented calcium may be defeated. Accordingly, the addition of bioactive glass to calcium supplemented foods may improve calcium absorption.

In addition, antacids are increasingly being sold as calcium supplements. Accordingly the addition of bioactive glass to antacid formulation may increase calcium absorption, and due to its effects on pH also reduces acid.

Likewise, other calcium supplements and calcium added to foods such as orange juice, cereals, and nutritional shakes can benefit from the increased calcium absorption provided by bioactive glass. In addition, the anti-inflammatory properties of bioactive glass make it suitable as a treatment for internal inflammations such as stomach and intestinal inflammations.

Methods of Making

For enteral administration, the bioactive glass particulates can be incorporated into an inert carrier in discrete units such as capsules, cachets, tablets or lozenges, each containing a predetermined amount of the particles; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Categories of Functional Foods/Nutritional Supplements

One embodiment of the present invention will produce novel formulations which incorporate bioactive glass into various brands of a variety of functional food and nutritional supplements including: antacid products, calcium supplement products, and silica supplement products.

Antacid Products

The present invention includes novel formulations which incorporate bioactive glass into various brands of antacid products such as the products marketed under the brand names Alka-Mints, Alka-Seltzer, Amitone, Axid, Brite-Life, Bromo Seltzer, Di-Gel, Gas-X, Gaviscon, Gelusil, Good Sense, Imodium, Kaopectate, Lactaid, Maalox, Mag-Ox, Mylanta, Pepcid AC, Pepto-Bismol, Phazyme, Phillips, Prelief, Riopan, Rolaids, Sal De Picot, Tagamet, Tempo, Titralac, Tums, Zantac, an products produced by high-end and generic manufacturers.

Common formulations of antacid products comprise aspirin, sodium bicarbonate, citric acid, sodium citrate, sodium acetylsalicylate, aspartame, flavor and phenylalanine.

Antacid products also may include one or more of the following: calcium carbonate, magnesium stearate, mineral oil, sodium hexametaphosphate, starch, stearic acid, sucrose, talc, aluminum hydroxide, magnesium carbonate, alginic acid, calcium stearate, aspartame, croscarmellose sodium, silica, various artificial and natural flavorings, and various coloring agents.

The present invention provides for novel formulations of antacid products by incorporating bioactive glass into a combination of any of the above-listed ingredients.

The anti-inflammatory and antimicrobial effects of bioactive glass are particularly useful in antacid products to reduce inflammation and bacteria.

Calcium Supplement Products

The present invention includes novel formulations which incorporate bioactive glass into various brands of calcium supplement and calcium supplemented products including: dietary supplements in pill and chewable form, antacids, pain relievers, toothpaste, cereals, snack foods, beverages, and various food seasonings and spreads such as the products marketed under the brand names Alka-Mints, Amitone, Basic Nutrition, Bayer, Biotene, Black Radiance, Brite-Life, Calcet, Cal-Max, Caltrate, Centrum Kids, Citracel, Dical-D, Di-Gel, drugstore.com, Enamelon, Ensure, Equalactin, Estroven, FiberCon, Flintstones, Florical, FosFree, Futurebiotics, Gas-X, GNC, Good Sense, Healthy Woman, Konsyl, Maalox, Mylanta, Natrol, Naturalife, Natural Wealth, Naturally Scientific, Nature Made, Nature's Bounty, Nature's Reward, Nature's Way, Neo-Calglucon, Nephro-Calci, Nutrition Now, One-A-Day, Olry, Os-cal, PharmAssure, PhenSafe, Phillips, Posture, Prelief, Provate, R&C, R&D, Rainbow Light, Revlon, Roberts, Rolaids, Schiff, Similac, Solgar, Stuart Prenatal, Sundown, Surfak, Thompson, Titralac, Tums, Twinlab, Viactiv, VitaFresh, and products produced by high-end and generic manufacturers.

Common formulations of calcium supplement and calcium supplemented products comprise calcium carbonate, dicytl sodium sulfosuccinate, hydrogenated cereal solids, magnesium stearate, polyethylene glycol, sorbitol, sugar, various artificial and natural flavorings and various coloring agents.

Calcium supplement and calcium supplemented products also may include one or more of the following: adipic acid, silicon dioxide, sodium polyphosphate, starch, talc, aspartame, mannitol, maltodextrin, cellulose, mineral oil, crospovidone, hydroxypropyl methylcellulose, vegetable glycerides, acacia gum, titanium oxide, polysorbate 80, sodium lauryl sulfate and stearic acid.

The present invention provides for novel formulations of calcium supplement and calcium supplemented products by incorporating bioactive glass into a combination of any of the above-listed ingredients.

Silica Supplemented Products

The present invention includes novel formulations which incorporate bioactive glass into various brands of silica supplement and silica supplemented products including the following: dietary supplements in pill and chewable form, toothpaste, shampoo, body wash, and various food seasonings and spreads, such as the products marketed under the brand names Body Essential, Crest, Futurebiotics, GNC, Natrol, Nature's Herbs, Nature's Way, Peter Thomas Roth, and high-end and generic manufacturers.

Common formulations of silica supplement and silica supplemented products comprise stearic acid, dicalcium phosphate, cellulose, and magnesium stearate.

Silica supplement and silica supplemented products may also include one or more of the following: rice powder, silica, gelatin and water.

The present invention provides for novel formulations of silica supplement and silica supplemented products by incorporating bioactive glass into a combination of any of the above-listed ingredients.

Alternatively, bioactive glasss itself may be considered the silica supplement or may replace the silica found in existing formulations of silica supplements.

Applicants have found that bioactive glasses provide superior and unexpected results in comparison to standard dietary silica supplements. Applicants have found that bioactive glasses release soluble silica into physiological environments in beneficial ways that have not heretofore been appreciated. Bioactive glasses also provide for an unusually large physical surface area that presents silanol groups which have activity that in many ways is similar to soluble silica. Note that this is particularly true for sol-gel-derived glasses.

Applicants have found that both the released soluble silica and the available silanol groups provide for an efficient mechanism for sequestering and removing metal ions from the body. The glass particles, which may be micron-sized, sequester or bind metal ions and are flushed through organs of the body (e.g. the kidneys and intestines) and excreted from the body. In this way, bioactive glasses can be used to reduce or minimize the toxic effects of many metal ions.

Bioactive glasses are particularly helpful in reducing or minimizing the toxic effects of aluminum. In addition to the sequestering or binding discusssed above, bioactive glasses release additional calcium and phosphate, which aluminum tends to bind. The aluminum so bound is thus made less available for toxic effects or damaging physiological processes.

Accordingly, dietary supplements incorporating bioactive glass may be beneficial for treating or preventing many harmful disease processes and conditions associated with, for example, aluminum including, but not limited to, osteoporosis, osteodystrophy, and other conditions in which stimulation of of osteoblastic activity is desired.

In addition, these dietary supplements by binding aluminum, may be beneficial in preventing, slowing, or reversing the effects of Alzheimer's disease, various forms of encephalopathy, and various forms of myocardial dysfunction.

In addition to aluminum, bioactive glass can be used to bind other metal ions, including, for example, lead, cadmium, zinc, and iron. Accordingly, harmful or toxic effects of these and other metal ions may be prevented, slowed, or reversed.

Miscellaneous Products

In addition to the products listed above, bioactive glass may be added to or included in the following household products: dust filters, wall paint/wallpaper, toilet seat covers, mold remover, ceramic/bathroom tile laminates, water filters, mattress fillers, cleaning agents for solariums and sun beds, toilet brushes, pet litter (such as the products marketed under the brand names Litter Clean, Tidy Cat, Arm & Hammer, Classy Cat, Everfresh, Fresh Step, Jonny, Sani-Scoop and Scoop Away) and cutting boards to make these products highly resistant to microbial contamination and to increase the pH.

The present invention also provides novel products useful in the animal care and veterinary fields. Bioactive glass may also be added to or included, for example, in the following animal/veterinary products to make these products highly resistant to microbial contamination and to increase the pH: sand for bird cages, kitty litter, flea powder, and dry shampoos for animals.

Bioactive glass may also be added to or included in the following products: fungicide/pesticide for agriculture, marine antifoulant, coating for glass and cleaners for industrial food and beverage containers, concrete, ceramics, and tile, to name a few, to make these products highly resistant to microbial contamination and to increase the pH.

The numbered embodiments provided below further exemplify the invention and aspects therof.

1. A cosmetic composition comprising bioactive glass and a substantially anhydrous cosmetic formulation.
2. The composition of embodiment 1, wherein the bioactive glass is melt-derived.
3. The composition of embodiment 1, wherein the bioactive glass is sol-gel-derived.
4. The composition of embodiment 1, wherein the bioactive glass is an aqueous extract.
5. The composition of embodiment 1, wherein the substantially anhydrous cosmetic formulation is selected from the group consisting of: lipstick, lipbalm, eye shadow, eye foundation, make-up foundation, and face powder.
6. The composition of embodiment 1 in the formulation of Example 4B.

7. The composition of embodiment 1 in the formulation of Example 4C.
8. The composition of embodiment 1 in the formulation of Example 5.
9. The composition of embodiment 1 in the formulation of Example 6.
10. The composition of embodiment 1 in the formulation of Example 7.
11. The composition of embodiment 1 in the formulation of Example 8.
12. The composition of embodiment 27 in the formulation of Example 9.
13. The composition of embodiment 27 in the formulation of Example 10B.
14. A method of making a cosmetic composition comprising combining bioactive glass with a substantially anhydrous cosmetic formulation.
15. The method of embodiment 14, wherein the bioactive glass is melt-derived.
16. The method of embodiment 14, wherein the bioactive glass is sol-gel-derived.
17. The method of embodiment 14, wherein the bioactive glass is an aqueous extract.
18. The method of embodiment 14, wherein the substantially anhydrous cosmetic formulation is selected from the group consisting of: lipstick, lipbalm, eye shadow, eye foundation, make-up foundation, and face powder.
19. The method of embodiment 14 to make the formulation of Example 4B.
20. The method of embodiment 14 to make the formulation of Example 4C.
21. The method of embodiment 14 to make the formulation of Example 5.
22. The method of embodiment 14 to make the formulation of Example 6.
23. The method of embodiment 14 to make the formulation of Example 7.
24. The method of embodiment 14 to make the formulation of Example 8.
25. The method of embodiment 34 to make the formulation of Example 9.
26. The method of embodiment 34 to make the formulation of Example 10B.
27. A cosmetic composition comprising bioactive glass, a cosmetic formulation and a buffer.
28. The composition of embodiment 27, wherein the bioactive glass is melt-derived.
29. The composition of embodiment 27, wherein the bioactive glass is sol-gel-derived.
30. The composition of embodiment 27, wherein the bioactive glass is an aqueous extract.
31. The composition of embodiment 27, wherein the buffer is citric acid.
32. The composition of embodiment 27, wherein the cosmetic formulation is selected from the group consisting of: lipstick, lipbalm, eye shadow, eye foundation, make-up foundation, and face powder.
33. The composition of embodiment 27 in the formulation of Example 9.
34. A method of making a cosmetic composition comprising combining bioactive glass, a cosmetic formulation, and a buffer.
35. The method of embodiment 34, wherein the bioactive glass is melt-derived.
36. The method of embodiment 34, wherein the bioactive glass is sol-gel-derived.
37. The method of embodiment 34, wherein the bioactive glass is an aqueous extract.
38. The method of embodiment 34, wherein the buffer is citric acid.
39. The method of embodiment 34, wherein the cosmetic formulation is selected from the group consisting of: lipstick, lipbalm, eye shadow, eye foundation, make-up foundation, and face powder.
40. The method of embodiment 34 to make the formulation of Example 9.
41. A non-irritating, stable cosmetic composition comprising bioactive glass and a cosmetic formulation, wherein the pH of the composition is between about 8 and about 12.
42. A method of making a non-irritating, stable cosmetic composition comprising combining bioactive glass and a cosmetic formulation, wherein the pH of the composition is between about 8 and about 12.
43. A non-irritating cosmetic composition comprising bioactive glass and a cosmetic formulation, wherein said cosmetic formulation comprises at least on substance that is skin-irratating when not in the composition.
44. A method of reducing and/or preventing skin irritation comprising applying the cosmetic composition of embodiment 43 to the skin.
45. An odor reducing cosmetic composition comprising bioactive glass and a cosmetic formulation.
46. A method of reducing odor comprising applying the cosmetic composition of embodiment 45 to a source of odor.
47. A UV-filtering cosmetic composition comprising bioactive glass and a cosmetic formulation.
48. The cosmetic composition of embodiment 47, wherein the bioactive glass is sol-gel-derived.
49. The cosmetic composition of embodiment 47 in the formulation of Example 1.
50. The cosmetic composition of embodiment 47 in the formulation of Example 2.
51. The cosmetic composition of embodiment 47 in the formulation of Example 3.
52. A method of blocking UV light from exposed skin comprising applying the cosmetic composition of embodiment 47 to the exposed skin.
53. A method of blocking UV light from exposed skin comprising applying the cosmetic composition of embodiment 49 to the exposed skin.
54. A method of blocking UV light from exposed skin comprising applying the cosmetic composition of embodiment 50 to the exposed skin.
55. A method of blocking UV light from exposed skin comprising applying the cosmetic composition of embodiment 51 to the exposed skin.
56. A moisture-absorbing cosmetic composition comprising bioactive glass and a cosmetic formulation.
57. The cosmetic composition of embodiment 56, wherein the bioactive glass is sol-gel derived.
58. A method of absorbing moisture comprising applying the cosmetic composition of embodiment 56 to a source of moisture.
59. A personal care composition comprising bioactive glass and a personal care product.
60. The composition of embodiment 59, wherein the bioactive glass is melt-derived.
61. The composition of embodiment 59, wherein the bioactive glass is sol-gel-derived.
62. The composition of embodiment 59, wherein the bioactive glass is an aqueous extract.

63. The composition of embodiment 59, wherein the personal care product is selected from the group consisting of: diaper products, adult incontinence products, feminine hygiene products, shampoo products, hair care products, deodorant products, foot care products, baby care products, sunscreen products, body cleanser products, skin care products, and nutritional supplement products.

64. A method of making a personal care composition comprising combining bioactive glass, and a personal care product.

65. The method of embodiment 64, wherein the bioactive glass is melt-derived.

66. The method of embodiment 64, wherein the bioactive glass is sol-gel-derived.

67. The method of embodiment 64, wherein the bioactive glass is an aqueous extract.

68. The method of embodiment 64, wherein the personal care product is selected from the group consisting of: diaper products, adult incontinence products, feminine hygiene products, shampoo products, hair care products, deodorant products, foot care products, baby care products, sunscreen products, body cleanser products, skin care products, and nutritional supplement products.

69. A non-irritating, stable personal care composition comprising bioactive glass and a personal care product, wherein the pH of the composition is between about 8 and about 12.

70. A method of making a non-irritating, stable personal care composition comprising combining bioactive glass and a personal care product, wherein the pH of the composition is between about 8 and about 12.

71. An odor-reducing personal care composition comprising bioactive glass and a personal care product.

72. A method of reducing odor comprising applying the personal care composition of embodiment 71 to a source of odor.

73. A UV-filtering personal care composition comprising bioactive glass and a personal care product.

74. The UV-filtering personal care composition of embodiment 73, wherein the bioactive glass is sol-gel-derived.

75. The personal care composition of embodiment 73, wherein the personal care product comprises sunscreen.

76. The personal care composition of embodiment 73 in the formulation of Example 1.

77. The personal care composition of embodiment 73 in the formulation of Example 2.

78. The personal care composition of embodiment 73 in the formulation of Example 3.

79. A method of blocking UV light from exposed skin comprising applying the personal care composition of embodiment 73 to the exposed skin.

80. A method of blocking UV light from exposed skin comprising applying the personal care composition of embodiment 76 to the exposed skin.

81. A method of blocking UV light from exposed skin comprising applying the personal care composition of embodiment 77 to the exposed skin.

82. A method of blocking UV light from exposed skin comprising applying the personal care composition of embodiment 78 to the exposed skin.

83. A moisture-absorbing personal care composition comprising bioactive glass and a personal care product.

84. The moisture-absorbing personal care composition of embodiment 83, wherein the bioactive glass is sol-gel derived.

85. A method of absorbing moisture comprising applying the personal care composition of embodiment 83 to a source of moisture.

86. A hair care composition comprising bioactive glass and a hair care product, wherein the hair care composition provides a mineral coating to the hair.

87. The hair care composition of embodiment 86 in the formulation of Example 11.

88. The hair care composition of embodiment 86 in the formulation of Example 12A.

89. The hair care composition of embodiment 86 in the formulation of Example 13A.

90. The composition of embodiment 1 comprising Red 7 Ca Lake, Red 6 Ba Lake, Red 33 Al Lake, castor oil, carnauba wax, candellila wax, ozokerite wax, microcrystalline wax, jojoba oil, vitamin E, methyl paraben, propyl paraben, and 45s bioactive glass.

91. The composition of embodiment 1 comprising Red 7 Ca Lake, Red 6 Ba Lake, Red 33 Al Lake, castor oil, carnauba wax, candellila wax, ozokerite wax, microcrystalline wax, jojoba oil, vitamin E, methyl paraben, propyl paraben, 45s bioactive glass, and 58s bioactive glass.

92. The composition of embodiment 1 comprising jojoba glaze and bioactive glass, wherein the bioactive glass has an average particle size less than about 5 microns.

93. The composition of embodiment 1 comprising glycerin, Pemulen® TR-2, and bioactive glass, wherein the bioactive glass has an average particle size less than about 5 microns.

94. The composition of embodiment 1 comprising jojoba glaze, brown iron oxide, titanium dioxide, talc, and sol-gel-derived bioactive glass.

95. The composition of embodiment 27 comprising mineral oil, Polawax®, glycerin, deionized water, juguar C-14S, phenobact, fragrance, citric acid monohydrate powder, and sol-gel-derived bioactive glass.

96. The composition of embodiment 27 in the formulation of Example 10C.

97. The composition of embodiment 27, comprising crodafos CES, volpo 10, volpo 3, jojoba oil, cyclomethicone D5, deionized water, NaOH, TiO2, red iron oxide, 50/50 Black/brown iron oxide blend, propylene glycol, jaguar 13S, germaben II, and 45s bioactive glass.

98. The composition of embodiment 27, comprising crodafos CES, volpo 10, volpo 3, jojoba oil, cyclomethicone D5, deionized water, NaOH, TiO2, red iron oxide, 50/50 Black/brown iron oxide blend, propylene glycol, jaguar 13S, germaben II, and 58s bioactive glass.

99. The method of embodiment 14 to make a formulation comprising Red 7 Ca Lake, Red 6 Ba Lake, Red 33 Al Lake, castor oil, carnauba wax, candellila wax, ozokerite wax, microcrystalline wax, jojoba oil, vitamin E, methyl paraben, propyl paraben, and 45s bioactive glass.

100. The method of embodiment 14 to make a composition comprising Red 7 Ca Lake, Red 6 Ba Lake, Red 33 Al Lake, castor oil, carnauba wax, candellila wax, ozokerite wax, microcrystalline wax, jojoba oil, vitamin E, methyl paraben, propyl paraben, 45s bioactive glass, and 58s bioactive glass.

101. The method of embodiment 14 to make a composition comprising jojoba glaze and bioactive glass, wherein the bioactive glass has an average particle size less than about 5 microns.

102. The method of embodiment 14 to make a composition comprising glycerin, Pemulen® TR-2, and bioactive glass, wherein the bioactive glass has an average particle size less than about 5 microns.

103. The method of embodiment 14 to make a composition comprising jojoba glaze, brown iron oxide, titanium dioxide, talc, and sol-gel-derived bioactive glass.

104. The method of embodiment 34 to make a composition comprising mineral oil, Polawax®, glycerin, deionized water, juguar C-14S, phenobact, fragrance, citric acid monohydrate powder, and sol-gel-derived bioactive glass.

105. The method of embodiment 34 to make the formulation of Example 10C.

106. The method of embodiment 34 to make a composition comprising crodafos CES, volpo 10, volpo 3, jojoba oil, cyclomethicone D5, deionized water, NaOH, TiO2, red iron oxide, 50/50 Black/brown iron oxide blend, propylene glycol, jaguar 13S, germaben II, and 45s bioactive glass.

107. The method of embodiment 34 to make a composition comprising crodafos CES, volpo 10, volpo 3, jojoba oil, cyclomethicone D5, deionized water, NaOH, TiO2, red iron oxide, 50/50 Black/brown iron oxide blend, propylene glycol, jaguar 13S, germaben II, and 58s bioactive glass.

108. The composition of embodiment 47 comprising jojoba glaze, octyl methoxycinnamate, benzophenone-3 and bioactive glass.

109. The composition of embodiment 47 comprising jojoba glaze, octyl methoxycinnamate, benzophenone-3 and sol-gel-derived bioactive glass.

110. The composition of embodiment 73 comprising jojoba glaze, octyl methoxycinnamate, benzophenone-3 and bioactive glass.

111. The composition of embodiment 73 comprising jojoba glaze, octyl methoxycinnamate, benzophenone-3 and sol-gel-derived bioactive glass.

112. The composition of embodiment 86 comprising standopol ES, crosultaine C-50, foamid C, deionized water, jaguar C-14S, phenobact, fragrance, citric acid monhydrate powder, and bioactive glass.

113. The hair care composition of embodiment 86 in the formulation of Example 12D.

114. The composition of embodiment 86 comprising standopol ES, crosultaine C-50, foamid C, deionized water, phenobact, citric acid monhydrate powder, and bioactive glass.

115. The hair care composition of embodiment 86 in the formulation of Example 13B.

116. The hair care composition of embodiment 86 in the formulation of Example 13C.

117. The hair care composition of embodiment 86 in the formulation of Example 13D.

118. The composition of embodiment 86 comprising steol CS-230, crosultaine C-50, foamid C, deionized water, phenobact, citric acid monhydrate powder, and bioactive glass.

119. The composition of embodiment 86 comprising steol CS-230, crosultaine C-50, foamid C, deionized water, phenobact, and bioactive glass.

120. The composition of embodiment 1 comprising jojoba oil, Lubrajel® MS, pigment, and bioactive glass.

121. The composition of embodiment 1 comprising Polawax, mineral oil, glycerin, Jaguar C14-S, citric acid, Phenobact, colorant, fragrance, and bioactive glass.

122. The composition of embodiment 59 comprising a deodorant stick and bioactive glass, wherein the bioactive glass is between about 4% and about 10% by weight of the composition.

123. The composition of embodiment 59 comprising a deodorant cream and bioactive glass, wherein the bioactive glass is between about 30% and about 60% by weight of the composition.

124. A cleaning agent composition comprising bioactive glass and a cleaning agent.

125. The composition of embodiment 124, wherein the bioactive glass is melt-derived.

126. The composition of embodiment 124, wherein the bioactive glass is sol-gel-derived.

127. The composition of embodiment 124, wherein the bioactive glass is an aqueous extract.

128. The composition of embodiment 124, wherein the cleaning agent is selected from the group consisting of: laundry detergents, stain removers, fabric softening products, dish washing products, air fresheners, deodorizing products, bathroom tissue, facial tissue, paper towel products, napkin products, cotton swabs, handiwipes, scouring products, sponge products, oven cleaning products, toilet cleaning products, tub and shower cleaning products, carpet cleaning products, all purpose cleaning products, jewelry products, and metal cleaning products.

129. A method of making a cleaning agent composition comprising combining bioactive glass and a cleaning agent.

130. The method of embodiment 129, wherein the bioactive glass is melt-derived.

131. The method of embodiment 129, wherein the bioactive glass is sol-gel-derived.

132. The method of embodiment 129, wherein the bioactive glass is an aqueous extract.

133. The method of embodiment 129, wherein the cleaning agent is selected from the group consisting of: laundry detergents, stain removers, fabric softening products, dish washing products, air fresheners, deodorizing products, bathroom tissue, facial tissue, paper towel products, napkin products, cotton swabs, handiwipes, scouring products, sponge products, oven cleaning products, toilet cleaning products, tub and shower cleaning products, carpet cleaning products, all purpose cleaning products, jewelry products, and metal cleaning products.

134. A nutritional supplement composition comprising bioactive glass and a nutritional supplement.

135. The composition of embodiment 134, wherein the bioactive glass is melt-derived.

136. The composition of embodiment 134, wherein the bioactive glass is sol-gel-derived.

137. The composition of embodiment 134, wherein the bioactive glass is an aqueous extract.

138. The composition of embodiment 134 wherein the nutritional supplement is selected from the group consisting of: antacids, calcium supplements, and silica supplements.

139. The composition of embodiment 134, further comprising iodine.

140. A method of making a nutritional supplement composition comprising combining bioactive glass and a nutritional supplement.

141. The method of embodiment 140, wherein the bioactive glass is melt-derived.

142. The method of embodiment 140, wherein the bioactive glass is sol-gel-derived.

143. The method of embodiment 140, wherein the bioactive glass is an aqueous extract.

144. The method of embodiment 140, wherein the nutritional supplement is selected from the group consisting of. antacids, calcium supplements, and silica supplements.

What is claimed is:

1. A method for preserving cosmetic compositions comprising admixing bioactive glass and a substantially anhydrous cosmetic formulation, wherein said bioactive glass comprises from about 30% to about 96% silicon dioxide ($SiO_2$), from about 4% to about 46% calcium oxide (CaO), from about 1% to about 15% phosphorus oxide ($P_2O_5$) and up to about 35% sodium oxide ($Na_2O$), all by weight of said bioactive glass, with the proviso that said bioactive glass does not comprise ions of silver, copper or zinc, wherein said bioactive glass comprises from about 0.05% to about 30% by weight of said cosmetic composition, wherein said cosmetic formulation is selected from the group consisting of lip products, face powder products, hair care products, deodorant products and soap products, and wherein said composition does not result in a significant skin sensitivity response when applied.

2. The method of claim 1, wherein the bioactive glass is melt-derived.

3. The method of claim 1, wherein the bioactive glass is sol-gel derived.

4. The method of claim 1, wherein the substantially anhydrous cosmetic formulation comprises vitamin E and paraben.

5. The method of claim 1, wherein the substantially anhydrous cosmetic formulation comprises talc.

6. The method of claim 1, wherein the substantially anhydrous cosmetic formulation comprises jojoba glaze.

7. The method of claim 1, wherein the substantially anhydrous cosmetic formulation comprises glycerin.

8. The method of claim 1, wherein the substantially anhydrous cosmetic formulation comprises jojoba glaze and talc.

9. The method of claim 1, wherein the substantially anhydrous cosmetic formulation comprises Red 7 Ca Lake, Red 6 Ba Lake, Red 33 A1 Lake, castor oil, carnauba wax, candellila wax, ozokerite wax, microcrystalline wax, jojoba oil, vitamin E, methyl paraben, propyl paraben, and wherein the bioactive glass comprises 45s bioactive glass.

10. The method of claim 1, wherein the substantially anhydrous cosmetic formulation comprises jojoba glaze, and wherein the bioactive glass has an average particle size less than about 5 microns.

11. The method of claim 1, wherein the substantially anhydrous cosmetic formulation comprises glycerin, and wherein the bioactive glass has an average particle size less than about 5 microns.

12. The method of claim 1, wherein the substantially anhydrous cosmetic formulation comprises jojoba glaze, brown iron oxide, titanium dioxide, talc, and wherein the bioactive glass is sol-gel derived.

13. The method of claim 1, wherein the substantially anhydrous cosmetic formulation comprises jojoba oil, glyceryl polymethacrylate clathrate and pigment.

14. The method of claim 1, wherein the substantially anhydrous cosmetic formulation comprises emulsifying wax, mineral oil, glycerin, citric acid, colorant and fragrance.

* * * * *